US012569486B2

(12) United States Patent
Bradner et al.

(10) Patent No.: US 12,569,486 B2
(45) Date of Patent: Mar. 10, 2026

(54) CALMODULIN INHIBITORS, CHK2 INHIBITORS AND RSK INHIBITORS FOR THE TREATMENT OF RIBOSOMAL DISORDERS AND RIBOSOMAPATHIES

(71) Applicants: THE CHILDREN'S MEDICAL CENTER CORPORATION, Boston, MA (US); DANA-FARBER CANCER INSTITUTE, INC., Boston, MA (US)

(72) Inventors: James Bradner, Weston, MA (US); Jun Qi, Sharon, MA (US); Dennis Buckley, Cambridge, MA (US); Leonard I. Zon, Brookline, MA (US); Elizabeth Macari, Wilmington, MA (US)

(73) Assignees: THE CHILDREN'S MEDICAL CENTER CORPORATION, Boston, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 18/439,926

(22) Filed: Feb. 13, 2024

(65) Prior Publication Data

US 2024/0342173 A1 Oct. 17, 2024

Related U.S. Application Data

(60) Division of application No. 17/175,079, filed on Feb. 12, 2021, now Pat. No. 11,944,625, which is a continuation of application No. 16/315,899, filed as application No. PCT/US2017/041851 on Jul. 13, 2017, now Pat. No. 10,980,808.

(60) Provisional application No. 62/361,631, filed on Jul. 13, 2016.

(51) Int. Cl.

| | |
|---|---|
| ***A61K 31/517*** | (2006.01) |
| ***A61K 31/225*** | (2006.01) |
| ***A61K 31/403*** | (2006.01) |
| ***A61K 31/506*** | (2006.01) |
| ***A61K 31/519*** | (2006.01) |
| ***A61K 31/5415*** | (2006.01) |
| ***A61K 31/55*** | (2006.01) |
| ***A61K 31/7048*** | (2006.01) |
| ***A61K 45/06*** | (2006.01) |
| ***A61P 7/06*** | (2006.01) |

(52) U.S. Cl.

CPC .......... *A61K 31/517* (2013.01); *A61K 31/225* (2013.01); *A61K 31/403* (2013.01); *A61K 31/506* (2013.01); *A61K 31/519* (2013.01); *A61K 31/5415* (2013.01); *A61K 31/55* (2013.01); *A61K 31/7048* (2013.01); *A61P 7/06* (2018.01); *A61K 45/06* (2013.01)

(58) Field of Classification Search

CPC . A61K 31/353; A61K 31/519; A61K 31/7048

See application file for complete search history.

(56) References Cited

U.S. PATENT DOCUMENTS

| | | | | |
|---|---|---|---|---|
| 9,040,673 | B2 | 5/2015 | Hecht et al. | |
| 9,827,252 | B2 * | 11/2017 | Zon | A61K 31/5415 |
| 10,420,778 | B2 * | 9/2019 | Zon | A61K 31/4375 |
| 10,980,808 | B2 * | 4/2021 | Bradner | A61P 7/06 |
| 11,065,258 | B2 * | 7/2021 | Zon | A61K 31/4965 |
| 11,654,149 | B2 * | 5/2023 | Zon | A61K 31/4965 514/211.1 |
| 11,944,625 | B2 | 4/2024 | Bradner et al. | |
| 11,980,620 | B2 | 5/2024 | Doulatov et al. | |
| 12,215,351 | B2 * | 2/2025 | Zon | A61K 31/5513 |
| 12,280,064 | B2 * | 4/2025 | Zon | A61K 31/4184 |
| 2003/0229082 | A1 | 12/2003 | James et al. | |
| 2008/0033000 | A1 | 2/2008 | Chang et al. | |
| 2015/0265627 | A1 | 9/2015 | Zon et al. | |
| 2015/0329498 | A1 | 11/2015 | Romero et al. | |
| 2019/0314374 | A1 * | 10/2019 | Bradner | A61K 31/7048 |
| 2020/0188402 | A1 | 6/2020 | Doulatov et al. | |
| 2022/0008420 | A1 | 1/2022 | Bradner et al. | |
| 2024/0299391 | A1 | 9/2024 | Doulatov et al. | |

FOREIGN PATENT DOCUMENTS

| | | | |
|---|---|---|---|
| GB | 716230 | A | 9/1954 |
| WO | WO-2003/062388 | A2 | 7/2003 |
| WO | WO-2003/062388 | A3 | 2/2004 |
| WO | 2009040512 | A2 | 4/2009 |

(Continued)

OTHER PUBLICATIONS

Doulatov et al. "Drug discovery for Diamond-Blackfan anemia using reprogrammed hematopoietic progenitors"; Feb. 8, 2017, Science Translational Medicine, 9(376): eaah5645.

Fujii et al "Studies on the Syntheses of Phenothiazine Derivatives. II. On the Reduction of 10-ß-Cyanoethylphenothiazines", JStage vol. 76 pp. 640-644 (1956).

Heijnen et al., "Ribosomal protein mutations induce autophagy through S6 kinase inhibition of the insulin pathway", PLoS Genetics 10(5): e1004371 15 pages (2014).

(Continued)

*Primary Examiner* — George W Kosturko

(74) *Attorney, Agent, or Firm* — Nixon Peabody LLP; David S. Resnick; Ravinderjit S. Braich

(57) ABSTRACT

The present invention relates to methods, compositions and kits for treatment of ribosomal disorders and ribosomopathies, e.g. Diamond Blackfan anemia (DBA). In some embodiments, the invention relates to the use of novel classes of compounds, i.e. inhibitors of RSK (p90S6K); inhibitors of p70S6K; and inhibitors of rps6, to treat ribosomal disorders and ribosomopathies. In some embodiments, the invention relates to the use of specific Chk2 inhibitors and to the use of specific phenothiazine derivatives to treat ribosomal disorders and ribosomopathies, e.g. DBA.

6 Claims, 54 Drawing Sheets

Specification includes a Sequence Listing.

(56) References Cited

FOREIGN PATENT DOCUMENTS

| | | | | | |
|---|---|---|---|---|---|
| WO | WO-2009/040512 | A3 | | 12/2009 | |
| WO | 2010033643 | A2 | | 3/2010 | |
| WO | WO-2010/033643 | A3 | | 5/2010 | |
| WO | WO-2011019995 | A2 | * | 2/2011 | A61K 31/353 |
| WO | WO-2013138101 | A2 | * | 9/2013 | A61K 31/145 |
| WO | 2013181742 | A1 | | 12/2013 | |
| WO | WO-2018/013761 | A1 | | 1/2018 | |
| WO | WO-2018/226230 | A1 | | 12/2018 | |

OTHER PUBLICATIONS

Hilinksi et al., "Analogs of the RSK inhibitor SL0101: optimization of in vitro biological stability", Bioorganic & Medicinal Chemistry Letters 22(9): 3244-3247 (2012).

Horig et al., "From bench to clinic and back: Perspective on the 1st IQPC Translational Research conference". Journal of Translational Medicine. Dec. 2004, 2, 44.

International Search Report and Written Opinion for International Application No. PCT/US17/36520 mailing date Oct. 18, 2017.

International Search Report and Written Opinion for International Application No. PCT/US17/41851 mailing date Nov. 9, 2017.

Macari et al., "Calmodulin Inhibition Rescues the Effects of Ribosomal Protein Deficiency in in Vitro and In Vivo Diamond Blackfan Anemia Models." Blood 126(23):672 (2015).

Pearce et al., "Characterisation of PF-4708671, a novel and highly specific inhibitor of p70 ribosomal S6 kinase (S6K1)", Biochemical Journal 431:245-255 (2010).

Schafer et al., "Failure is an option: learning from unsuccessful proof-of-concept trials". Drug Discovery Today. Nov. 2008, 13, 913-916.

Supplementary European Search Report for EP Application No. 17828436.0 dated Jun. 23, 2020.

Supplementary Partial European Search Report for EP Application No. 17828436.0 dated Feb. 14, 2020.

Vlachos et al., "Diagnosing and treating Diamond Blackfan anaemia: results of an international clinical consensus conference." British Journal of Haematology 142(6) : 859-876 (2008).

Extended European Search Report for EP Application No. 24174240.2 dated Oct. 16, 2024.

Database Biosis [Online] Biosciences Information Service, Philadelphia, PA, US; Dec. 2015 (Dec. 2015), Macari Elizabeth R et al: "Calmodulin Inhibition Rescues the Effects of Ribosomal Protein Deficiency in in Vitro and In Vivo Diamond Blackfan Anemia Models", XP002797186, Database accession No. PREV201600270547 *abstract*.

Fujii et al. "Synthesis of Phenothiazine Derivatives. II. Reduction of 10-(β-Cyanoethy) Phenothiazines" Yakugaku Zasshi vol. 76:640-644 (1956).

Heijnen et al. "Ribosomal protein mutations induce autophagy through S6 kinase inhibition of the insulin pathway." PLoS Genetics 10(5): e1004371 pp. 1-15 (2014).

Hilinski et al. "Analogs of the RSK inhibitor SL0101: optimization of in vitro biological stability." Bioorganic & Medicinal Chemistry Letters 22(9): 3244-3247 (2012).

Pearce et al., "Characterization of PF-4708671, a novel and highly specific inhibitor of p70 ribosomal S6 kinase (S6K1)", Biochemical Journal 431:245-255 (2010).

* cited by examiner

Additional Ribosomopathies

| Disease | Gene(s) | Clinical Features |
|---|---|---|
| 5q - Myelodysplasia | RPS14 | Dysplastic bone marrow |
| Schwachman-Diamond syndrome | SBDS - involved in ribosomal subunit joining | Pancreatic insufficiency, defective hematopoieisis, increased leukemia risk |
| Treacher Collins syndrome | TCOF1 - required for transcription of ribosomal DNA | Craniofacial abnormalities |

*FIG. 2*

CaM inhibitors
TFP
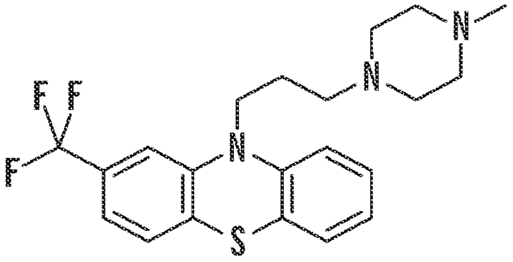
A-3
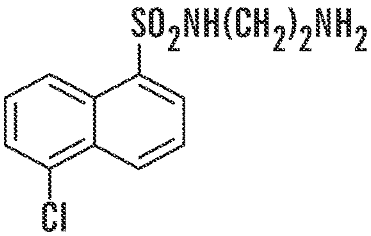
W-7
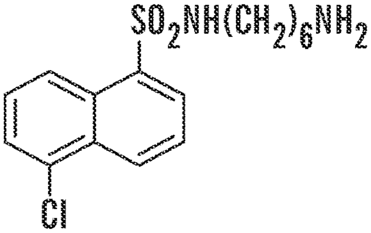
Chk2 inhibitors
CCT
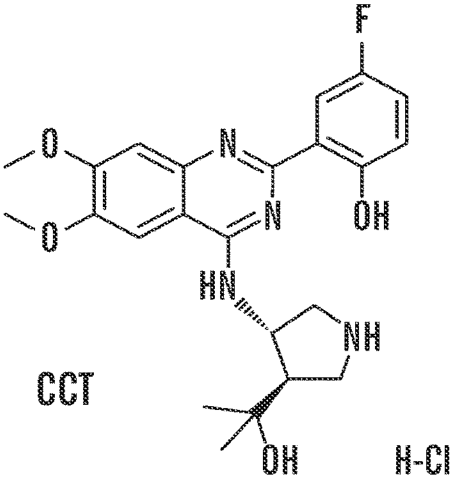
III
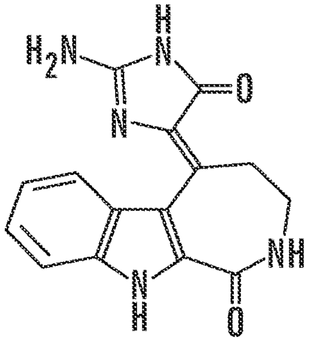
FIG. 5B Calmodulin (CaM)

From Anjum and Blenis *Nature Reviews Molecular Cell Biology*, 2008

Microarray of *rps29*$^{+/-}$ vs *rps29*$^{-/-}$

| Gene | Mean Fc (Log2) | Mean Fc | q Value |
|---|---|---|---|
| rps6KA3 (RSK2) | 0.69486 | 1.618 | 0.03 |
| MDM2 | 0.844 | 1.8 | 0.00 |
| p53 | 0.49984 | 1.414 | 0.01 |

Generation of Phenothiazine derivatives

Synthesis 1: Systematic diversification of phenothiazines

Compounds retain the phenothiazine ring and diversify the piperazine

Generation of Phenothiazine derivitives

Synthesis 2: Focused library

Explore biological activity around the tricyclic ring system

Commercially Available Compounds Used
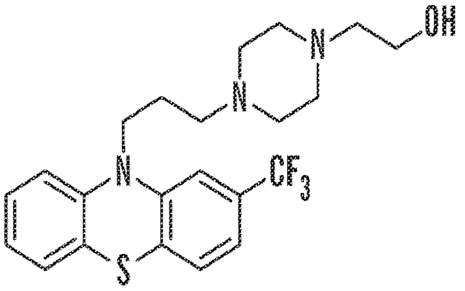
Fluphenazine
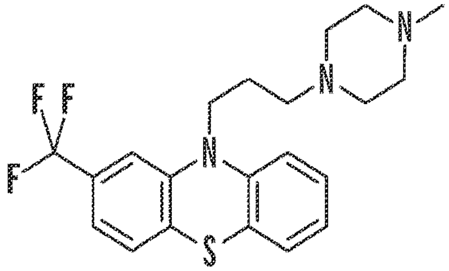
Trifluoperazine (TFP)
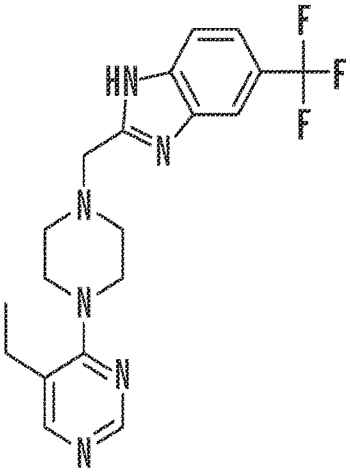
PF-4708671
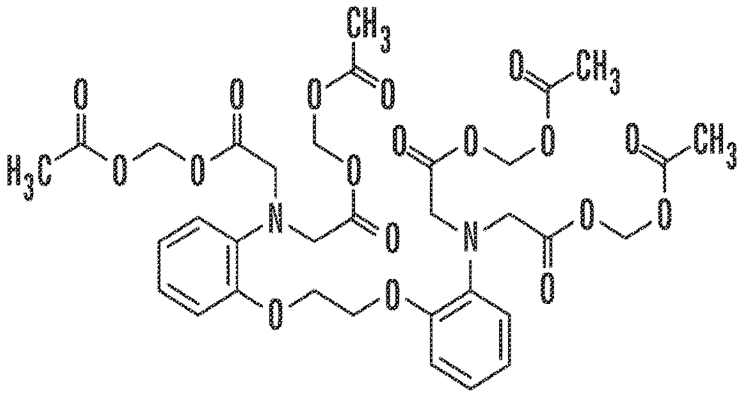
BAPTA-AM
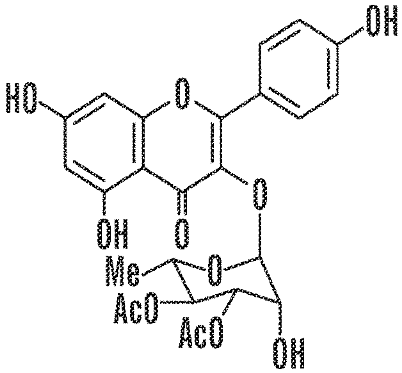
SL0101
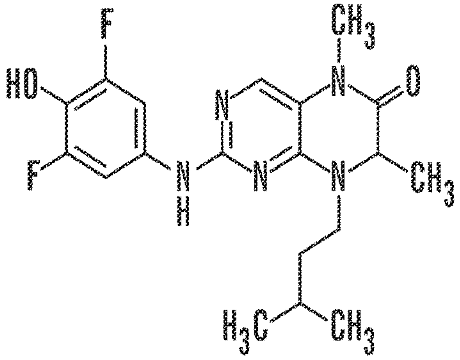
BI-D1870
*FIG. 31*

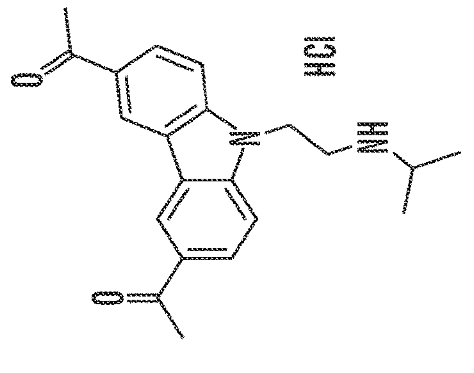
ACV-1-235
Cleveland biolabs compound
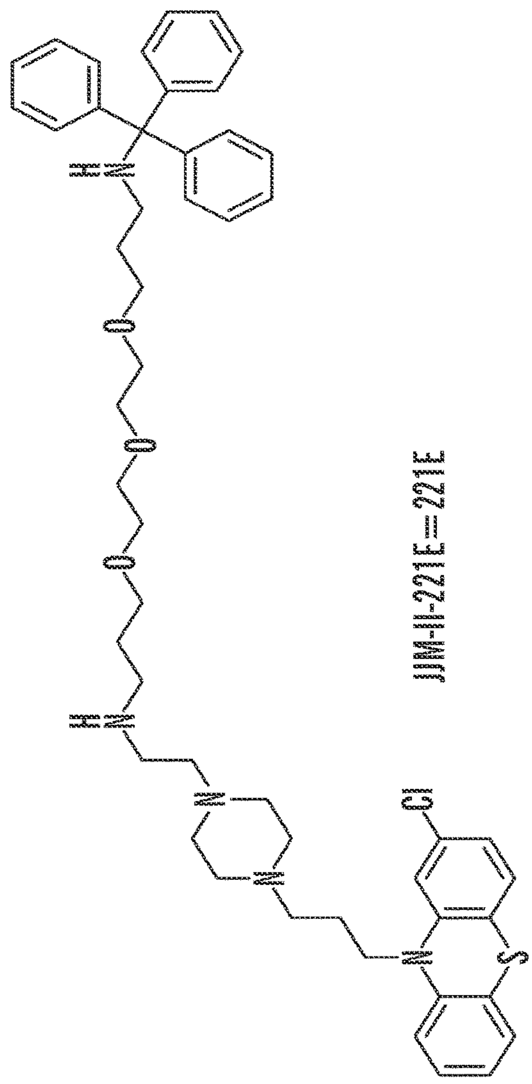
JJM-II-221E—221E
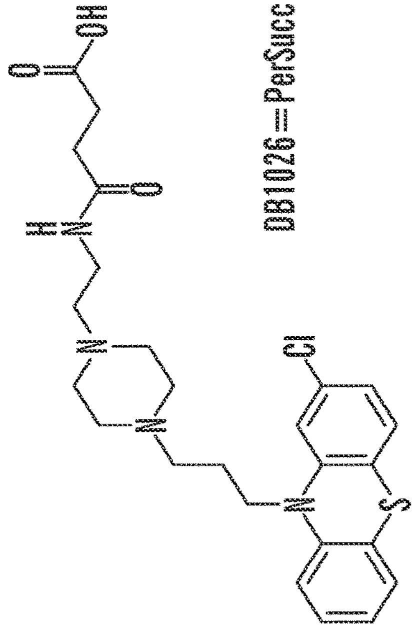
DB1026—PerSucc
*FIG. 32*

Novel phenothiazine derivatives
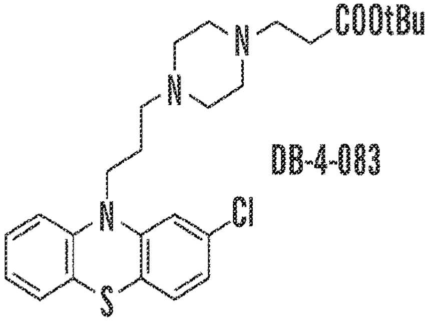
DB-4-083
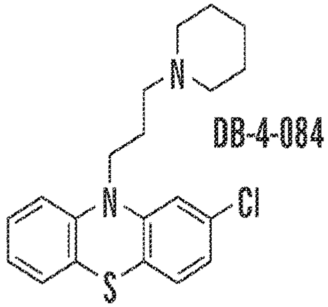
DB-4-084
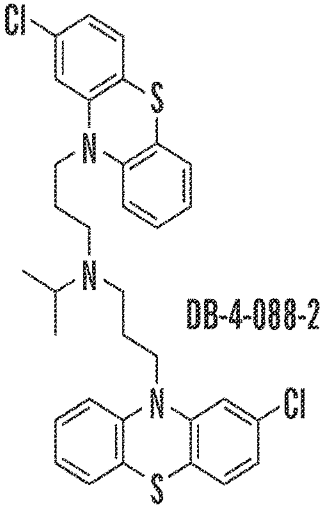
DB-4-088-2
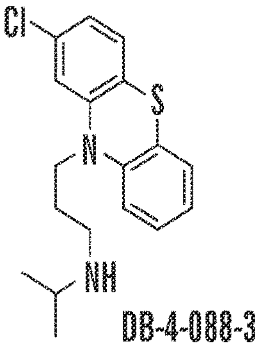
DB-4-088-3
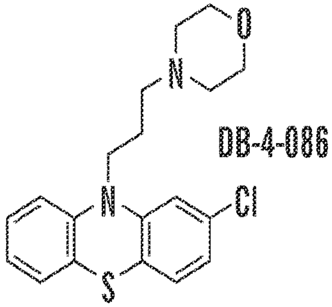
DB-4-086
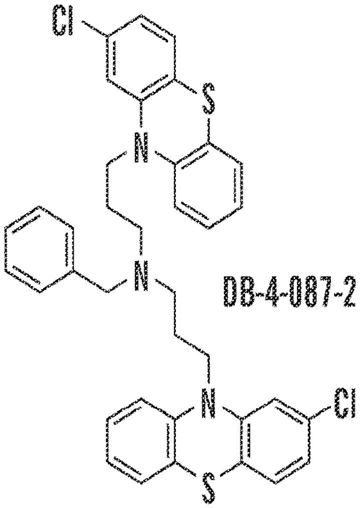
DB-4-087-2
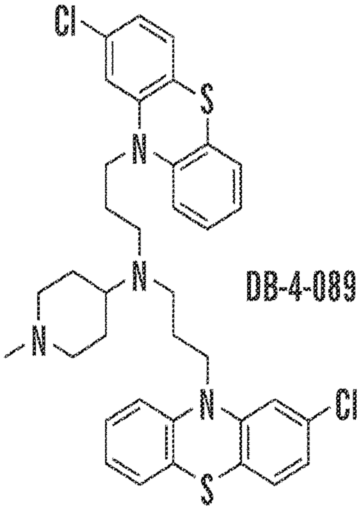
DB-4-089
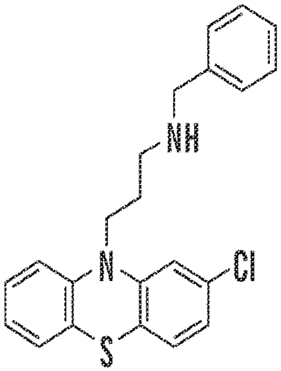
DB-4-087-3
Future slides display abbreviated compound names: DB-4-083 = 083
*FIG. 33*

083 decreases movement of zebrafish

DB-4-083

DB_4_088_2

DB-4-089

DB_4_088_3

| Drugs that increased Hb in rps29-/- embryos at lower concentrations than Flu | Drugs that did not increase Hb | Drugs that were tested in behavior screen | Drugs that did not change behavior | Drugs that changed behavior | Drugs that increased RBC differentiation |
|---|---|---|---|---|---|
| 089 | 086 | 089 | 088-2 | 089 | 088-2 |
| 088-3 | 084 | 088-3 | | 088-3 | 089 |
| 088-2 | 083 | 088-2 | | 083 | |
| | | 083 | | | |
| | | | | | |

FIG. 43

SEQUENCE LISTING

```
Sequence total quantity: 5
SEQ ID NO: 1           moltype = DNA  length = 5871
FEATURE                Location/Qualifiers
source                 1..5871
                       mol_type = unassigned DNA
                       organism = Homo sapiens
SEQUENCE: 1
aggcgtggcg cgtggccggc gctggtactc gcaggggagg cggagaagga ggcggaggga  60
gcgattgtgg ccccggccgc ggtggccggc gcggcctgcc ctttgtgacc gcagctcgcg  120
ccccacgccc cgcgcccatg gccgccgtgc cgggctccct ggccacgcgt gcccgcccgc  180
```

-continued

```
ggacctgagc cccgcgcctg ggatgccggg gatgcgcgtc ccccggccct gcggctgctc  240
cgggctgggc gcggggcgat ggacctgagc atgaagaagt tcgccgtgcg caggttcttc  300
tctgtgtacc tgcgcaggaa gtcgcgctcc aagagctcca gcctgagccg gctcgaggaa  360
gaaggcgtcg tgaaggagat agacatcagc catcatgtga aggagggctt tgagaaggca  420
gatccttccc agtttgagct gctgaaggtt ttaggacaag gatcctatgg aaaggtgttc  480
ctggtgagga aggtgaaggg gtccgacgct gggcagctct acgccatgaa ggtccttaag  540
aaagccaccc taaaagttcg ggaccgagtg agatcgaaga tggagagaga catcttggca  600
gaagtgaatc acccctcat tgtgaagctt cattatgcct ttcagacgga aggaaagctc  660
tacctgatcc tggacttcct gcggggaggg gacctcttca cccggctctc caaagaggtc  720
atgttcacgg aggaggatgt caagttctac ctggctgagc tggccttggc tttagaccat  780
ctccacagcc tggggatcat ctacagagat ctgaagcctg agaacatcct cctggatgaa  840
gaggggcaca ttaagatcac agatttcggc ctgagtaagg aggccattga ccacgacaag  900
agagcgtact ccttctgcgg gacgatcgag tacatggcgc ccgaggtggt gaaccggcga  960
ggacacacgc agagtgccga ctggtggtcc ttcggcgtgc tcatgtttga gatgctcacg  1020
gggtccctgc cgttccaggg gaaggacagg aaggagacca tggctctcat cctcaaagcc  1080
aagctgggga tgccgcagtt cctcagtggg gaggcacaga gtttgctgcg agctctcttc  1140
aaacggaacc cctgcaaccg gctgggtgct ggcattgacg gagtggagga aattaagcgc  1200
catcccttct ttgtgaccat agactggaac acgctgtacc ggaaggagat caagccaccg  1260
ttcaaaccag cagtgggcag gcctgaggac accttccact ttgaccccga gttcacagcg  1320
cggacgccca cagactctcc tggcgtcccc ccgagtgcaa acgctcatca cctgtttaga  1380
ggattcagct ttgtggcctc aagcctgatc caggagccct cacagcaaga tctgcacaaa  1440
gtcccagttc acccaatcgt gcagcagtta cacgggaaca acatccactt caccgatggc  1500
tacgagatca aggaggacat cggggtgggc tcctactcag tgtgcaagcg atgtgtgcat  1560
aaagccacag acaccgagta tgccgtgaag atcattgata agagcaagag agacccctcg  1620
gaagagattg agatcctcct gcggtacggc cagcacccga acatcatcac cctcaaggat  1680
gtctatgatg atggcaagtt tgtgtacctg gtaatggagc tgatgcgtgg tggggagctc  1740
ctggaccgca tcctccggca gagatacttc tcggagcgcg aagccagtga cgtcctgtgc  1800
accatcacca agaccatgga ctacctccat tcccaggggg ttgttcatcg agacctgaag  1860
ccgagtaaca tcctgtacag ggatgagtcg gggagcccag aatccatccg agtctgcgac  1920
ttcggctttg ccaagcagct gcgcgcgggg aacgggctgc tcatgacacc ctgctacacg  1980
gccaatttcg tggccccgga ggtcctgaag cgtcaaggct atgatgcggc gtgtgacatc  2040
tggagtttgg ggatcctgtt gtacaccatg ctggcaggat ttaccccttt tgcaaatggg  2100
ccagacgata cccctgagga gattctggcg cggatcggca gtgggaagta tgccctttct  2160
gggggaaact gggactcgat atctgacgca gctaaagacg tcgtgtccaa gatgctccac  2220
gtggaccctc atcagcgcct gacggcgatg caagtgctca aacacccgtg ggtggtcaac  2280
agagagtacc tgtccccaaa ccagctcagc cgacaggacg tgcacctggt gaagggcgcg  2340
atggccgcca cctactttgc tctaaacaga acacctcagg ccccgcggct ggagcccgtg  2400
ctgtcatcca acctggctca gcgcagaggc atgaagagac tcacgtccac gcggctgtag  2460
cgggtgggac cctggcccca gcgtcccctg ccagcatcct cgtgggctca cagaccccgg  2520
cctcggagcc cgtctggcac ccagagtgac cacaagtcca gcagggaggc ggcgcccgcc  2580
ctcgccgtgt ccgtgttttc tttttcagcc ccggagaggg tcctgacctg gggcttctc  2640
caagcctcac tgcgccagcc tccccgcccg ctctcttttc tcccaagcga aaccaaatgc  2700
gccccttcac ctcgcgtgcc cgtgcgaggc cgggggcttc tttcagagcc cgcgggtcct  2760
ctcatacatg gcttctgttt ctgccgagag atctgttttc caattatgaa gccggtcggt  2820
ttggtcagac tcccgacacc cacgtcccag gtacccggtg ggaaagtggc agtgcgaggg  2880
cgcagccatt ggtggttgca gggccccaga gggctggggt gacctggcat cccggggctc  2940
cccacgggct ggatgacggg gttggcactg tggcgtccag gaggagatgc ctggttctgc  3000
ccaaaataat ccaaagagcc gtttcctcct cgcccttcag tttttgcctg aggtgctggg  3060
tagcccatcc tttcctctgt cccagattca aatgaggagt aagagcccag acgagaggaa  3120
ggcaggctgg atctttgcct tgagagctcc gtgtcaccag gatggaaggg ggtgcctctc  3180
ggaggagcct gtgtccacct ccagtctcgg ctttccccgg ggggccaagc gcactgggct  3240
gccgtctgtc cccagctccc gtggccacac agctatctgg aggctttgca gggagtcgtg  3300
ggttctcgca cctgctcagc cctgtgtcgg cttcctgtgt gctcacctaa agctgtggtt  3360
ttgctgtgtt cacttcgatt tttctggtct gtggagaaac tgtgaattgg agaaatggag  3420
ctctgtggct tcccacccaa accttctcag tccagctgga ggctggaggg agacacaggc  3480
cccacccagc agactgaggg gcagaggcac aggtgggagg gcagcggaga tcagcgtgga  3540
caggagcgat gcactttgta gatgctgtgg ctttgtgttg cgttttgtgt ctctgttgca  3600
cagatctgtt ttttcacact gatccgtatt cccctgggtg tgcacacagg gcgggtgtgg  3660
ggcatttagg ccatgctgtg ctctacttca ttgagtaaaa tcgagtgaga ggttccgggc  3720
agcaggatcg acgcccagtc cagccggcag agggaacaca cgggtccttc attgtcctgt  3780
aagggtgttg aagatgctcc ctggcggccc ccaagcagac tagatgggag gaggcgccgc  3840
tcagcccctc accctgcatc actgaagagc ggcgcctctg cagcaagcag ggcttcagga  3900
ggtgcccgct ggccacagcc aggttttccc taagaagatg ttattttgtt gggttttgtt  3960
ccccctccat ctcgattctc gtacccaact aaaaaaaaaa aaataaagaa aaaatgtgct  4020
gcgttctgaa aaataactcc ttagcttggt ctgattgttt tcagacctta aaatataaac  4080
ttgtttcaca agctttaatc catgtggatt tttttttct tagagaacca caaaacataa  4140
aaggagcaag tcggactgaa tacctgtttc catagtgccc acagggtatt cctcacattt  4200
tctccataga agatgctttt tcccaaggct agaacgactt ccaccatgat gaatttgctt  4260
tttaggtctt aattatttca cttcttttta gaaacttagg aagaagtgga taatcctgag  4320
gtcacacaat ctgtcctccc agaaatgaac aaaagtcatc acctttctg cttgctacac  4380
aggcaacgat tcccccatca gctgcccgga ccctttggcc tggcttggtg tgcaggcctg  4440
tctgtttgct taaagtcagt gggttctggt gcagggagtg agaagtgggg gaagtgaaag  4500
ggaaagcatc cgtgagaaag cggccacggt tttccctcct tgtgtgccca tggggcacca  4560
gctcatggtc tttttcagtc atcccagttt gtacagactt agcttctgaa ctctaagaat  4620
gccaaaggga ccgacgagac tccccatcac agcgagctct gtccttacat gtatttgatg  4680
tgcatcagcg gaggagaaca ctggcttggc cctgctccgc tgagtgtctg tgaaataccct  4740
ctactttccc tcccatatcc agaacaaaat gatacttgac atccttccac aaaagtcagc  4800
ctaaagaagt tatggtatca tatgttaaac taagctttca aaaccttag tgaaatagca  4860
agtgactgct ttcaagcagc agtcgacatg taaatgaagg tgttcttaga attcgcattt  4920
```

```
tgccagctca gcgcacctcc acaacgaatg aaatgctccg tatgatttgc acaaatgaca  4980
tagacctccc caaaagttaa ctggctctcc ttcctcacac agttcatcat aacccaaccc  5040
cccaccccg ggtcatgaaa atcacagaac ttataaacac attgaaccct agatctcagg  5100
cttcctgacc taccgccagt ggccccttgc tggccaccct atagggtcct ccttccctgg  5160
cagcccccca tgtgggagaa atacctgatt ctcccaatct gcagtgggag agctttgctg  5220
aattccatcc caaagtcaaa catgggcaag aggtgaggat ttcactttta ccctcaagtc  5280
cgatttgtct gtgattttaa actaactgtg tatgtattga tgtttggaag attgtttgaa  5340
ttttaaagtg ataatagtac ttaatgttat ccagtattgt tcattaaatg gtgttatcct  5400
aaagctgcac ttgggatttt tacctaacgc tttactgatt ctctcaagca catggcaaag  5460
tttgatttgc actccgttca tttctgacac gttttgctgc ctcctacctt tctaagcgtc  5520
atgcaaattc gagaatggag aaggacgctg ccggtccctg agcggtgtgg agagggcgga  5580
aggtggactc cagcgcagct tgaggggctg aggacggagg ctgcagcatc tgtgtcgttc  5640
tactgagcac gcttctctgc ctcgctcctg actcagcact ttgttcactg gctcagcagt  5700
tatgtttaca catcattttt atgttcctgc tttgtaattc atgtttgaga tgggtggcca  5760
ctgtacagat atttattacg ctttccagac tttctgaata gatttttttg aataaacatg  5820
gttttatgaa gtgtaatctt tttctagcct aacaataaaa aaaaaaaaaa a           5871

SEQ ID NO: 2            moltype = AA  length = 733
FEATURE                 Location/Qualifiers
source                  1..733
                        mol_type = protein
                        organism = Homo sapiens
SEQUENCE: 2
MDLSMKKFAV RRFFSVYLRR KSRSKSSSLS RLEEEGVVKE IDISHHVKEG FEKADPSQFE  60
LLKVLGQGSY GKVFLVRKVK GSDAGQLYAM KVLKKATLKV RDRVRSKMER DILAEVNHPF  120
IVKLHYAFQT EGKLYLILDF LRGGDLFTRL SKEVMFTEED VKFYLAELAL ALDHLHSLGI  180
IYRDLKPENI LLDEEGHIKI TDFGLSKEAI DHDKRAYSFC GTIEYMAPEV VNRRGHTQSA  240
DWWSFGVLMF EMLTGSLPFQ GKDRKETMAL ILKAKLGMPQ FLSGEAQSLL RALFKRNPCN  300
RLGAGIDGVE EIKRHPFFVT IDWNTLYRKE IKPPFKPAVG RPEDTFHFDP EFTARTPTDS  360
PGVPPSANAH HLFRGFSFVA SSLIQEPSQQ DLHKVPVHPI VQQLHGNNIH FTDGYEIKED  420
IGVGSYSVCK RCVHKATDTE YAVKIIDKSK RDPSEEIEIL LRYGQHPNII TLKDVYDDGK  480
FVYLVMELMR GGELLDRILR QRYFSEREAS DVLCTITKTM DYLHSQGVVH RDLKPSNILY  540
RDESGSPESI RVCDFGFAKQ LRAGNGLLMT PCYTANFVAP EVLKRQGYDA ACDIWSLGIL  600
LYTMLAGFTP FANGPDDTPE EILARIGSGK YALSGGNWDS ISDAAKDVVS KMLHVDPHQR  660
LTAMQVLKHP WVVNREYLSP NQLSRQDVHL VKGAMAATYF ALNRTPQAPR LEPVLSSNLA  720
QRRGMKRLTS TRL                                                   733

SEQ ID NO: 3            moltype = DNA  length = 5368
FEATURE                 Location/Qualifiers
source                  1..5368
                        mol_type = unassigned DNA
                        organism = Homo sapiens
SEQUENCE: 3
gtttggcttc acggaaccct gtacgcatgc tcctacgctg aactttagga gccagtctaa  60
ggcctaggcg cagacgcact gagcctaagc agccggtgat ggcggcagcg gctgtggtgg  120
ctgcggcggg tccgggccca tgaggcgacg aaggaggcgg gacggctttt acccagcccc  180
ggacttccga gacagggaag ctgaggacat ggcaggagtg tttgacatag acctggacca  240
gccagaggac gcgggctctg aggatgagct ggaggagggg ggtcagttaa atgaaagcat  300
ggaccatggg ggagttggac catatgaact tggcatggaa cattgtgaga aatttgaaat  360
ctcagaaact agtgtgaaca gagggccaga aaaaatcaga ccagaatgtt ttgagctact  420
tcgggtactt ggtaaagggg gctatggaaa ggtttttcaa gtacgaaaag taacaggagc  480
aaatactggg aaaatatttg ccatgaaggt gcttaaaaag gcaatgatag taagaaatgc  540
taaagataca gctcatacaa aagcagaacg gaatattctg gaggaagtaa agcatccctt  600
catcgtggat ttaatttatg cctttcagac tggtggaaaa ctctacctca tccttgagta  660
tctcagtgga ggagaactat ttatgcagtt agaaagagag ggaatattta tggaagacac  720
tgcctgcttt tacttggcag aaatctccat ggctttgggg catttacatc aaaaggggat  780
catctacaga gacctgaagc cggagaatat catgcttaat caccaaggtc atgtgaaact  840
aacagacttt ggactatgca aagaatctat tcatgatgga acagtcacac acacattttg  900
tggaacaata gaatacatgg cccctgaaat cttgatgaga agtggccaca atcgtgctgt  960
ggattggtgg agtttgggag cattaatgta tgacatgctg actggagcac ccccattcac  1020
tggggagaat agaaagaaaa caattgacaa aatcctcaaa tgtaaactca atttgcctcc  1080
ctacctcaca caagaagcca gagatctgct taaaaagctg ctgaaaagaa atgctgcttc  1140
tcgtctggga gctggtcctg gggacgctgg agaagttcaa gctcatccat tctttagaca  1200
cattaactgg gaagaacttc tggctcgaaa ggtggagccc ccctttaaac ctctgttgca  1260
atctgaagag gatgtaagtc agtttgattc caagtttaca cgtcagacac ctgtcgacag  1320
cccagatgac tcaactctca gtgaaagtgc caatcaggtc tttctgggtt ttacatatgt  1380
ggctccatct gtacttgaaa gtgtgaaaga aaagttttcc tttgaaccaa aaatccgatc  1440
acctcgaaga tttattggca gcccacgaac acctgtcagc ccagtcaaat tttctcctgg  1500
ggatttctgg ggaagaggtg cttcggccag cacagcaaat cctcagacac ctgtggaata  1560
cccaatggaa acaagtggca tagagcagat ggatgtgaca atgagtgggg aagcatcggc  1620
accacttcca atacgacagc cgaactctgg gccatacaaa aaacaagctt ttcccatgat  1680
ctccaaacgg ccagagcacc tgcgtatgaa tctatgacag agcaatgctt ttaatgaatt  1740
taaggcaaaa aaggtggaga gggagatgtg tgagcatcct gcaaggtgaa acgactcaaa  1800
atgacagttt cagagagtca atgtcattac atagaacact tcagacacag gaaaaataaa  1860
cgtggatttt aaaaaatcaa tcaatggtgc aaaaaaaaac ttaaagcaaa atagtattgc  1920
tgaactctta ggcacatcaa ttaattgatt cctcgcgaca tcttctcaac cttatcaagg  1980
attttcatgt tgatgactcg aaactgacag tattaagggt aggatgttgc ttctgaatca  2040
ctgttgagtt ctgattgtgt tgaagaaggg ttatcctttc attaggcaaa gtacaaaatt  2100
gcctataata cttgcaacta aggacaaatt agcatgcaag cttggtcaaa ctttttccag  2160
```

```
caaaatggaa gcaaagacaa aagaaactta ccaattgatg ttttacgtgc aaacaacctg  2220
aatctttttt ttatataaat atatattttt caaatagatt tttgattcag ctcattatga  2280
aaaacatccc aaactttaaa atgcgaaatt attggttggt gtgaagaaag ccagacaact  2340
tctgtttctt ctcttggtga aataataaaa tgcaaatgaa tcattgttaa ccacagctgt  2400
ggctcgtttg agggattggg gtggacctgg ggtttatttt cagtaaccca gctgcaatac  2460
ctgtctgtaa tatgagaaaa aaaaaatgaa tctatttaat catttctact tgcagtactg  2520
ctatgtgcta agcttaactg gaagccttgg aatgggcata agttgtatgt cctacatttc  2580
atcattgtcc cgggcctgca ttgcactgga aaaaaaaatc gccacctgtt cttacaccag  2640
tatttggttc aagacaccaa atgtcttcag cccatggctg aagaacaaca gaagagagtc  2700
aggataaaaa atacatactg tggtcggcaa ggtgagggag atagggatat ccaggggaag  2760
agggtgttgc tgtggcccac tctctgtcta atctctttac agcaaattgg taagattttc  2820
agttttactt ctttctactg tttctgctgt ctaccttcct tatatttttt tcctcaacag  2880
ttttaaaaag aaaaaaaggt ctattttttt ttctcctata cttgggctac attttttgat  2940
tgtaaaaata tttgatggcc ttttgatgaa tgtcttccac agtaaagaaa acttagtggc  3000
ttaatttagg aaacatgtta acaggacact atgtttttga aattgtaaca aaatctacat  3060
aaatgattta caggttaaaa gaataaaaat aaaggtaact ttacctttct taaatatttc  3120
ctgccttaaa gagagcattt ccatgacttt agctggtgaa agggtttaat atctgcagag  3180
ctttataaaa atatatttca gtgcatactg gtataataga tgatcatgca gttgcagttg  3240
agttgtatca cctttttttgt ttgtctttta taatgtcttc agtctgagtg tgcaaagtca  3300
atttgtaata ttttgcaacc ctaggatttt tttaaataga tgctgcttgc tatgttttca  3360
aacctttttg agccatagga tccaagccat aaaattcttt atgcatgttg aattcagtca  3420
gaaaagagca aggctttgct ttttgaaatt gcaactcaaa tgagatggga tgaaatccta  3480
tgacagtaag caaaaacaga accatgaaaa atgattggac atacaccttt tcaattgtgg  3540
caataattga aagaatcgat aaaagttcat ctttggacag aaagccttta aaaaaaaaat  3600
cactccctct tccccctcct cccttattgc agcagcctac tgagaacttt gactgttgct  3660
ggtaaattag aagctacaat aataattaag ggcagaaatt atacttaaaa agtgcagatc  3720
cttgttcttt gacaatttgt gatgtctgaa aaaacagaac ccgaaaagct atggtgatat  3780
gtacaggcat tatttcagac tgtaaatggc ttgtgatact cttgatactt gttttcaaat  3840
atgtttacta actgtagtgt tgactgcctg accaaattcc agtgaaactt atacaccaaa  3900
atattcttcc taggtcctat ttgctagtaa catgagcact gtgattggct ggctataacc  3960
accccagtta aaccattttc ataattagta gtgccagcaa tagtggcaaa cactgcaact  4020
tttctgcata aaaagcatta attgcacagc taccatccac acaaatacat agtttttctg  4080
acttcacatt tattaagtga aatttatttc ccatgctgtg gaaagtttat tgagaacttg  4140
tttcataaat ggatatccct actatgactg tgaaaacatg tcaagtgtca cattagtgtc  4200
acagacagaa agcacacacc tatgcaatat ggcttatcta tatttatttg taaaaatcca  4260
agcatagttt aaaatatgat gtcgatatta ctagtcttga gtttctaaga gggttcttta  4320
tgttatacca ggtaagtgta taaaagagat taagtgcttt tttttcatca cttgattatt  4380
ttctttaaaa tcagctatta caggatattt ttttatttta tacatgctgt tttttaatta  4440
aaatataatc actgaagttt actaatttga ttttataagg tttgtagcat tacagaataa  4500
ctaaactggg atttataaac cagctgtgat taacaatgta aagtattaat tattgaactt  4560
tgaaccagat ttttaggaaa attatgttct ttttcccccct ttatggtctt aactaatttg  4620
aatccttcaa gaaggatttt tccatactat tttttaagat agaagataat ttgtgggcag  4680
gggtggagga tgcatgtatg atactccata aattcaacat tctttactat aggtaatgaa  4740
tgattataaa caagatgcat cttagatagt attaatatac tgagccttgg attatatatt  4800
taatatagga cctattttga atattcagtt aatcatatgg ttcctagctt acaagggcta  4860
gatctaagat tattcccatg agaaatgttg aatttatgaa gaatagattt taaggctttg  4920
aaaatggtta atttctcaaa aacatcaatg tccaaacatc tacctttttt catagagagta  4980
gacactagca agctggacaa actatcacaa aagtatttgt cacacataac ctgtggtctg  5040
ttgctgatta atacagtact ttttcttgtg tgattcttaa cattatagca caagtattat  5100
ctcagtggat tatccggaat aacatctgaa agatgggttc atctatgttt gtgtttgctc  5160
tttaaactat tgtttctcct atcccaagtt cgctttgcat ctatcagtaa ataaaattct  5220
tcagctgcct tattaggagt gctatgaggg taacacctgt tctgcttttc atcttgtatt  5280
tagttgactg tattatttga tttcggattg aatgaatgta aatagaaatt aaatgcaaat  5340
ttgaatgaac ataaaaaaaa aaaaaaaa                                     5368

SEQ ID NO: 4           moltype = AA  length = 502
FEATURE                Location/Qualifiers
source                 1..502
                       mol_type = protein
                       organism = Homo sapiens
SEQUENCE: 4
MAGVFDIDLD QPEDAGSEDE LEEGGQLNES MDHGGVGPYE LGMEHCEKFE ISETSVNRGP  60
EKIRPECFEL LRVLGKGGYG KVFQVRKVTG ANTGKIFAMK VLKKAMIVRN AKDTAHTKAE  120
RNILEEVKHP FIVDLIYAFQ TGGKLYLILE YLSGGELFMQ LEREGIFMED TACFYLAEIS  180
MALGHLHQKG IIYRDLKPEN IMLNHQGHVK LTDFGLCKES IHDGTVTHTF CGTIEYMAPE  240
ILMRSGHNRA VDWWSLGALM YDMLTGAPPF TGENRKKTID KILKCKLNLP PYLTQEARDL  300
LKKLLKRNAA SRLGAGPGDA GEVQAHPFFR HINWEELLAR KVEPPFKPLL QSEEDVSQFD  360
SKFTRQTPVD SPDDSTLSES ANQVFLGFTY VAPSVLESVK EKFSFEPKIR SPRRFIGSPR  420
TPVSPVKFSP GDFWGRGASA STANPQTPVE YPMETSGIEQ MDVTMSGEAS APLPIRQPNS  480
GPYKKQAFPM ISKRPEHLRM NL                                           502

SEQ ID NO: 5           moltype = DNA  length = 829
FEATURE                Location/Qualifiers
source                 1..829
                       mol_type = unassigned DNA
                       organism = Homo sapiens
SEQUENCE: 5
cctcttttcc gtggcgcctc ggaggcgttc agctgcttca agatgaagct gaacatctcc  60
ttcccagcca ctggctgcca gaaactcatt gaagtggacg atgaacgcaa acttcgtact  120
```

-continued

```
ttctatgaga agcgtatggc cacagaagtt gctgctgacg ctctgggtga agaatggaag  180
ggttatgtgg tccgaatcag tggtgggaac gacaaacaag gtttccccat gaagcagggt  240
gtcttgaccc atggccgtgt ccgcctgcta ctgagtaagg ggcattcctg ttacagacca  300
aggagaactg gagaaagaaa gagaaaatca gttcgtggtt gcattgtgga tgcaaatctg  360
agcgttctca acttggttat tgtaaaaaaa ggagagaagg atattcctgg actgactgat  420
actacagtgc ctcgccgcct gggccccaaa agagctagca gaatccgcaa acttttcaat  480
ctctctaaag aagatgatgt ccgccagtat gttgtaagaa agcccttaaa taaagaaggt  540
aagaaaccta ggaccaaagc acccaagatt cagcgtcttg ttactccacg tgtcctgcag  600
cacaaacggc ggcgtattgc tctgaagaag cagcgtacca agaaaaataa agaagaggct  660
gcagaatatg ctaaactttt ggccaagaga atgaaggagg ctaaggagaa gcgccaggaa  720
caaattgcga agagacgcag actttcctct ctgcgagctt ctacttctaa gtctgaatcc  780
agtcagaaat aagatttttt gagtaacaaa taaataagat cagactctg              829
```

CALMODULIN INHIBITORS, CHK2 INHIBITORS AND RSK INHIBITORS FOR THE TREATMENT OF RIBOSOMAL DISORDERS AND RIBOSOMAPATHIES

CROSS-REFERENCE TO RELATED APPLICATIONS

The present application is a 371 National Phase Entry of International Patent Application No. PCT/US2017/041851 filed on Jul. 13, 2017 which claims benefit of and priority to U.S. Provisional Application No. 62/361,631, filed Jul. 13, 2016, entitled "CALMODULIN INHIBITORS, CHK2 INHIBITORS AND RSK INHIBITORS FOR THE TREATMENT OF RIBOSOMAL DISORDERS AND RIBOSOMAPATHIES," which are hereby incorporated by reference herein in their entirety.

GOVERNMENT SUPPORT

This invention was made with government support under Grant nos. HL 100001 and HL 134812, awarded by The National Institutes of Health. The government has certain rights in the invention.

SEQUENCE LISTING

The instant application contains a Sequence Listing which has been submitted electronically in XML format and is hereby incorporated by reference in its entirety. Said XML copy, created on Apr. 9, 2024, is named 701039-087701USD1_SL.xml and is 18,724 bytes in size.

FIELD OF THE INVENTION

The present invention relates generally to methods, compositions and kits for treatment of ribosomal disorders and ribosomopathies, e.g. Diamond Blackfan anaemia (DBA). In some embodiments, the invention relates to the use of novel classes of compounds, i.e. inhibitors of RSK (p90S6K); inhibitors of p70S6K; and inhibitors of rps6, to treat ribosomal disorders and ribosomopathies. In some embodiments, the invention relates to the use of specific Chk2 inhibitors as well as to the use of specific phenothiazine derivatives to treat ribosomal disorders and ribosomopathies, e.g. DBA.

BACKGROUND OF THE INVENTION

Diamond Blackfan anemia (DBA) is a congenital anemia that presents in children, often before one year of age (Vlachos et al., 2008). The primary symptom for these patients is a block in erythroid differentiation and possible defect in hematopoietic stem cells (HSCs), and some patients also have craniofacial anomalies. Ribosomal protein S19 (RPS19) was the first gene found mutated in DBA patients (Draptchinskaia et al., 1999). Sequencing of patient samples has identified mutations of either large (60 s) or small (40 s) subunit ribosomal proteins in over 50% of patients (Vlachos et al., 2010), most recently rps29. Patients are heterozygous for these mutations, always maintaining a wildtype copy of the affected ribosomal protein gene.

Ribosomal protein knockdown leads to an increase of free ribosomal proteins. Some ribosomal proteins, including RPL11 and RPL5, can prevent p53 degradation, as they are able to bind MDM2 and sequester it from p53 (Fumagalli et al, 2009). RPL26 has been shown to increase p53 protein by an alternative mechanism, as it can bind p53 mRNA, increasing its translation (Tagaki et al., 2005). p53 activation plays an important role in DBA pathogenesis, as well as in other diseases where ribosomal and related genes are mutated, now termed ribosomopathies. These include 5q-myelodysplastic syndrome, where one copy of RPS14 is lost. p53 activation is also a common feature in bone marrow failure disorders, such as Fanconi Anemia (Ceccaldi et al., 2012). In human CD34+ cells, RPS19 knockdown leads to p53 activation (Ebert et al., 2005; Flygare et al., 2005), with increased accumulation in erythroid cells. Differentiation defects can be rescued by p53 inhibition (Dutt et al., 2011). Mouse models of RPS19 mutation or knockdown have hematopoietic defects that can be rescued by p53 mutation (McGowan et al., 2008; Jaako et al., 2011). Rps19 has been targeted by morpholino in zebrafish embryos, and the hematopoietic defects in rpl11 mutant zebrafish are rescued by p53 knockdown (Danilova et al., 2008; Torihara et al., 2011; Danilova et al., 2011).

Ribosomal protein mutations are common in patients with Diamond Blackfan anemia (DBA), who have red cell aplasia and craniofacial abnormalities. The inventors have previously characterized zebrafish mutant rps29, a ribosomal protein in the small subunit, that have hematopoietic and endothelial defects (Taylor et al., 2012). Rps29−/− embryos have morphological defects in the head, as well as decreased hematopoietic stem cells, hemoglobin, and staining of endothelial markers. Consistent with other models of DBA, knockdown of p53 near completely rescues the rps29 mutant phenotype.

The inventors have previously demonstrated that Rps29−/− embryos have a defect in arterial specification, leading to decreased HSCs and decreased flk1 expression in the intersegmental vessels at 24 hours post fertilization (hpf). Primitive erythropoiesis is also affected, as rps29−/− embryos have less hemoglobin. These embryos also have increased apoptosis, particularly in the head, and die by five days post fertilization (dpf). p53 pathways are activated in the embryo, and p53 mutation rescues all hematopoietic and apoptotic phenotypes. Using this model system the inventors discovered that Calmodulin (CAM) inhibitors and $Ca2^+$ inhibitors can rescue the Rps29−/− phenotype and can be used to treat ribosomal disorders or ribosomopathy, e.g. Diamond Blackfan anemia (DBA) (See e.g. US publication 2015/0265627).

While significant progress is being made in the identification of compounds for treatment, current treatment options for treatment of ribosomal disorders or ribosomopathy, e.g. a mutation in a ribosomal protein, are far from optimal, especially for DBA. As such, it is still imperative to discover novel, effective, and targeted therapies for these diseases associated with a ribosomal disorder or ribosomopathy, e.g., a mutation in a ribosomal protein. In particular, there is a strong need in the art for improved methods for treatment of DBA with small-molecule drugs.

SUMMARY OF THE INVENTION

The present invention is generally directed to methods, compositions and kits for treatment of ribosomal disorders and ribosomapathies, e.g. Diamond Blackfan anemia (DBA). In some embodiments, the invention relates to the use of novel classes of compounds, i.e. inhibitors of RSK (p90S6K), e.g. SL and SK; and inhibitors of p70S6K, e.g. PF; and inhibitors of rps6, to treat ribosomal disorders and ribosomopathies. In some embodiments, the invention relates to the use of specific Chk2 inhibitors, e.g. CCT and III, for treatment of ribosomal disorders and ribosomapathies, e.g. DBA. In some embodiments, the invention relates to the use of specific phenothiazine derivatives, e.g. Perphenazine (PerSucc), or ACV, or 221E, or DB-4-088-2 (088-2), or DB-4-088-3 (088-3), or DB-4-086 (086), or DB-4-087-2 (087-2), or DB-4-087-3 (087-3), or DB-4-089 (089)) to treat ribosomal disorders and ribosomopathies, e.g. DBA.

In particular, the present invention is based, in part, upon the discovery that RSK signaling is upregulated in ribosomal protein deficient cells, e.g. RPA19 deficient cells. The inventors have discovered that RSK is activated upon RPS19 deficiency in $CD34^+$ cells and that inhibitors of RSK (p90s6K) as well as inhibitors of p70s6K increase hemoglobin (Hb) in rps29−/− zebrafish embryos, an in vivo model of ribosomal protein defect. The inventors have further determined that specific not previously disclosed inhibitors of Chk2 rescue the Hb in rps29−/− embryos, i.e. CCT and III.

In addition, the inventors have identified specific, not previously disclosed, phenothiazine derivatives such as ACV; 22E1; PerSucc; DB-4-088-2 (088-2); DB-4-088-3 (088-3); and DB-4-089 (089), which work particularly well at rescuing morphological defects and hematopoietic and endothelial defects in rps29−/− zebrafish embryos. Phenothiazine derivative DB-4-088-2 (088-2) advantageously did not change behavior of zebrafish in a behavior screen, and phenothiazine derivative DB-4-089 increased Hb at low concentrations as well as increased erythroid differentiation. The phenothiazine derivative compounds DB-4-083 (083); DB-4-084 (084); and DB-4-086 (086) did not increase Hb at the same low concentrations as DB-4-089.

In certain embodiments, the phenothiazine compound to treat ribosomal disorders and ribosomopathies, e.g. DBA, is a compound of Formula (I):

FORMULA (I)

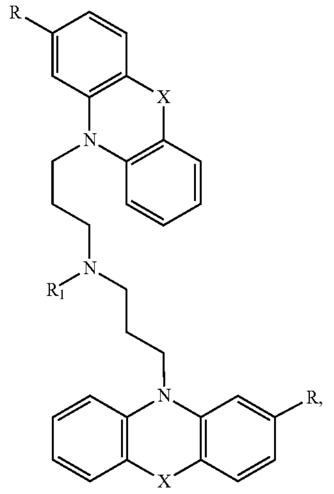

wherein:

X is O or S;

$R^1$ is H, alkyl, alkenyl, alkynyl, cyclyl, heterocyclyls, acyl, aryl, heteroaryl, alkylheteroaryl or alkylaryl;

each R is independently H, halo, alkyl, alkyl, alkenyl, alkynyl, haloalkyl, CN, OH, $NH_2$, alkylamino, dialkylamino, $CO_2H$, acyl, SH, thioalkoxy, $SO_2H$, or $SO_3H$; and isomers and pharmaceutically acceptable salts thereof.

See section herein entitled phenothiazine compounds.

In some embodiments, the phenothiazine compound to treat ribosomal disorders and ribosomopathies, e.g. DBA, is a compound of Formula II:

FORMULA (II)

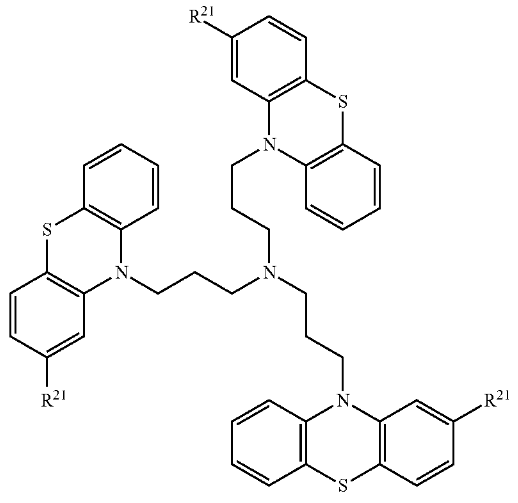

wherein:

each $R^{21}$ is independently selected from the group consisting of H, halo, alkyl, haloalkyl, CN, OH, $NH_2$, alkylamino, dialkylamino, $CO_2H$, acyl, SH, thioalkoxy, $SO_2H$, and $SO_3H$;

isomers and pharmaceutically acceptable salts thereof.

See section herein entitled phenothiazine compounds.

In one embodiment, the phenothiazine compound to treat ribosomal disorders and ribosomopathies, e.g. DBA, is the compound of structure:

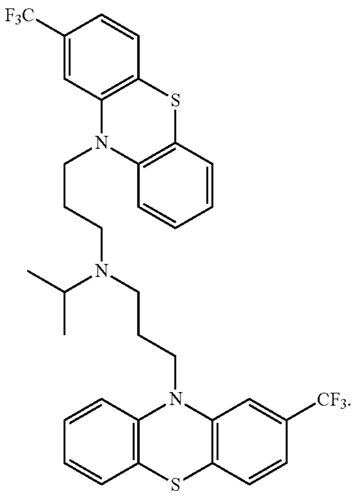 [SMILES: CC(C)N(CCCN1c2ccccc2Sc2ccc(C(F)(F)F)cc21)CCCN1c2ccccc2Sc2ccc(C(F)(F)F)cc21]

Thus, inhibitors of RSK signaling, e.g. inhibitors of RSK p90s6K and p70s6K, inhibitors of rsp6, as well as the specific phenothiazine derivatives and (CaM) inhibitor compounds disclosed herein (e.g. BABTA) can be used in a method for treatment of subjects with ribosomal protein disorders or ribosomopathies, e.g. Diamond Blackfan anemia (DBA) and other ribosomopathies, such as myelodysplasia, including 5q-myelodysplasia, Shwachman-Diamond syndrome and Treacher Collins Syndrome in human subjects.

Accordingly, one aspect of the present invention relates to a method of treating a subject with a ribosomal disorder or ribosomopathy, comprising administering an effective amount of an inhibitor of RSK (p90S6k) to the subject to decrease RSK (p90s6K) activity and decrease active p53 in at least one of CD34+ cells, erythroid cells or erythroid differentiated cells in the subject. In one embodiment, the inhibitor of p90S6k inhibits a variant selected from the group consisting of RSK1, RSK2 and RSK3. In one embodiment, the inhibitor of p90s6K selectively inhibits RSK2. Any inhibitor p90s6K is useful in methods of the invention, e.g. the inhibitor may be a nucleic acid (e.g. DNA or RNA, such as RNAi or shRNA, etc.), or a small molecule compound, or a protein, e.g. a peptide or antibody, or fragment of an antibody. In one embodiment, the inhibitor of p90S6k is a compound selected from the group consisting of: SL0101 (SL) or a derivative or analogue of SL; BI-D1870 (BI), or a derivative or analogue of BI; or SK, or a derivative or analogue of the compound.

In another aspect of the invention, a method of treating a subject with a ribosomal disorder or ribosomopathy is provided, the method comprises administering an effective amount of an inhibitor of p70S6K to the subject to decrease p70S6K activity and decrease active p53 in at least one of CD34+ cells, erythroid cells or erythroid differentiated cells in the subject. Any inhibitor p70S6K is useful in methods of the invention, e.g. the inhibitor can be a nucleic acid (e.g. DNA or RNA such as RNAi, or shRNA, etc.), or can be small molecule compound, or a protein, e.g. a peptide or antibody, or fragment thereof. In one embodiment the inhibitor of p70S6k is the compound PF-4708671 (PF), or a derivative or analogue of the compound.

In another aspect, a method of treating a subject with a ribosomal disorder or ribosomopathy is provided, the method comprises administering an effective amount of an inhibitor of Chk2 to the subject to decrease active p53 in at least one of CD34+ cells, erythroid cells or erythroid differentiated cells in the subject, wherein the inhibitor of Chk2 comprises a compound selected from the group consisting of CCT and III, or derivatives thereof.

In still another aspect, a method of treating a subject with a ribosomal disorder or ribosomopathy is provided that comprises administering an effective amount of an inhibitor of calmodulin to the subject to decrease active p53 in at least one of CD34+ cells, erythroid cells or erythroid differentiated cells in the subject, wherein the inhibitor of calmodulin is a phenothiazine compound, or a derivative or analogue of the phenothiazine compound, wherein the phenothiazine compound is selected from the group consisting of ACV-1-235 (ACV); JJM-II-221E (221E); and DB1026 (PerSucc) DB-4-088-2 (088-2); DB-4-088-3 (088-3); DB-4-086 (086); DB-4-087-2 (087-2); DB-4-087-3 (087-3); DB-4-089 (089), or a compound of Formula I or Formula II.

Another aspect provided, is a method of treating a subject with a ribosomal disorder or ribosomopathy, comprising administering an effective amount of a calcium channel blocker BAPTA-AM or derivative or analogue thereof to the subject to decrease active p53 in at least one of CD34+ cells.

In some embodiments of all aspects of the present invention, the method comprises treating a subject with a ribosomal disorder where the subject has Diamond Blackfan Anemia (DBA) or inherited erythroblastopenia, for example, where the subject has DBA1, DBA2, DBA3, DBA4, DBA5, DBA6, DBA7, or DBA8. In some embodiments, a subject with a ribosomal disorder has a mutation in ribosomal protein 19 (RPS19). In alternative embodiments, a subject with a ribosomal disorder has a mutation in ribosomal protein from at least one of, but not limited to RPS7, RPS10, RPS19, RPS24, PRS26, RPS17, PRS27L RPS29, RPL35A, PRL5 and PPL11.

In some embodiments, a subject with a ribosomal disorder has a mutation in a ribosomal protein selected from the group consisting of: rPL2A, rPL2B, rPL3, rpL4A, rPL4B, rPL7A, rPL7B, rPL10, rPL11, rPL16A, rPL17A, rPL17B, rPL18A, rPL18B, Rpl19A, rPL19, rPL25, rPL29, rpL31A, rpL31B, rPL36A, rPL40A, rPS1A, rPS6A, rPS6B, rPS14A, rPS15, rPS19, rPS23B, rPS25A, rPS26B, rPS29, rPS29B and rPS31.

In some embodiments of all aspects of the present invention, the method further comprises administering another therapeutic agent to treat the ribosomal protein defect, selected from the group consisting of: corticosteroids, blood transfusions and other treatments known to persons of ordinary skill in the art.

In some embodiments of all aspects of the present invention, the inhibitor administered to the subject increases the number of CD71+ erythroid cells in the subject and/or increases hemoglobin levels in the subject.

In some embodiments of all aspects of the present invention, the methods and inhibitors disclosed herein can be used to treat a subject with a ribosomal disorder, such as DBA has a symptom of macrocytic anemia and/or craniofacial abnormalities.

In some embodiments of all aspects of the present invention, the methods and inhibitors and inhibitors disclosed herein can be used to treat a subject with a ribosomopathy such as 5q-myelodysplasia, for example, where the subject has a mutation in Rps14 or decrease in Rps14 expression. In some embodiments, a subject with 5q-myelodysplasia has dysplastic bone marrow.

In some embodiments of all aspects of the present invention, the methods and inhibitors as disclosed herein can be used to treat a subject with a ribosomopathy such as Shwachman-Diamond syndrome, for example, where the subject has a mutation in Sbds. In some embodiments, a subject with Shwachman-Diamond syndrome has one or more symptoms selected from pancreatic insufficiency, bone marrow dysfunction, skeletal deformities.

In some embodiments of all aspects of the present invention, the methods and inhibitors as disclosed herein can be used to treat a subject with a ribosomopathy such as Treacher Collins Syndrome, for example, where the subject has a mutation in TCOF1 (nucleolar). In some embodiments, a subject with Treacher Collins Syndrome has one or more craniofacial deformities.

In some embodiments the present invention also provides kits comprising compositions comprising the inhibitors as disclosed herein for the use in the methods to treat a subject with a ribosomal protein disorder or disease or ribosomopathy as disclosed herein.

BRIEF DESCRIPTION OF THE DRAWINGS

FIG. 2 is a chart that shows the additional ribosomopathies, the most common being 5q-subtype of MDS. Any drug that we find that works in our DBA models would also help patients with other ribosomopathies.

FIG. 4A shows that zebrafish with a mutation in rps29 have decreased expression of cmyb (hematopoietic marker), flk1 (endothelial vessel marker) and are anemic, shown by lack of benzidine staining (which stains for hemoglobin (Hb)). These ribosomal protein fish model DBA. (Taylor, A. M., et al. (2012). Exp. Hematol. 40, 228-237. e5., Mirabello, L., et al. (2014). Blood 124, 24-32.). FIG. 4B shows zebrafish photos of rescued phenotype. Consistent with other animal models of DBA, crossing the rps29 mutant with a p53 mutant rescues these phenotypes, showing hematopoietic and endothelial defects are mediated through p53.

FIGS. 5A and 5B show zebrafish photos and structures of novel compounds that can rescue the Hb defect in our DBA model, specific Chk2 inhibitors, CCT and III, can rescue Hb in fish. FIG. 5A zebra fish photos of A-3, W-7, CCT and III rescue. FIG. 5B chemical structures of TFP, A-3, W-7, CCT and III compounds that were identified by the chemical screen to rescue Hb in rps 29−/− embryos.

FIG. 7A schematic, cord blood derived $CD34^+$ cells were expanded in culture for 4 days and then infected with a lentivirus that contains a hairpin against RPS19 or Luciferase as a control. After 3 days of selection, cells were moved to erythroid differentiation media and incubated with drugs until day 12. Cells were then harvested for Flow cytometry analysis and RNA. On day 12, RPS19 deficient cells have only 40% erythroid precursor cells, while our control cells have 70%. FIG. 7B, % erythroid precursor cells on day 12 after TFP treatment. Treating with TFP increases the percentages of CD71+ cells. RPS19 deficiency increases p21 mRNA levels. FIG. 7C is a graph of p21 levels after TFP treatment. Treatment with TFP dose dependently decreases p21 mRNA. We also see this with our Chk2 inhibitors (data not shown). Accordingly, CAM inhibitors rescue human in vitro model of DBA and reduce p53 target gene expression.

FIG. 8B, graph of p21 mRNA Levels. Using p21 mRNA levels for a measure of p53 activity in the marrow of the mice, Rps19 deficient mice have increased p21 mRNA levels. Treating mice with TFP decreases the level of p21 mRNA in the mice. FIG. 8C, graph of red blood cell number. FIG. 8D, graph of Hemoglobin levels. Treating RPS19 deficient mice with TFP significantly increases Red blood cell number and Hemoglobin levels. Thus compounds found in a zebrafish chemical screen were able to rescue a human in vitro and mammalian in vivo model of DBA.

FIG. 9A a schematic of wild type P53 and deleted regulatory region p53 (p53 reg). FIG. 9B Schematic of procedure. Saos2 cells (p53-null cells) transiently transfected with p53 constructs and were treated with vehicle or 20 μM TFP for 24 hours. TFP activity on p53 was assessed by the ability of TFP to reduce p21 mRNA levels measured by qPCR. FIG. 9C is a graph of p21 RNA expression. Since our compound decreases p53 activity, we wanted to determine the region of p53 is responsible for CaM inhibitor activity. Mutation of the nuclear localization sequence had no effect on TFP activity and TFP did not inhibit the ability of p53 to form a tetramer. Next, the c-terminal 30 amino acids from p53 (363-393) were removed. This construct is p53-reg. We found that the regulatory region (REG) of p53 is required for TFP activity.

FIG. 10A is a schematic of conserved regulatory region phosphorylation sites. FIG. 10B are graphs of an unbiased mass spectrometry analysis looking for post-translational modifications of p53 altered in the presence of the CaM inhibitor TFP or the Chk2 inhibitor, BML. 293T cells were transfected with WT-p53 tagged with GFP and treated with TFP or BML for 3 hours. P53 was immunoprecipitated using an antibody against GFP and was submitted for mass spec analysis. Surprisingly, only 1 residue was found to be differentially phosphorylated in the presence of TFP and BML. By two different mass spec methods, either conventional mass spec or by TMT tagging of the peptide we found in both cases the percentage of peptides containing phosphorylated serine 392 was reduced in TFP and BML treated samples (FIG. 10B). It was also noted that this serine is conserved in both zebrafish and mouse (FIG. 10A). FIG. 10C is a Western Blot that indicates phosphorylation decrease. Serine 6 and Serine 315 were identified to be phosphorylated, but the percentage of peptides containing these phosphorylations did not change with TFP or BML treatment.

FIG. 11A is a schematic of experiment used to test these mutants, we transiently transfected, WT p53, S15D and S392D into Saos2 cells and treated them with vehicle or TFP. To assess p53 activity, we examined p21 and MDM2 mRNA levels. FIG. 11B is a graph of p21 Expression. FIG. 11C is a graph of MDM2 mRNA expression. In cells that contain WT p53 or S15D p53, TFP was able to reduce p21 and MDM2 levels. However, in cells that contained p53 S392D, TFP was unable to reduce p21 or MDM2 levels. Confirming that blocking the S392 phosphorylation is important for the activity of TFP.

However the inhibitors for these kinases did not rescue Hb in rps29−/− fish. Thus, the question became what is TFP inhibiting upstream? Is it inhibiting a kinase that phosphorylates S392? We submitted CaM and Chk2 inhibitors for Kinase profiling using Thermo Fisher's SelectScreen. Through screening 100 kinases, we found that multiple CaM and Chk2 inhibitors blocked the activity of multiple kinases in the ribosomal s6 protein kinase family both p70S6K and p90S6K (RSK)s.

Figure 13:
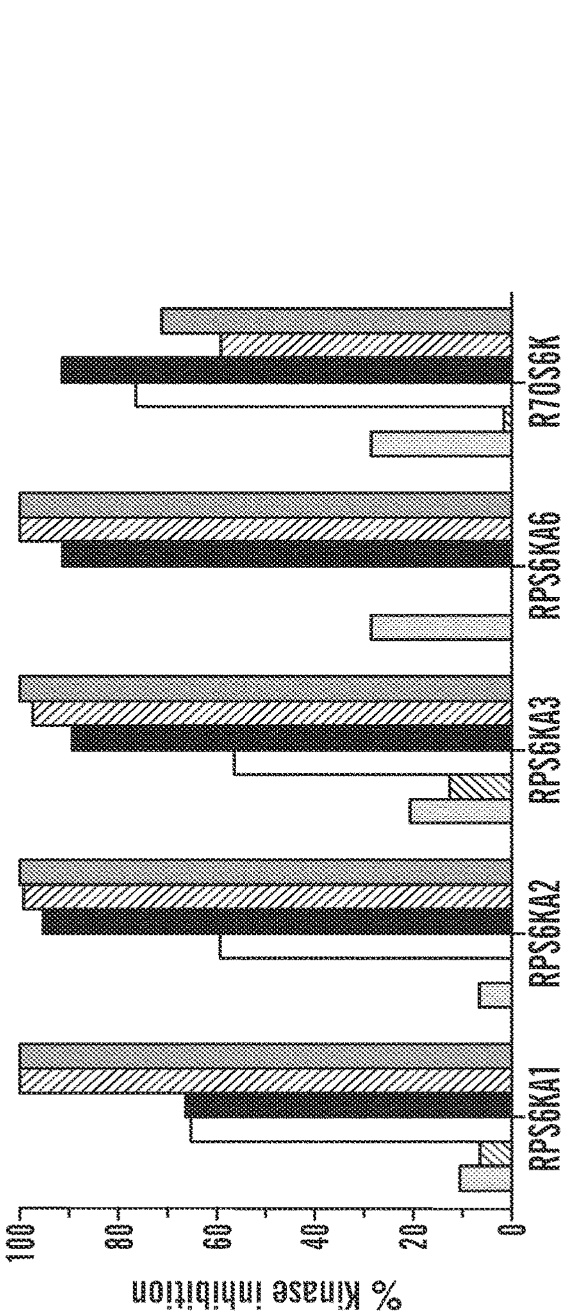

FIG. 13 shows a graph of percent inhibition of the in vitro kinase activity of CaM and Chk2 inhibitors on members of the RSK family, RSk1 (p90S6K), RSK 2 (p90S6K), RSK3 (p90S6K), RSK4, (p90S6K) and p70S6K.

Figure 14:
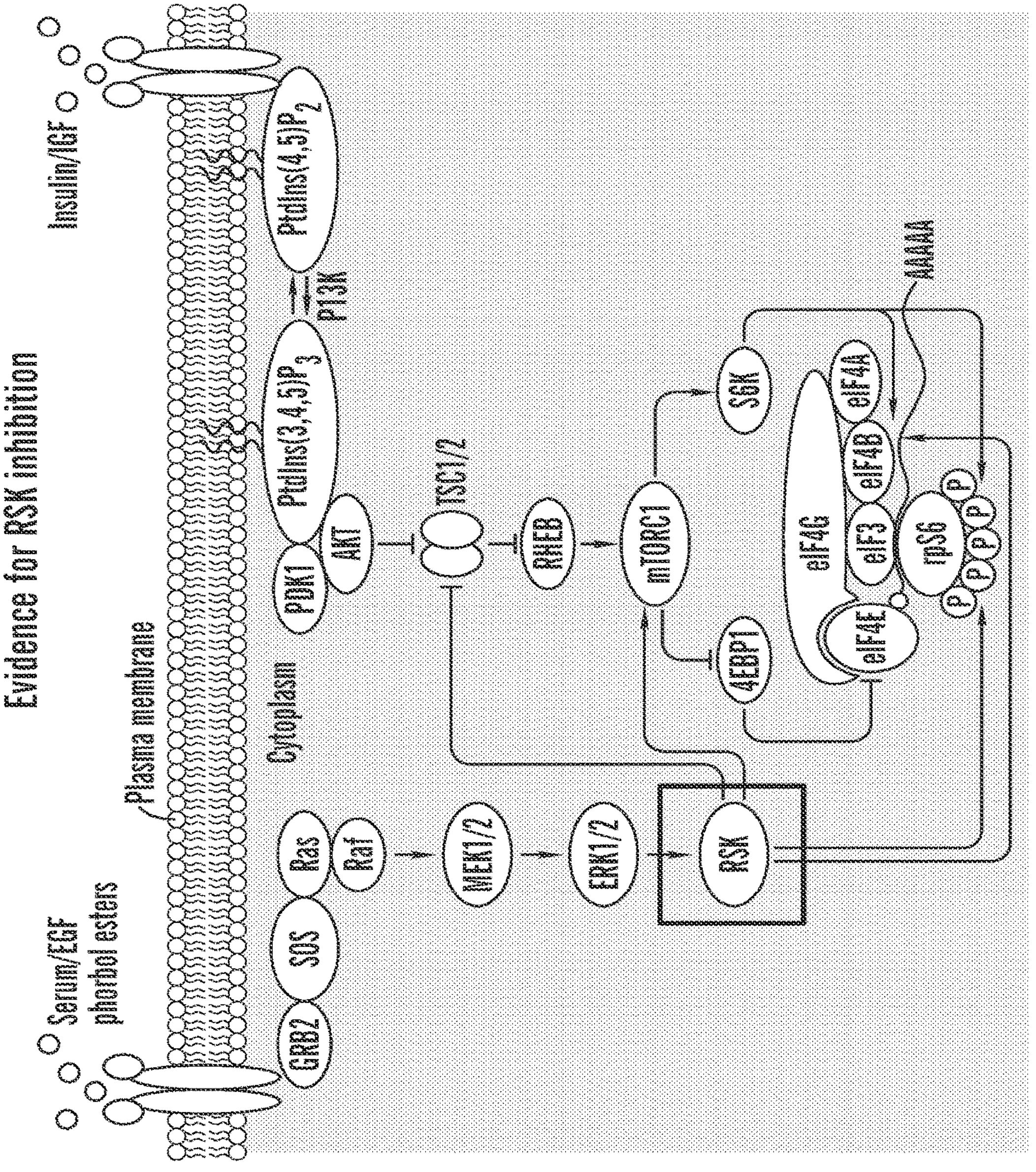

FIG. 14 is a schematic that shows literature evidence for CaM playing a role in translation and RSK pathway. The following literature is cited: RSK inhibitors were found in a screen of 23K shRNAs for p53 inhibitors that reduce p53 activity (p21 levels) but not protein levels Berns, K. et al. (2004). *Nature* 428, 431-437; Increased Calcium or ionomycin treatment causes sustained RSK activation Chuderland, D., Marmor, G., Shainskaya, A., and Seger, R. (2008). *J. Biol. Chem.* 283, 11176-11188; AA acids activate mTOR through Ca/CaM signaling Gulati, P. et al. (2008). *Cell Metabolism* 7, 456-465; RSK2 and 3 are elevated in rps29$^{-/-}$ microarray compared to WT/HET and p70S6K, downstream of mTOR and RSK, can phosphorylate p53 S392 Ci, Y. et al. (2014). *Cell Death and Disease* 5, e1542-10. We hypothesized that RP deficiency increases RSK signaling and CaM and Chk2 inhibitors are blocking downstream signaling from RSK and asked if RSK activity increased during ribosomal protein deficiency.

Figures 15A, 15B:
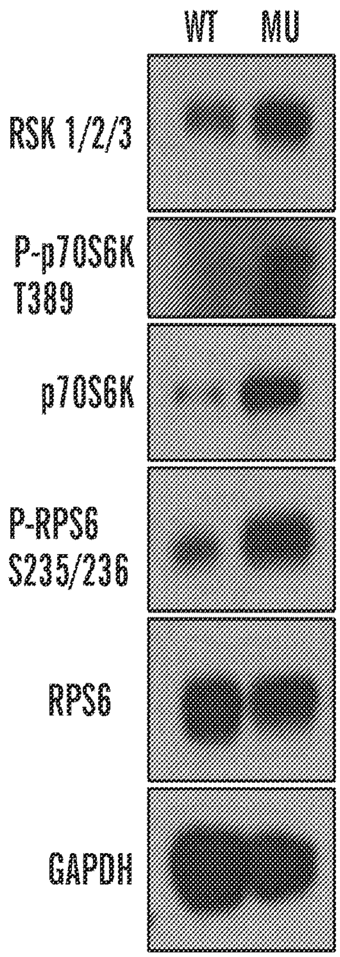

FIGS. 15A to 15B are gels and charts that indicate that Rps29−/− embryos have increased levels or RSK (p90S6k), p70s6K and RPS6 compared to rps29+/+ embryos. (phospho-RSK antibody does not work in zebrafish). FIG. 15A gel of embryo lysates. Whole embryos were lysed in RIPA buffer and run on a 10% SDS-PAGE gel. Lane 1. WT=WT/rps29$^{+/-}$ 48 hpf embryo lysates. Lane 2. MU=rps29$^{-/-}$ 48 hpf embryo lysates. FIG. 15B, a microarray comparing WT and rps29−/− embryos at 24 hpf, RSK2 was identified as a top differentially expressed gene, with a mean fold change value of 1.6-fold over WT embryos. Mean fold change values for p53 and MDM2, which are known to be high during rps deficiency, are included for comparison.

Figure 16A:
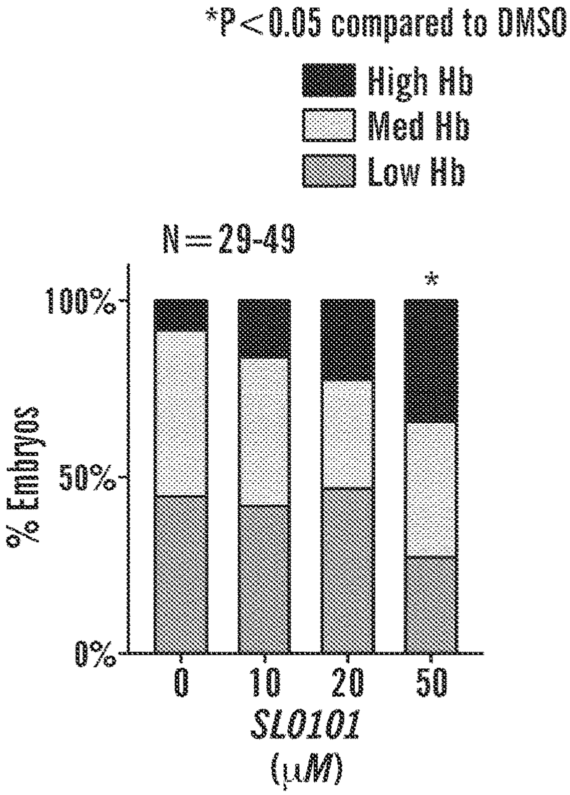
Figure 16B:
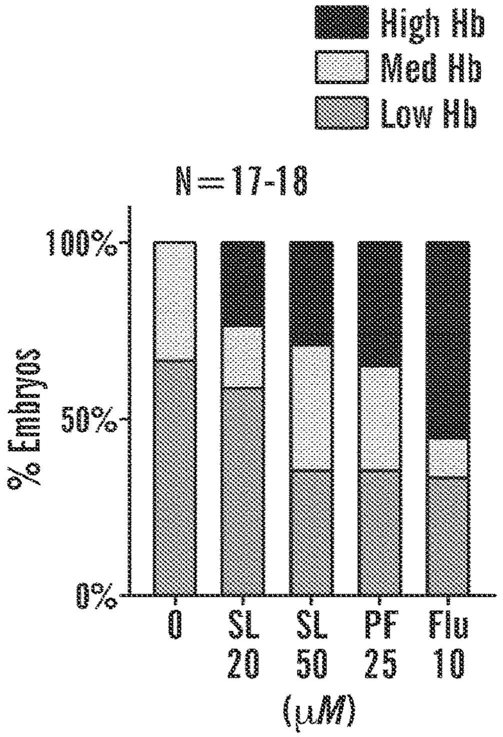
Figure 16C:
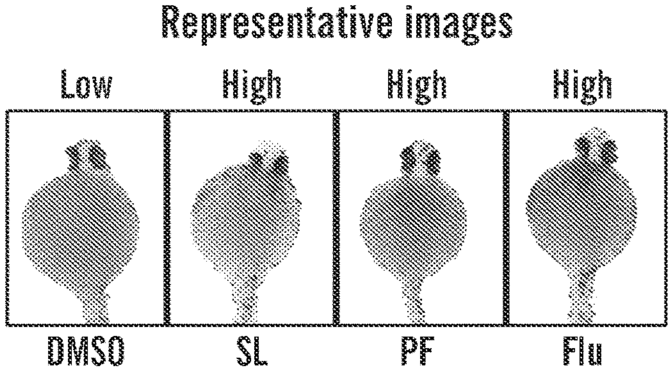

FIGS. 16A to 16C inhibitors of RSK and p70S6K increase Hb in rps29−/− embryos. FIG. 16A bar graph of Hb levels % embryos vs. SL1010. FIG. 16B bar graph of Hb levels % embryos vs. SL1010. FIG. 16C representative zebra fish images; SL=RSK inhibitor, PF=p70S6K inhibitor, FLU=CaM inhibitor. The CaM inhibitor, fluphenazine (FLU), rescues better than either RSK or p70S6K inhibitor alone.

Figure 17A:
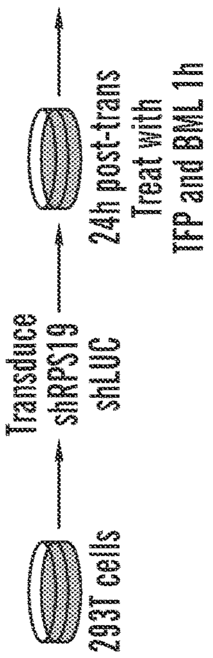
Figure 17B:
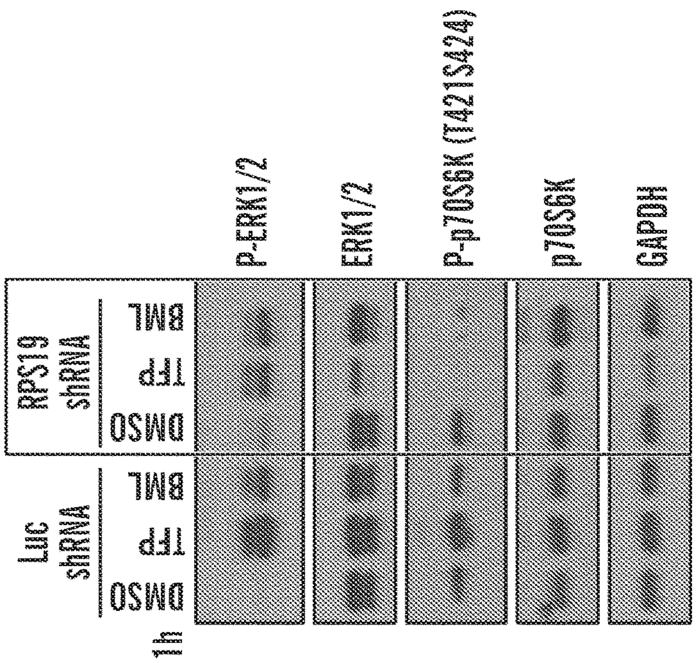
Figure 17C:
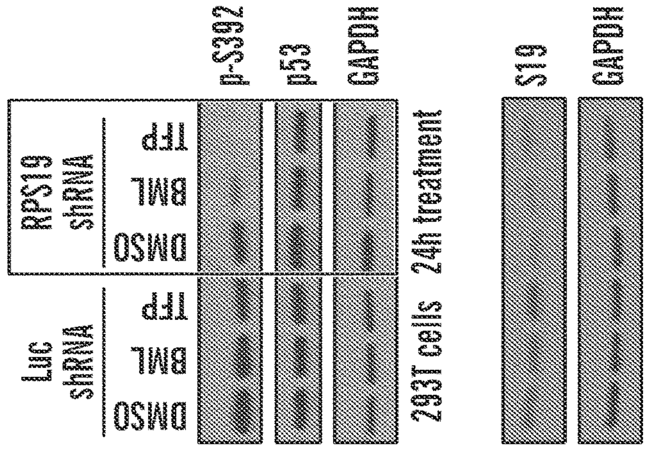

FIGS. 17A to 17C are schematics and gels that indicate CaM and Chk2 inhibitors block phosphorylation of p70S6K selectively during RP deficiency. FIG. 17A schematic, we used 293T cells, and induced ribosomal protein deficiency using shRNA for RPS19 or Luc for control. FIG. 17B a gel indicating that the phosphorylation of p70S6K is selectively inhibited by TFP and BML during ribosomal protein deficiency. ERK phosphorylation is increased by these inhibitors, which is also seen with RSK inhibitors. FIG. 17C a gel of the effect of Luc and RPS10 shRNA on phosphorylated S392. CaM and Chk2 inhibitors inhibit the ribosomal s6 kinase family in human cells. RSK inhibitors increase ERK phosphorylation through a negative feedback loop. So TFP and BML similarly affect ERK in the same manner.

Figure 18:
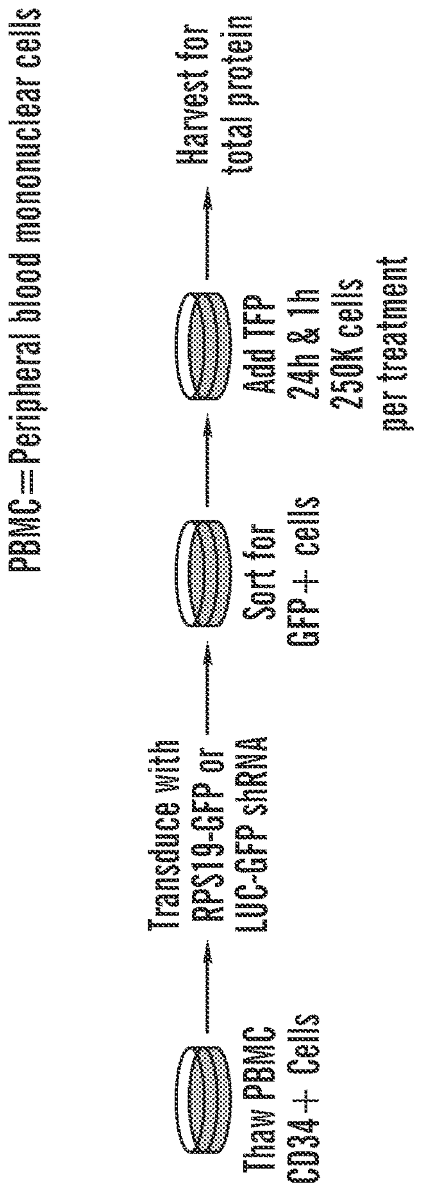

FIG. 18 is a schematic of the assay of RSK activation in human cells. The most relevant in vitro model in the blood field is primary human cells—such as Peripheral blood mononuclear cells (PBMCs).

Figure 19A:
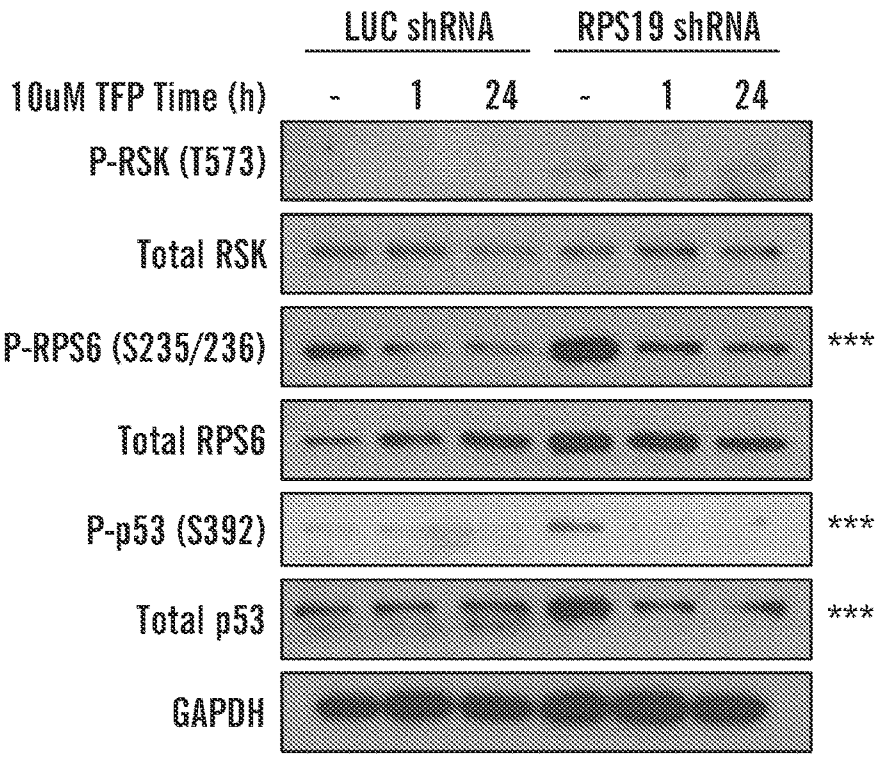
Figure 19B:
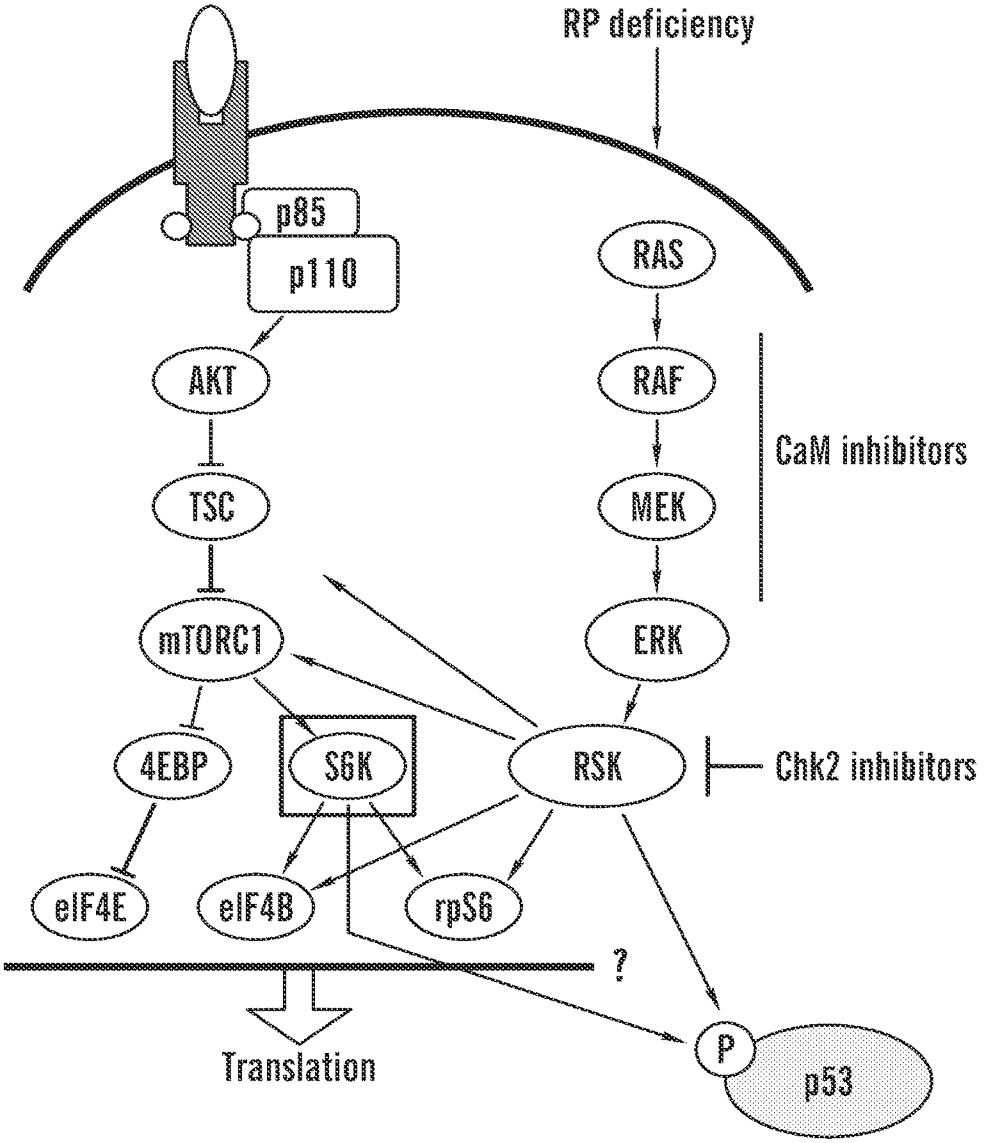

FIGS. 19A to 19B shows that RSk is activated upon RPS19 deficiency in CD34 cells. FIG. 19A gel of phosphorylation showing the results from TFP treatment of RPS 19 deficient CD34 cells, indicates that RSK is activated and RPS6 phosphorylation is increased in RPS19 knockdown cells. FIG. 19B schematic ov RP deficiency. TFP treatment reduces P-RPS6 and P-p53 S392 and p53 total levels.

Figure 20:
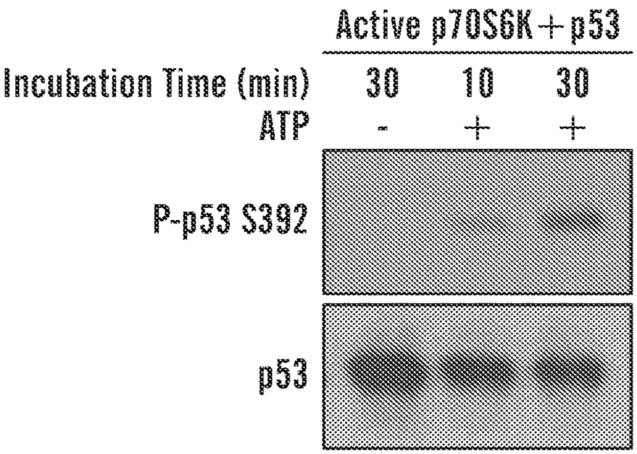

FIG. 20 is a gel that shows p-70S6K directly phosphorylates p53 at S392 within 10 minutes. Using recombinant active p70S6K or RSK and combining it with recombinant p53 and ATP, we see that only p70S6K can phosphorylate p53 at S392. RSK did not phosphorylate p53 after 30 minutes of incubation with ATP. S15, S20 and S315 are not phosphorylated by p70S6K and RSK1/2/3/ does not phosphorylate p53 in the same conditions (data not shown).

Figure 21:
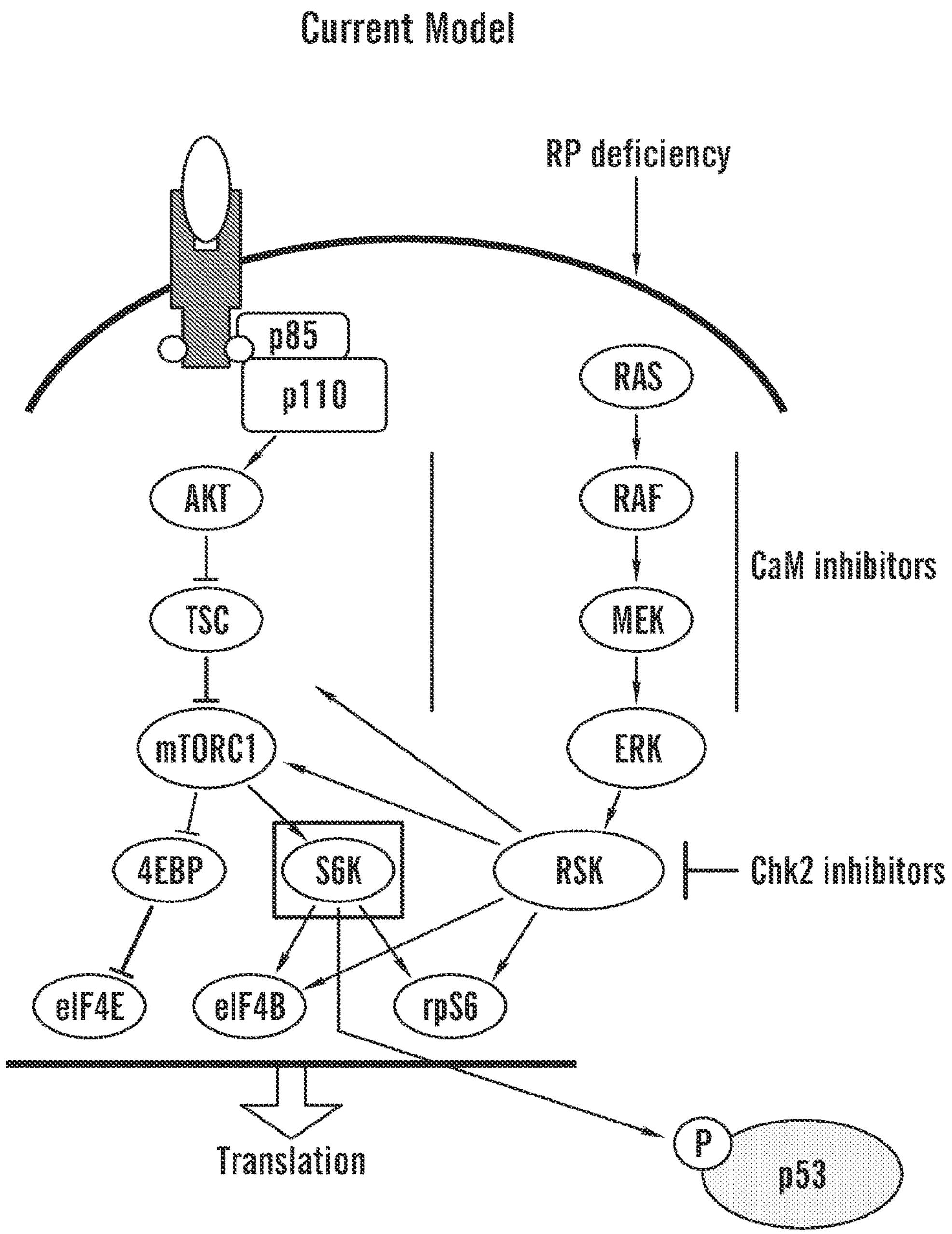

FIG. 21 is a schematic of our current model: During RP deficiency, there are not enough functional ribosomes and not enough translation. The cell is trying to upregulate translation (especially in RBCs when they need to make a lot of globin). To compensate, the RSK axis is much more active during RP deficiency, in an effort to get more translation. Calcium needs CaM to activate many kinases and for signaling for both the mTOR axis and the RSK axis. Not to be bound by theory, we propose that CaM inhibitors are inhibiting these kinases by binding up the available CaM and thus blocking the signaling. Chk2 inhibitors are working directly on inhibiting RSK and p70S6K (shown through our in vitro kinase profiling).

Figure 22B:
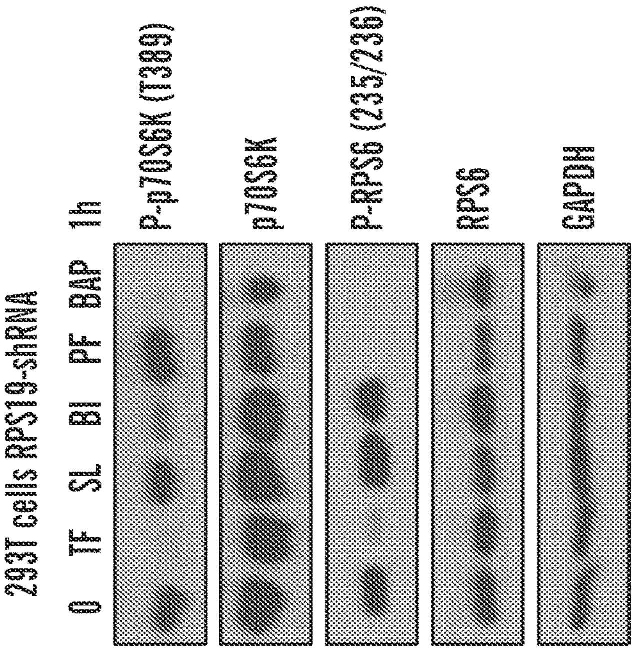
Figure 22A:
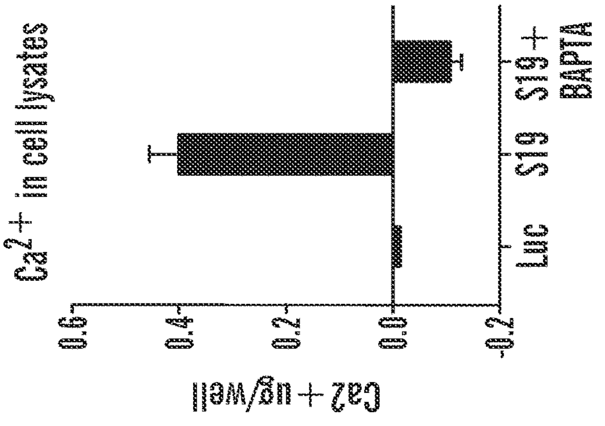

FIGS. 22A and 22B show a graph and gel that indicates that indicate intracellular $Ca^{2+}$ levels are increased in RP deficient cells and chelation reduces p70S6K and RS6 phosphorylation. Not all CaM inhibitors directly inhibited RSK or p70S6K in our in vitro kinase profiling. We hypothesize that the CaM inhibition is indirect, CaM is needed for calcium signaling. FIG. 22A, a graph of calcium in cell lysates using a colormetric calcium detection kit we measured the amount of calcium in cellular lysates and found that cells that had RPS19 knocked down had increased levels of calcium and treating those lysates with a calcium chelator, BAPTA-AM, was able to reduce the calcium levels. FIG. 22B is a gel of phosphorylation, we show that chelating calcium in cells reduces p70S6K and RPS6 phosphorylation, similar to our CaM inhibitors (TF). RSK inhibitor: SL and B1. P70s6K inhibitor: PF. In Summary we show: 1) CaM and Chk2 inhibitors reduce S392 phosphorylation of p53—to a much greater extent during ribosomal protein deficiency 2) CaM and Chk2 inhibitors also decrease P-p70S6K to a much greater extent during RP deficiency 3) p70S6K can directly phosphorylate p53 S392 in vitro 4) Total protein levels of RSK, p70S6K and rps6 are increased ruing RP deficiency in vitro and in vivo 5) RSK2 is increased in our microarray in rps20−/− vs WT 24 hpf embryos. Protein validates this upregulation 6) Calcium levels are increased during RP deficiency 7) Blocking the CaM-Calcium signaling (CaM inhibitors) or directly inhibiting RSK or p70S6K (Chk2 inhibitors) leads to a decrease in P-p53 and p53 activity. Reduced p53 activity leads to fewer RBCs undergoing apoptosis, alleviating the anemia.

Figure 23:
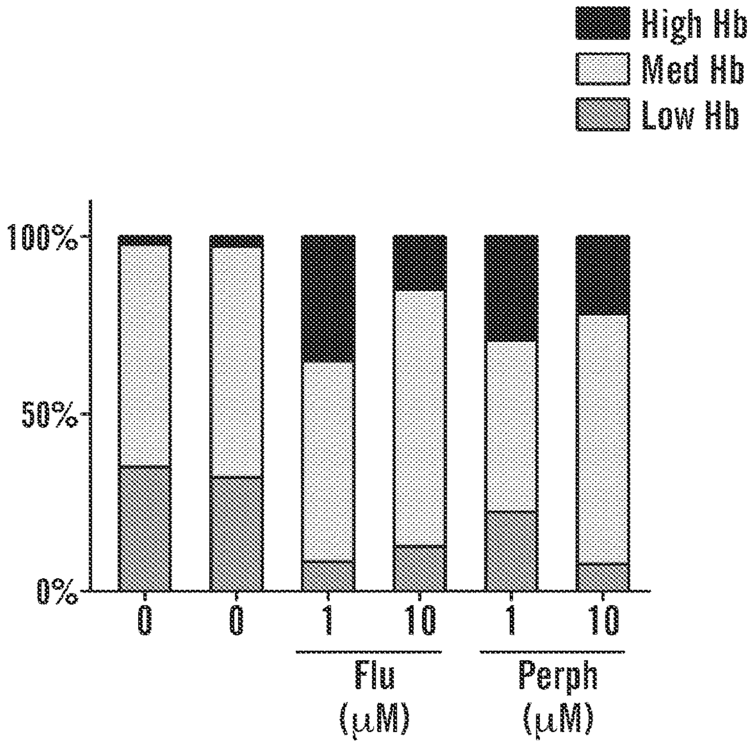
Figure 24:
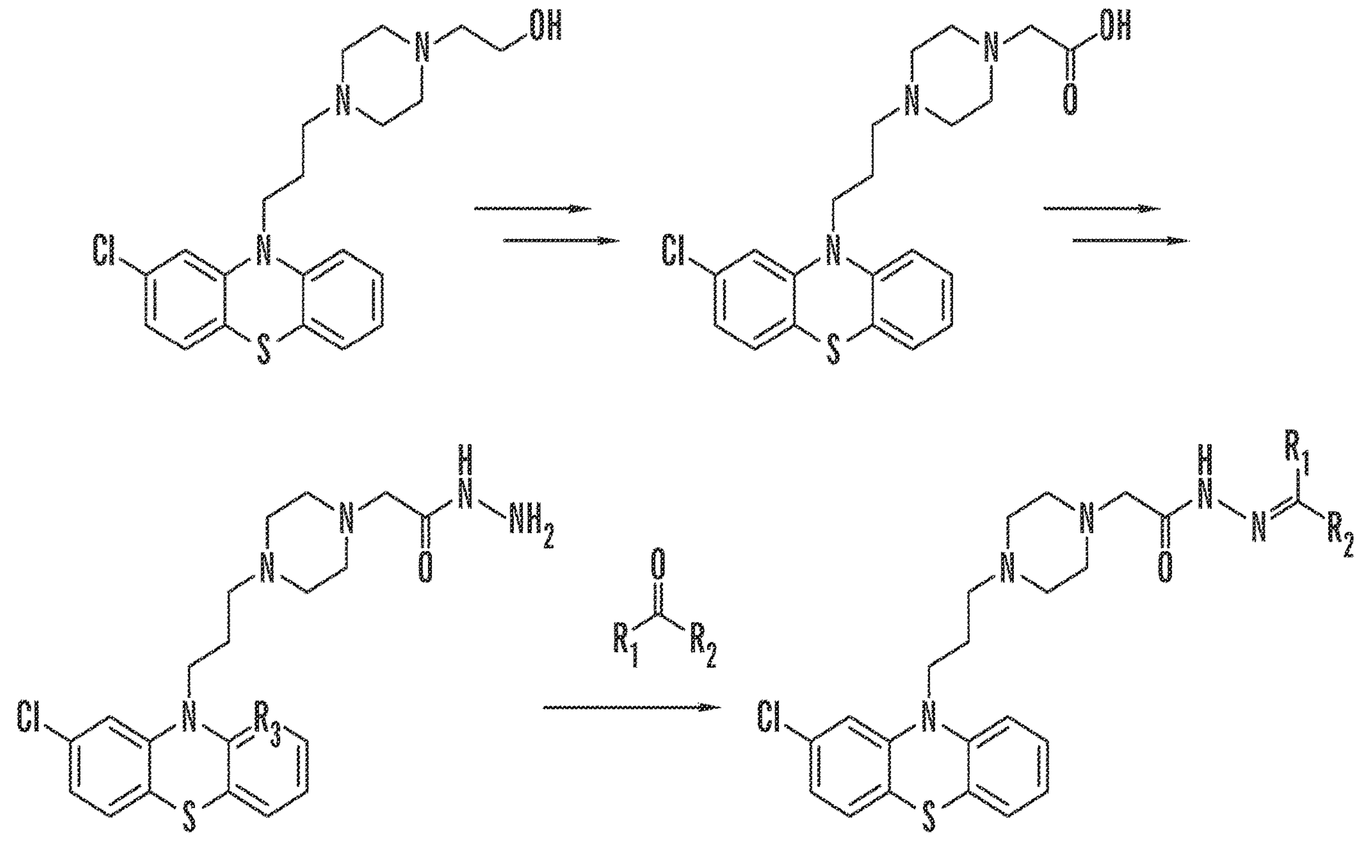
Figure 24:
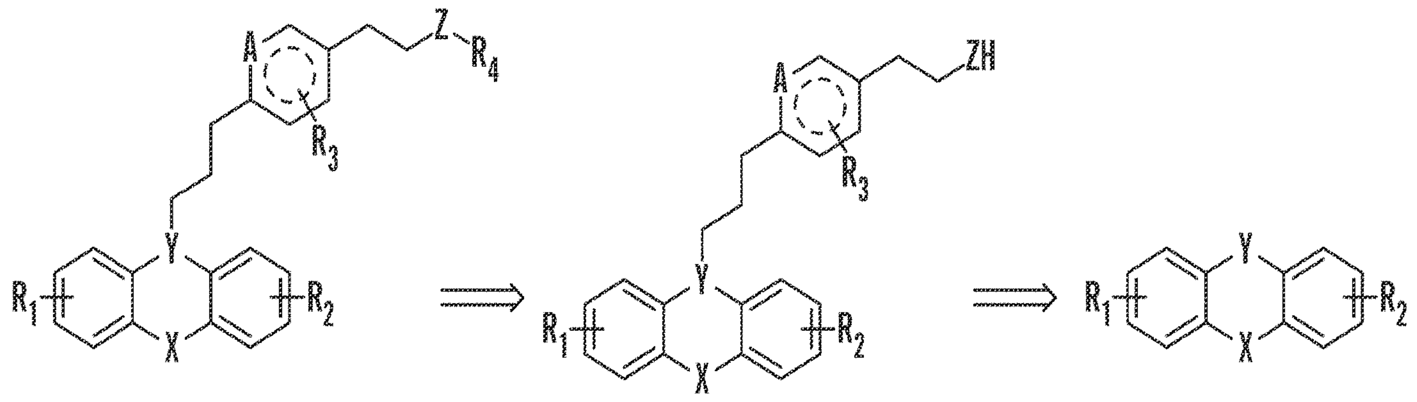
Figure 25A:
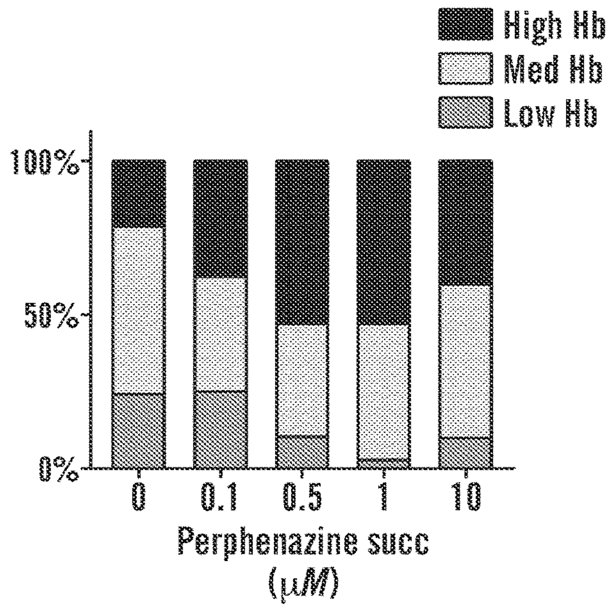
Figure 25B:
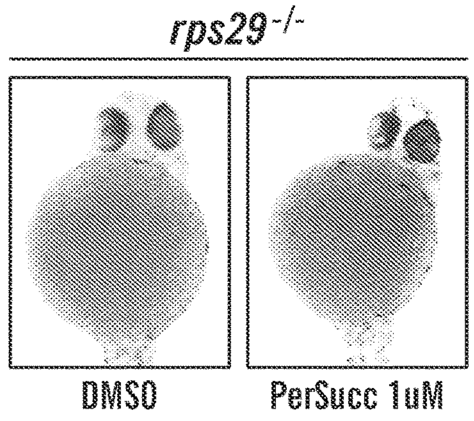
Figure 25C:
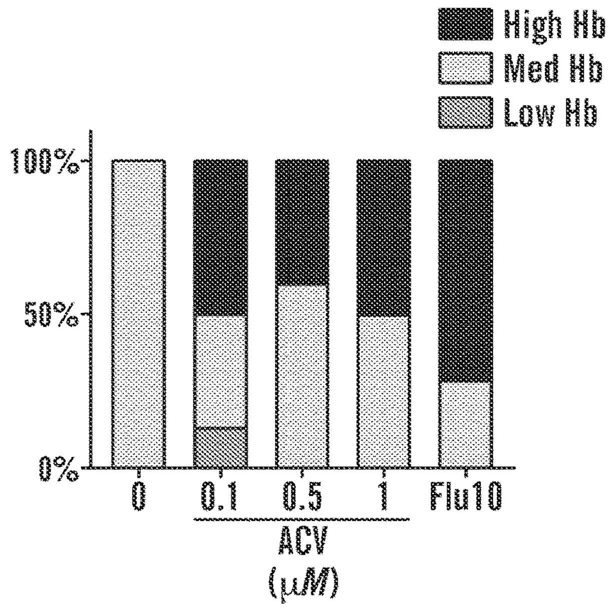
Figure 25D:
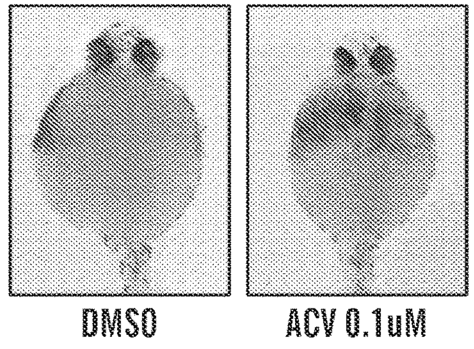

FIG. 23 is a bar graph that indicates FDA-approved phenothiazines such as perphenizine and fluphenazine increase Hb in the anemic rps29−/− zebrafish embryos. However, long-term exposure to phenothiazines are associated with negative neurological side effects. Thus we wanted to screen for phenothiazine derivatives. Our Rational: Phenothiazines impair locomotor activity in zebrafish (Boehmler W. et al. Genes, Brain and Behavior. (2007)), we need a compound that will not enter the brain, others are generating phenothiazine derivatives and there is a high-throughput screen for BBB exclusion with behavior FIG. 24 is a schematic of the generation of phenothiazine derivatives 2 general synthesis methods to generate the compounds to test were used. Synthesis 1: compounds which retain the active chemotype (the phenothiazine ring system) and are systematically diversified at a permissive site distal to the aliphatic piperazine. In brief we use an efficient and highly parallel biasing library strategy. Synthesis 2: focused library to explore determinants around the tricyclic ring system for biological activity FIGS. 25A to 25D are bar graphs and zebrafish photos that indicate two sample derivatives synthesized increase Hb in rps29−/− embryos: Perpenazine succ (PerSucc) see FIG. 25A and ACV see FIG. 25C. FIG. 25B Persucc treated embryo as compared to DMSO embryo. FIG. 25D ACV treated embryo as compared to DMSO embryo.

Figure 26:
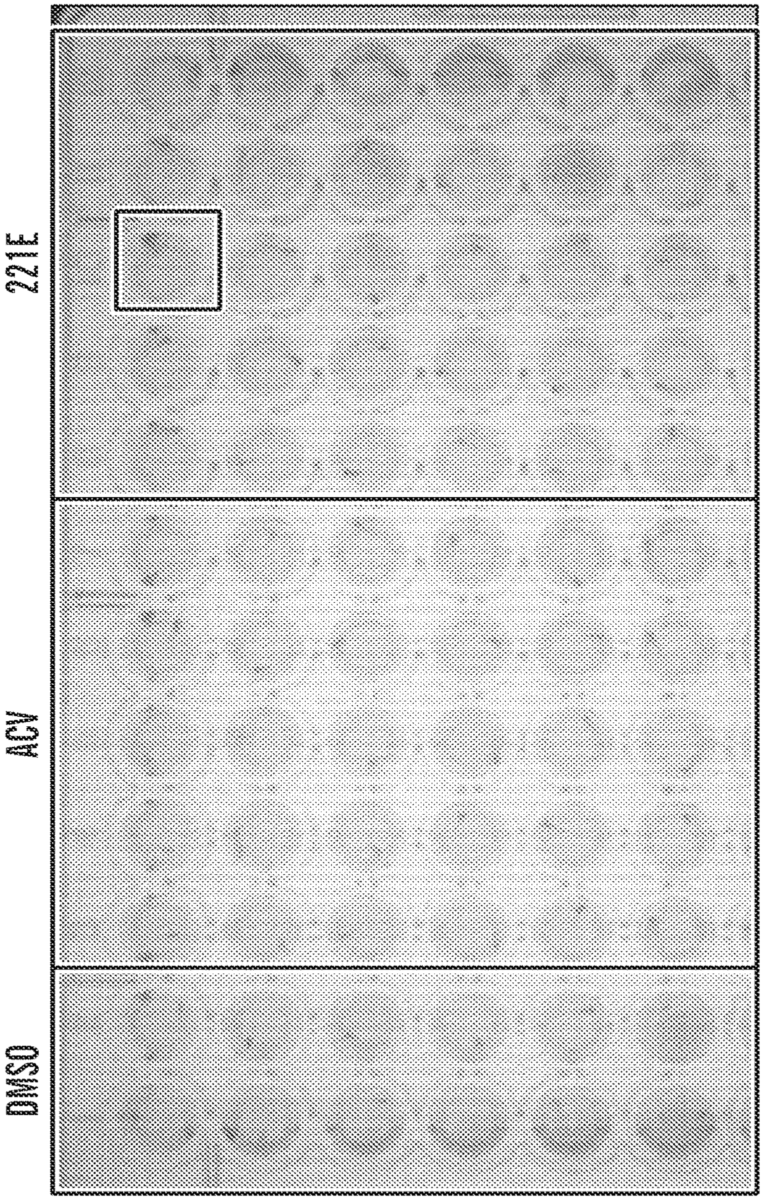

FIG. 26 is a sample photo of a plate of behavior tracking. 6 dpf WT zebrafish were used, 1 fish/well of 96 well plate. Drug was delivered into fish water, we added drug to well and tracked movement for 2 h. We then used a Matlab algorithm to quantitate movement Drugs: Perphenazine Succ (PerSucc): 221E, and ACV. Yellow square highlights an representative fish swimming very erratically.

Figure 27A:
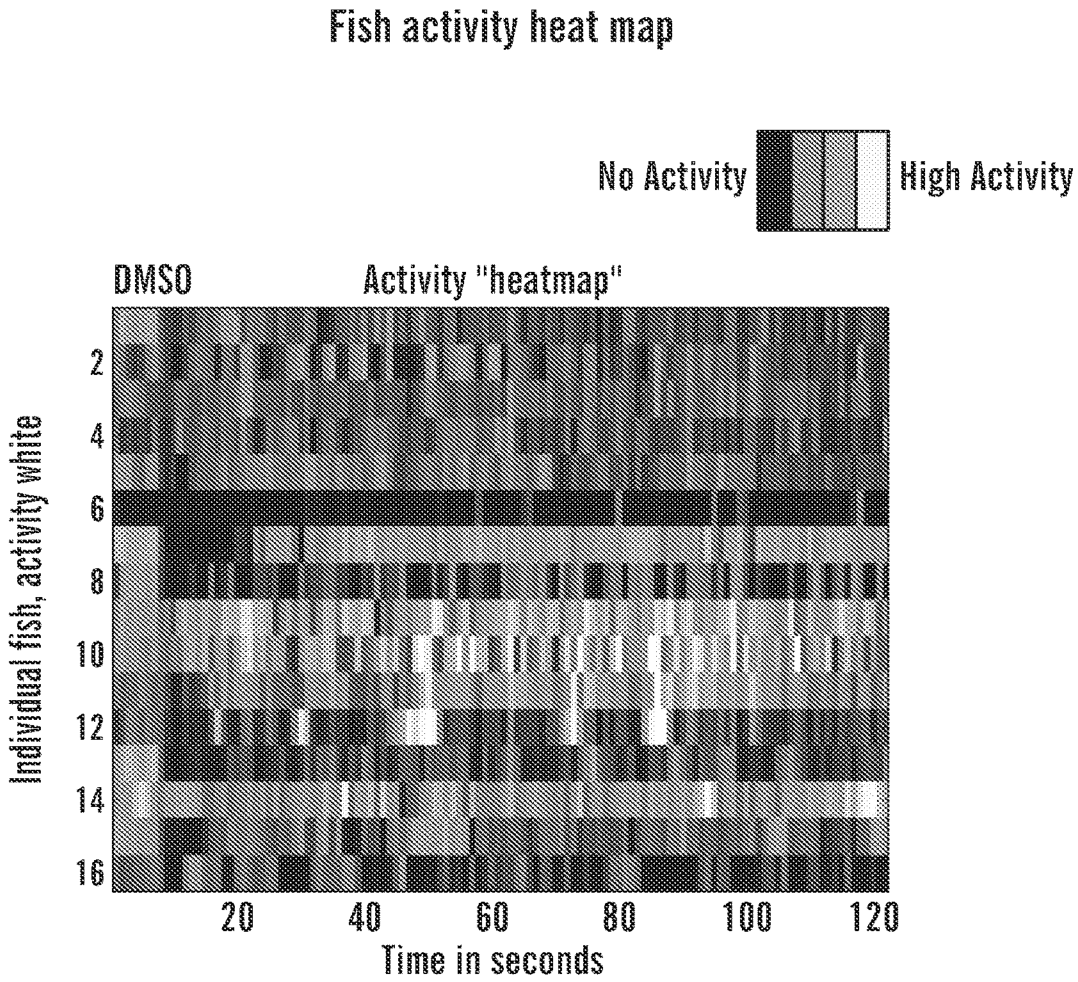
Figure 27B:
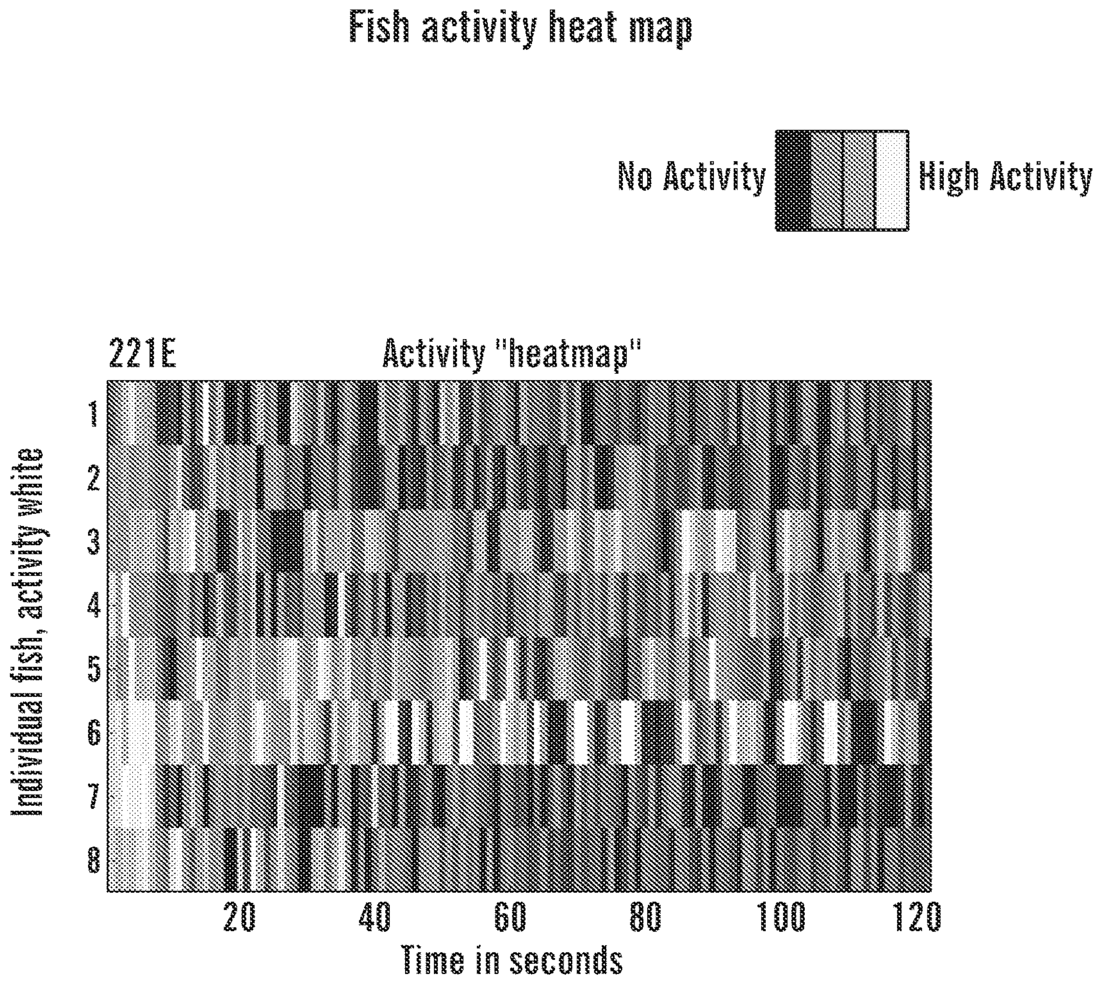
Figure 27C:
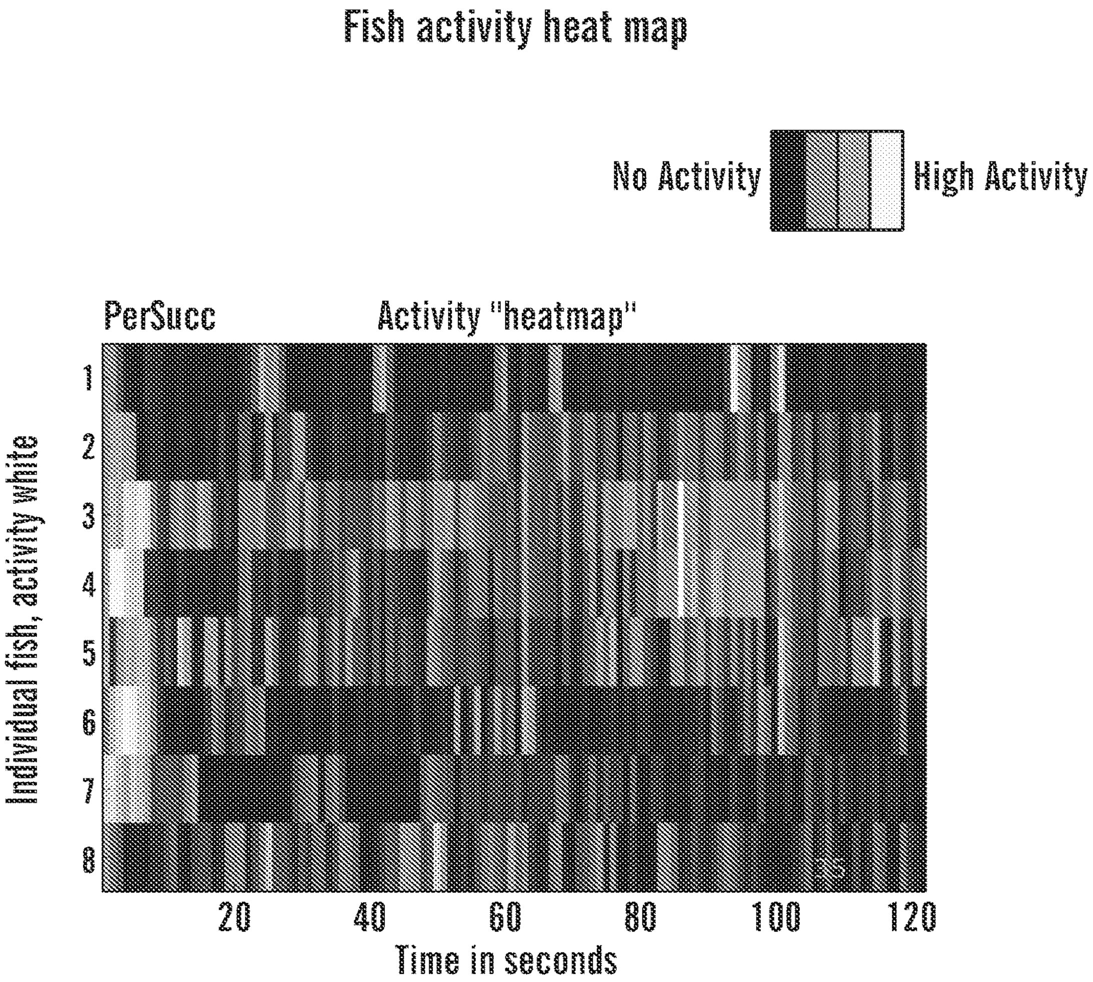

FIGS. 27A to 27C are heat maps of fish activity over 2 h of recording. 221E (FIG. 21B) and Persucc (FIG. 21C) are drugs. DMSO is the control vehicle (FIG. 21A).

Figure 28B:
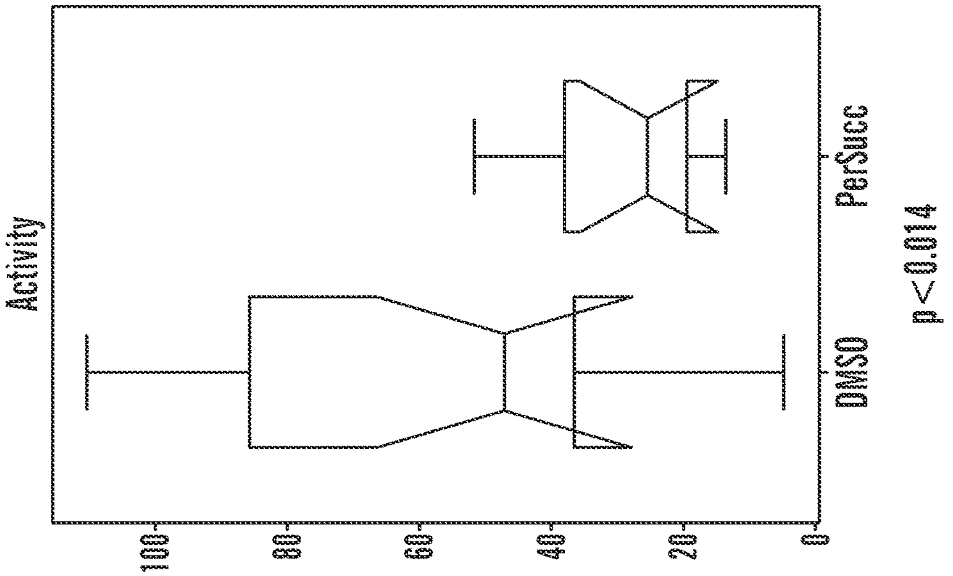
Figure 28A:
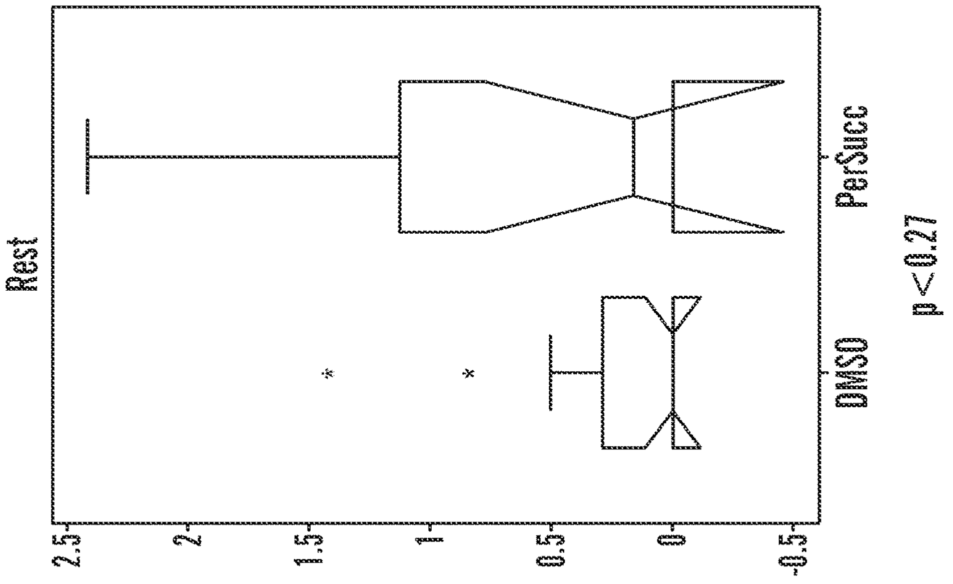

FIGS. 28A to 28B are graph data summarizing the movement of the fish over 2 h with addition of PerSucc at Rest (FIG. 28A) or Activity (FIG. 28B). PerSucc treated fish are less active and rest more than DMSO treated fish.

Figure 29B:
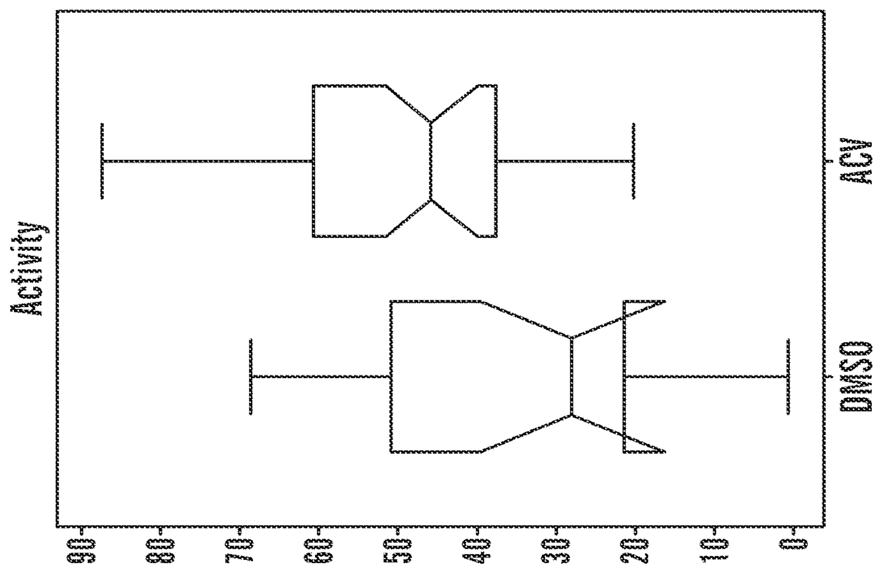
Figure 29A:
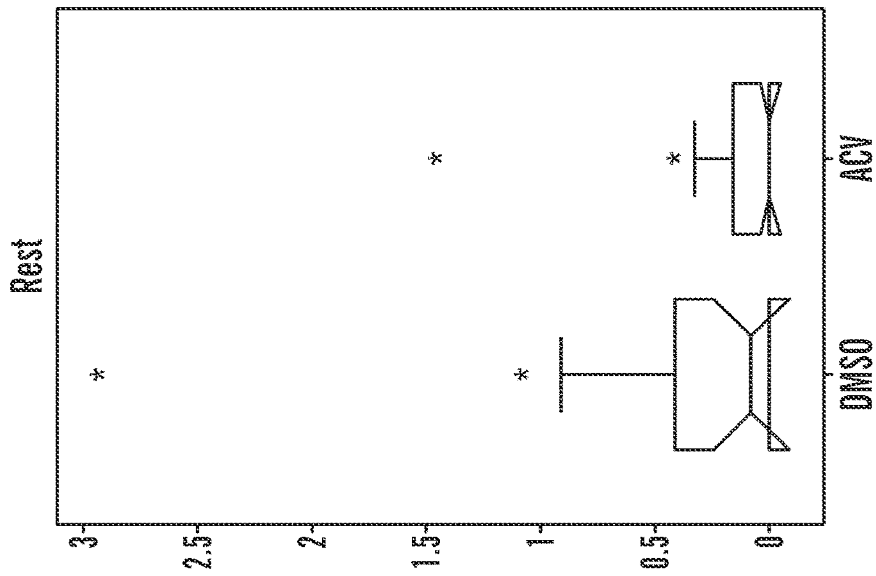
Figure 30A:
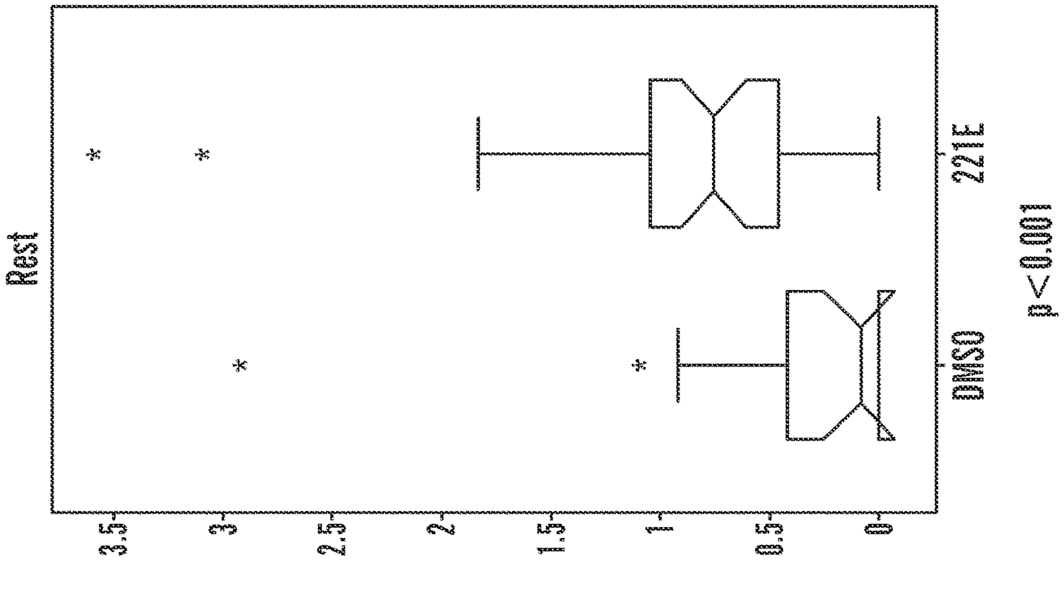
Figure 30B:
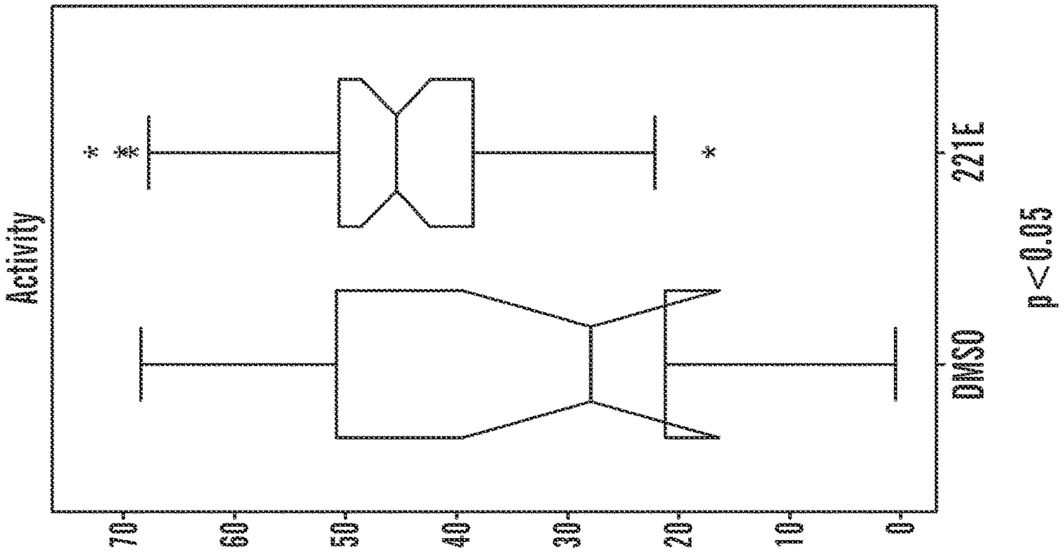

FIGS. 29A to 29B are graph data summarizing the movement of the fish over 2 h with addition of ACV at Rest (FIG. 29A) or Activity (FIG. 29B). ACV treated fish are more active and rest less than DMSO treated fish FIGS. 30A to 30B are graph data summarizing the movement of the fish over 2 h with addition of 221E at Rest (FIG. 30A) or Activity (FIG. 30B). 221E treated fish have more erratic activity because they rest less and move more than DMSO treated fish. They pause and then move really fast, then pause and do it again. Thus the behavior studies represent a robust and rapid assay that can differentiate zebrafish movement: more and less activity vs. erratic, and statistics can be obtained with as little as 8 fish per treatment.

FIG. 31 shows the chemical structures of compounds used in some embodiments of the invention.

FIG. 32 shows chemical structures of specific phenothiazine derivatives.

FIG. 33 shows chemical structures of specific phenothiazine derivatives. Note Abbreviated compound name e.g. is DB-4-083=083.

Figure 34A:
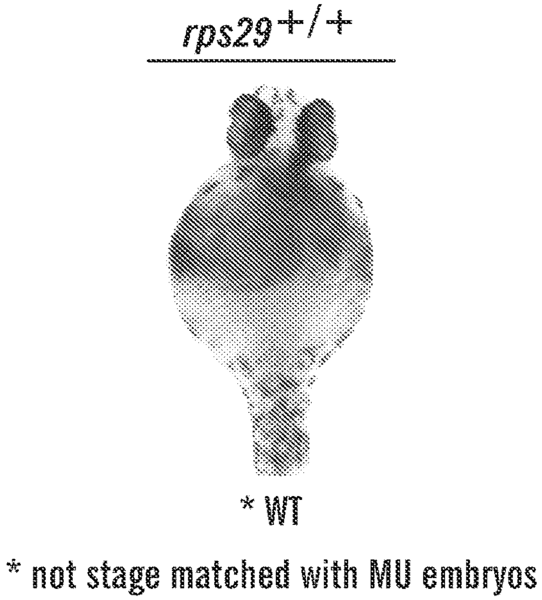
Figure 34B:
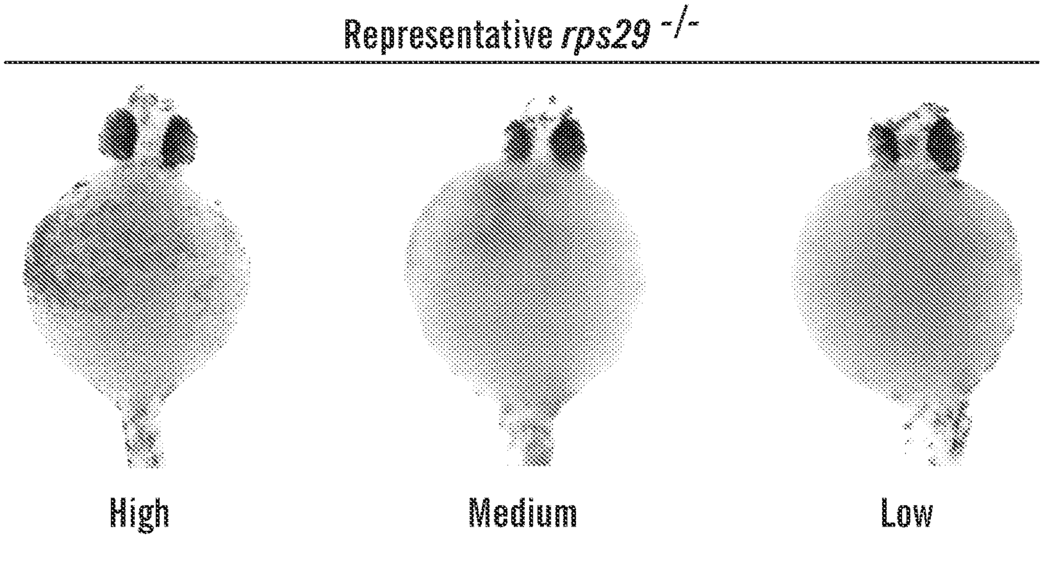

FIGS. 34A to 34B are zebrafish photos of the scoring method for hemoglobin levels. Wildtype leves (FIG. 34A). High, medium and low levels are shown in (FIG. 34B).

Figure 35A:
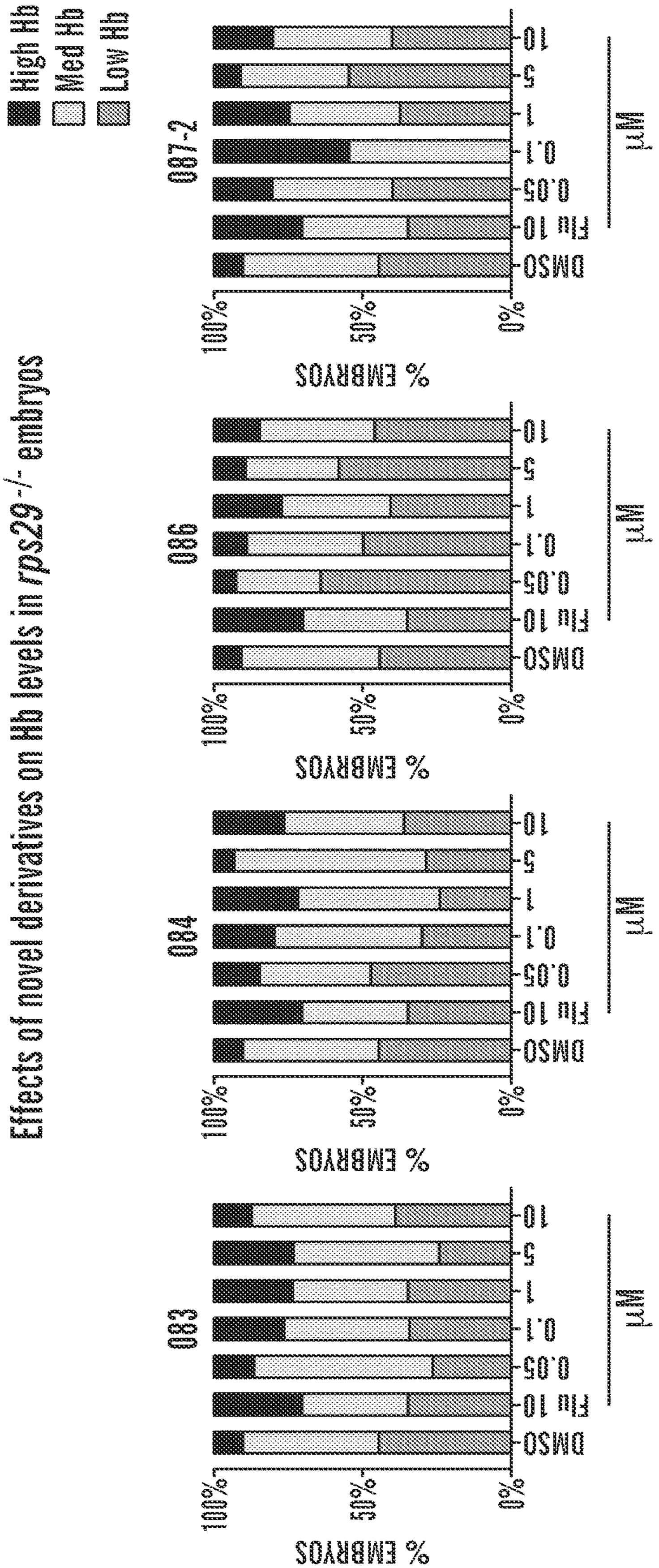
Figure 35B:
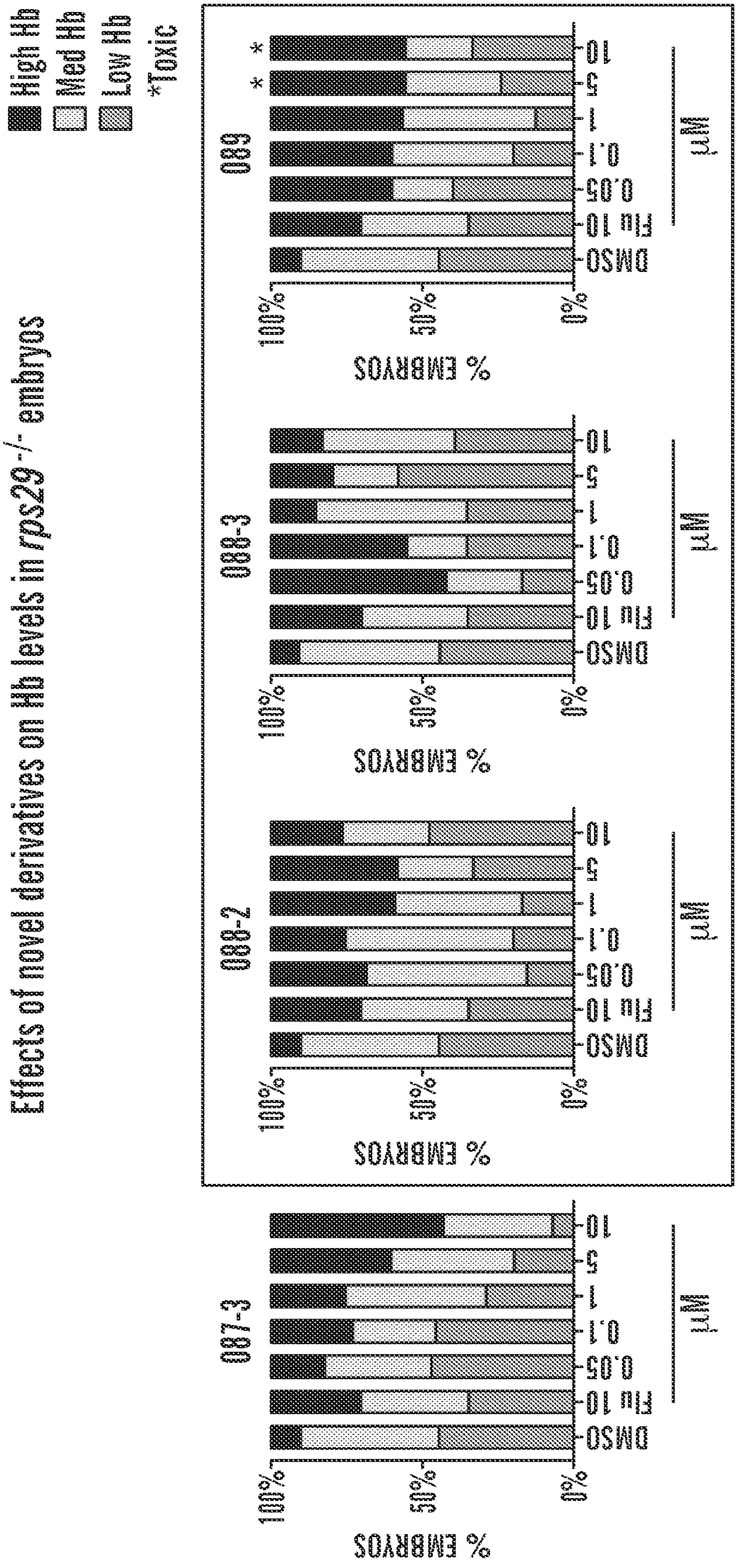

FIGS. 35A and 35B are bar graphs showing the effect of the various phenothiazine derivatives on Hb levels in rps−/− embryos. FIG. 35A: 083; 084; 086; and 087-2 effects. FIG. 35B: 087-3; 088-2; 088-3; and 089 effects.

Figure 36A:
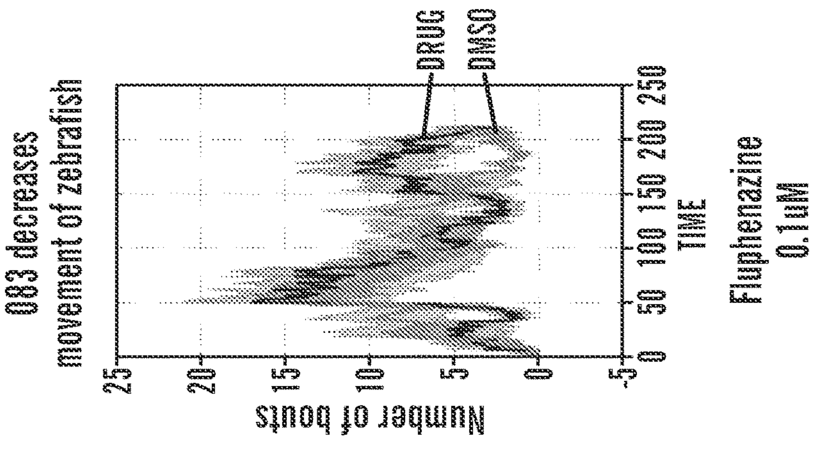
Figure 36B:
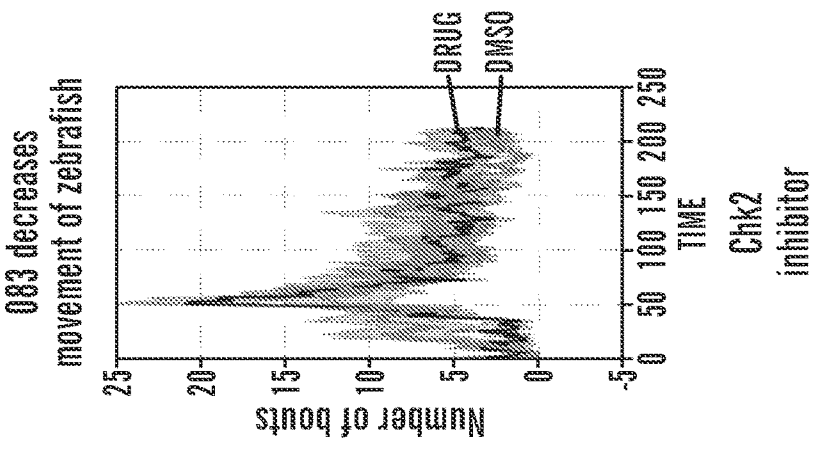
Figure 36C:
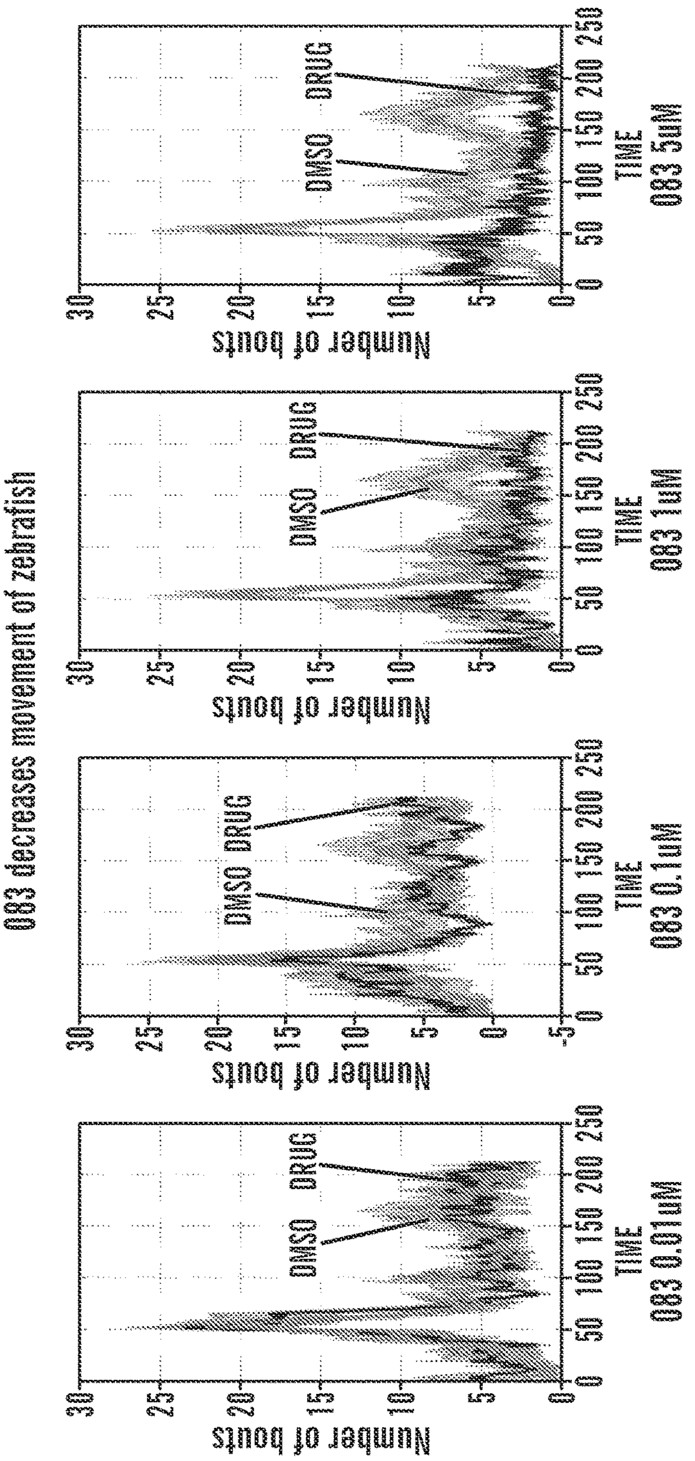
Figure 36D:
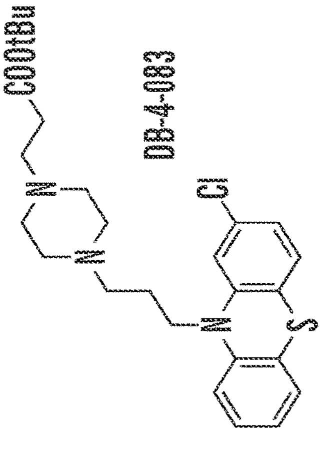

FIGS. 36A to 36D are graphs of the number of movement with DMSO or drug. FIG. 36A: fluphenazine. FIG. 36B: Ch2 inhibitor. FIG. 36C: 083. FIG. 36D: chemical structure of 083. 083 decreases movement of zebrafish.

Figure 37A:
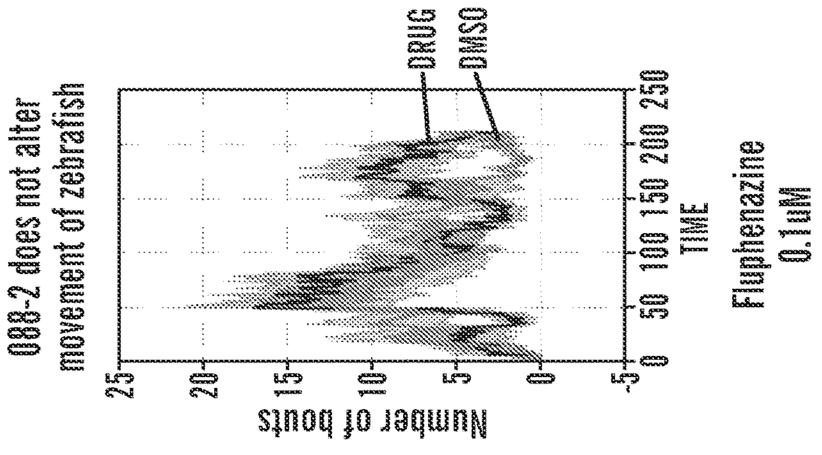
Figure 37B:
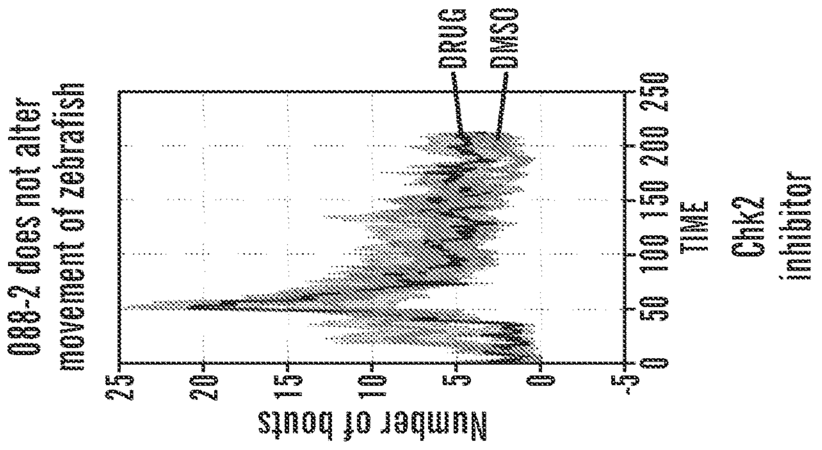
Figure 37C:
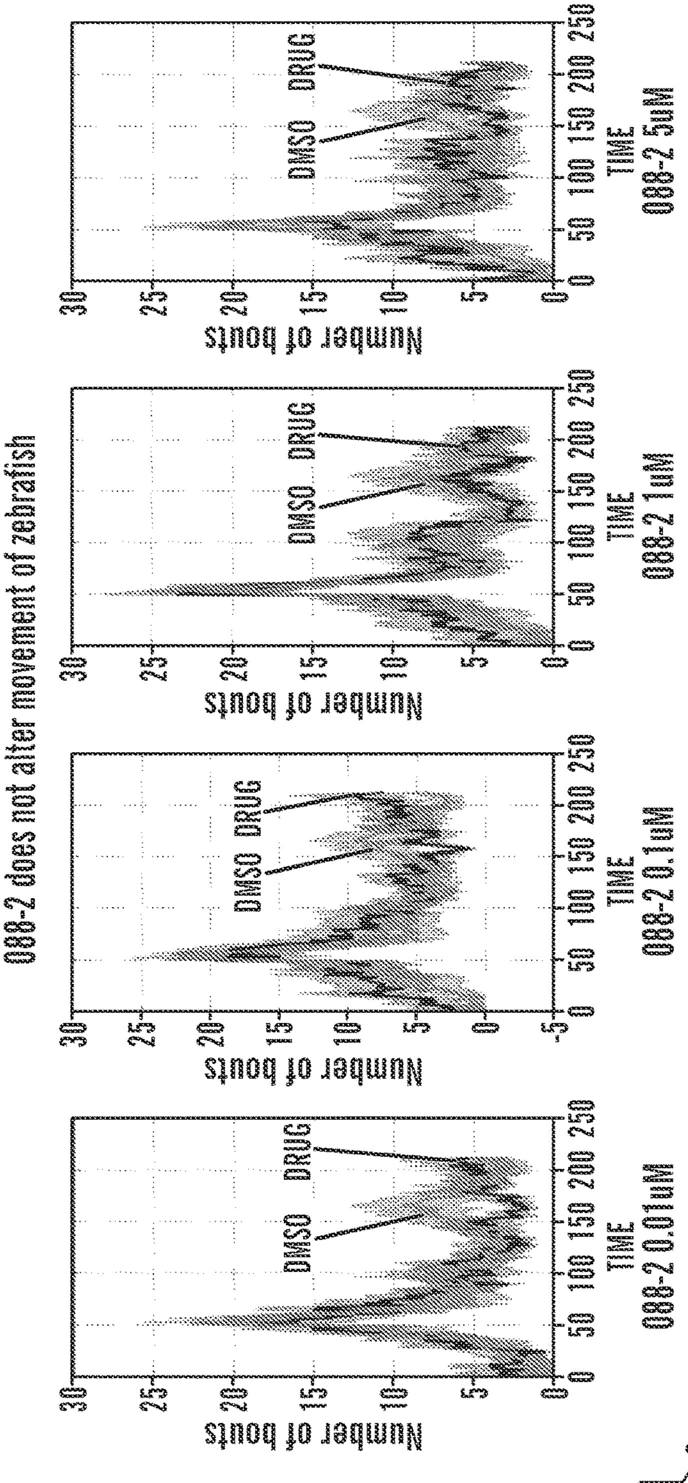
Figure 37D:
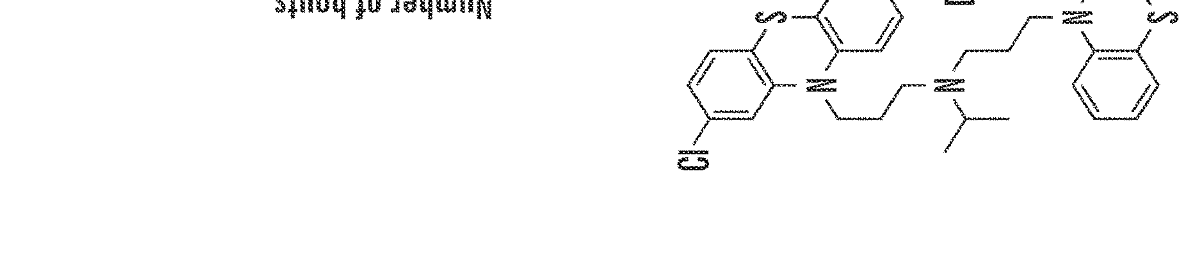

FIGS. 37A to 37D are graphs of the number of movement with DMSO or drug. FIG. 36A: fluphenazine. FIG. 37B: Ch2 inhibitor. FIG. 37C: 088-2. FIG. 37D: chemical structure of 088-2. 088-2 does not alter movement of zebrafish.

Figure 38A:
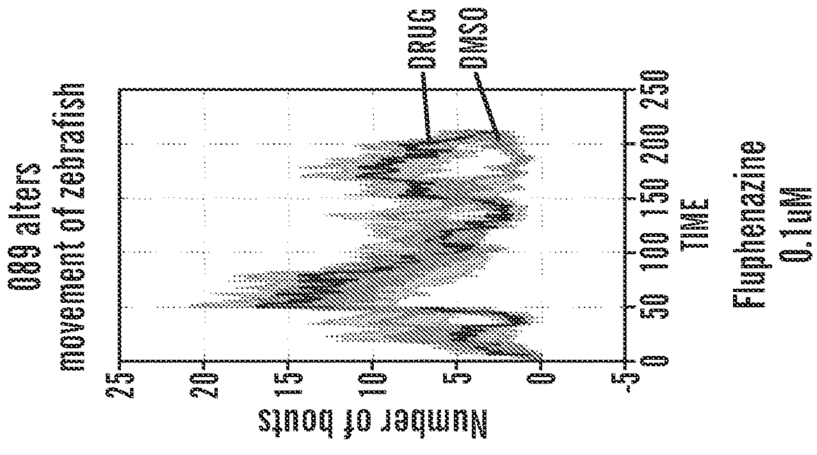
Figure 38B:
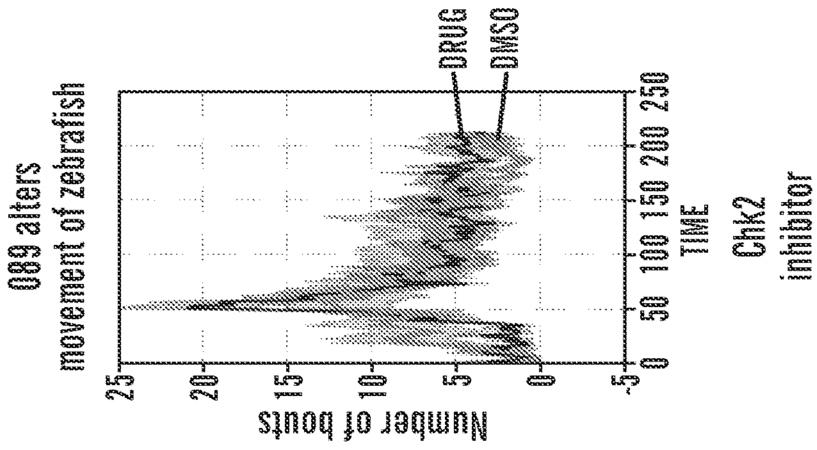
Figure 38C:
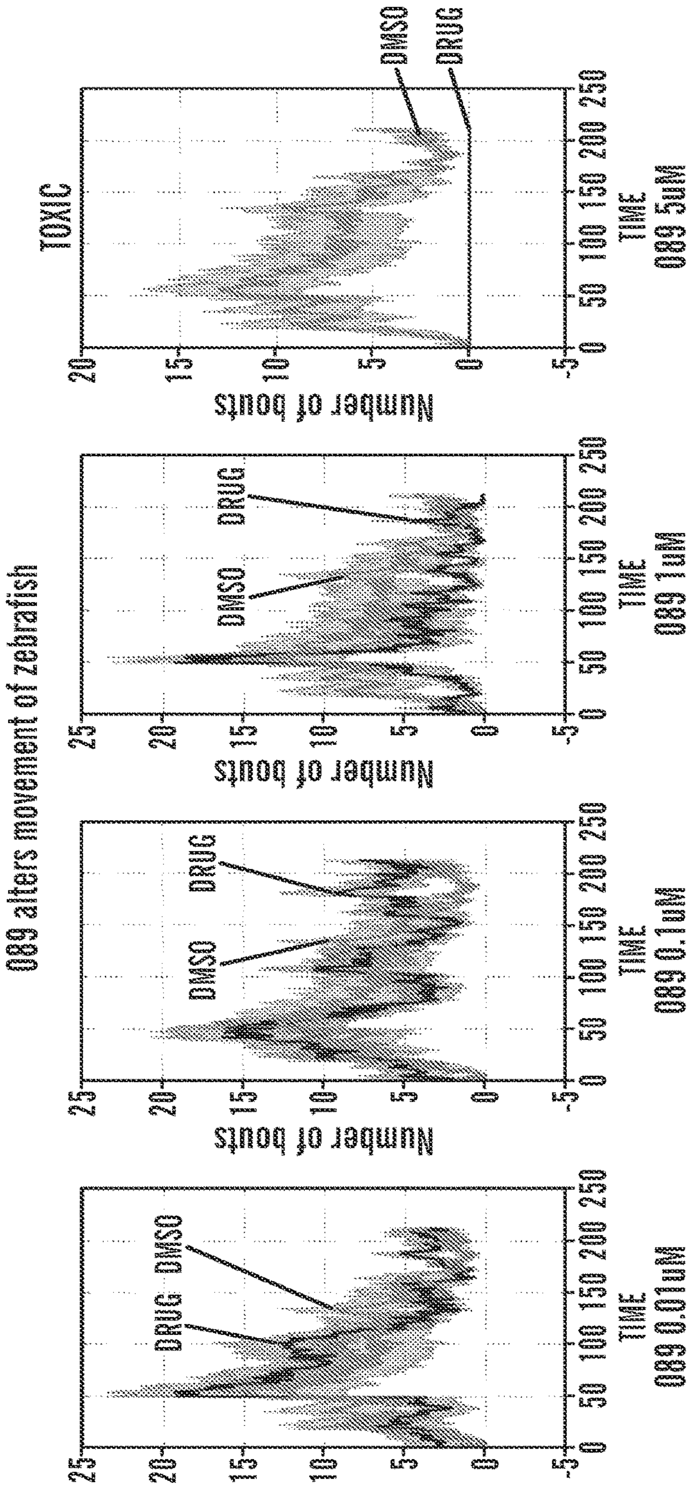
Figure 38D:
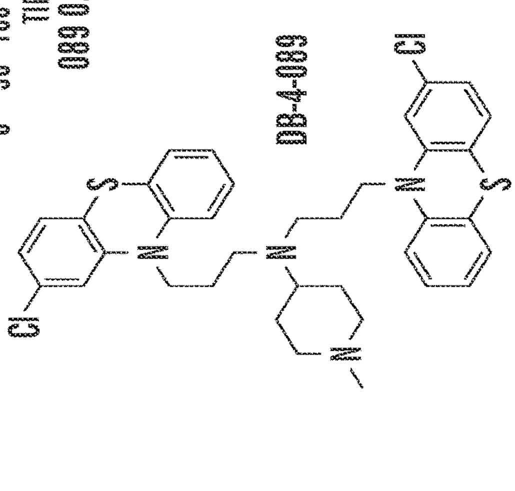

FIGS. 38A to 38D are graphs of the number of movement with DMSO or drug. FIG. 38A: fluphenazine. FIG. 38B: Ch2 inhibitor. FIG. 38C: 089. FIG. 38D: chemical structure of 089. 089 alters movement of zebrafish.

Figure 39B:
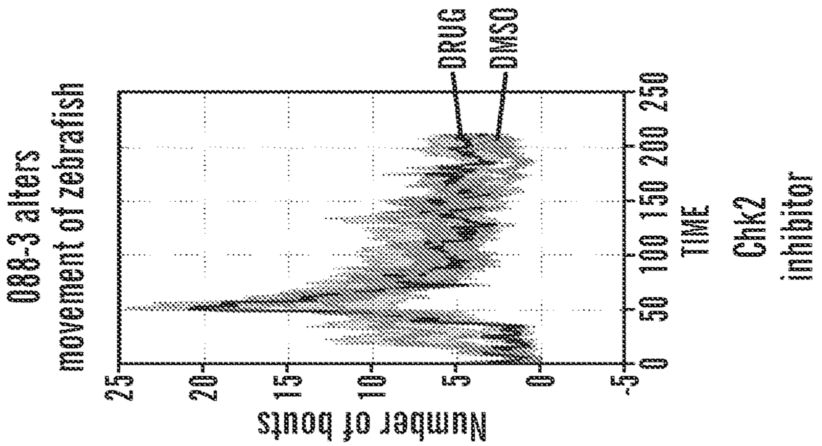
Figure 39A:
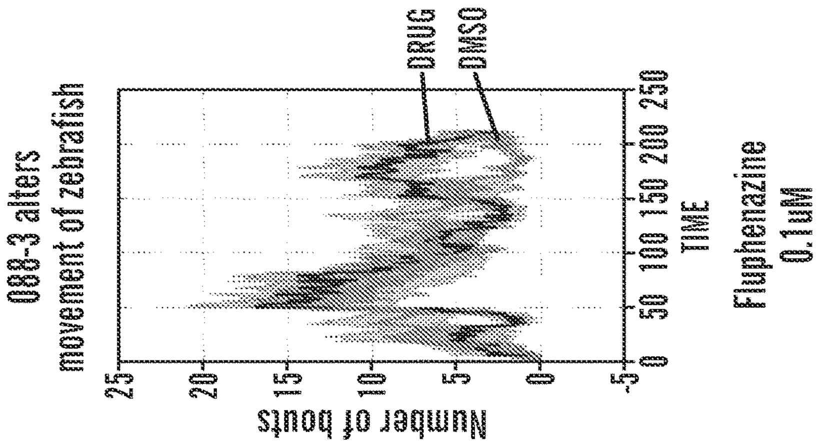
Figure 39C:
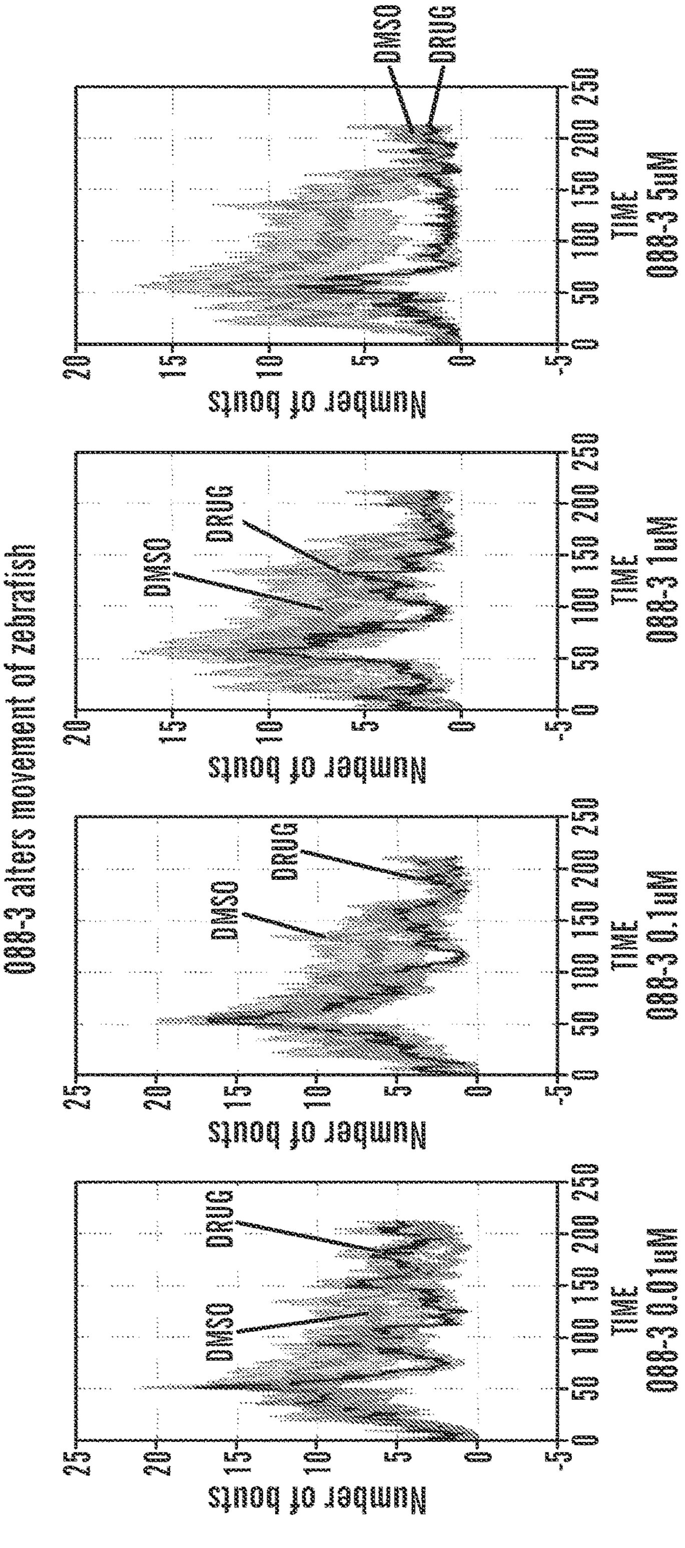
Figure 39D:
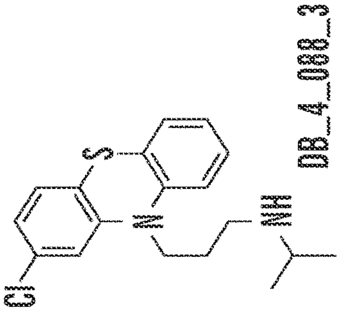

FIGS. 39A to 39D are graphs of the number of movement with DMSO or drug. FIG. 39A: fluphenazine. FIG. 39B: Ch2 inhibitor. FIG. 39C: 088-3. FIG. 39D: chemical structure of 088-3. 088-3 alters movement of zebrafish.

Figure 40:
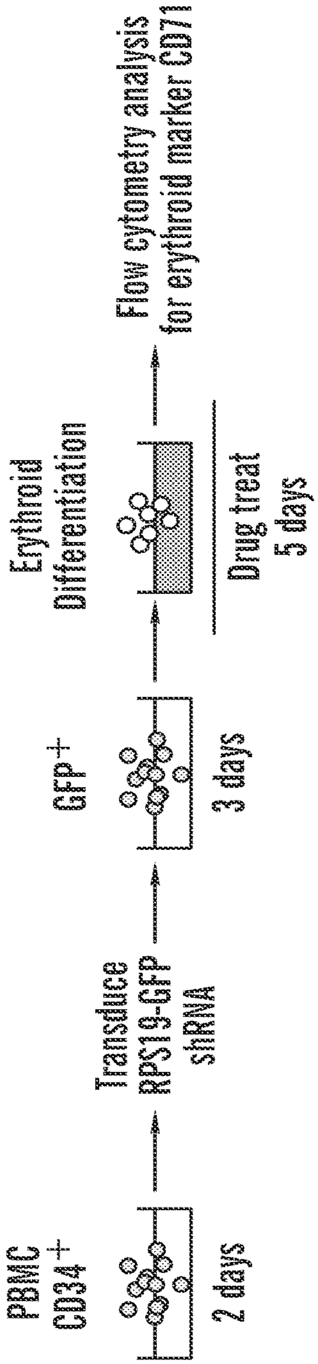

FIG. 40 is a schematic of the testing of novel phenothiazine derivatives in a human in vitro model of DBA. Primary human peripheral blood mononuclear cells (PBMCs) are transduced with RPS19-GFP shRNA to make a ribosomal protein deficiency. Cells are transferred to erythroid differentiation media and treated once for 5 days with Drug. Cells are harvested and analyzed for erythroid precursors by flow cytometry for $CD71^+$ cells.

Figure 41:
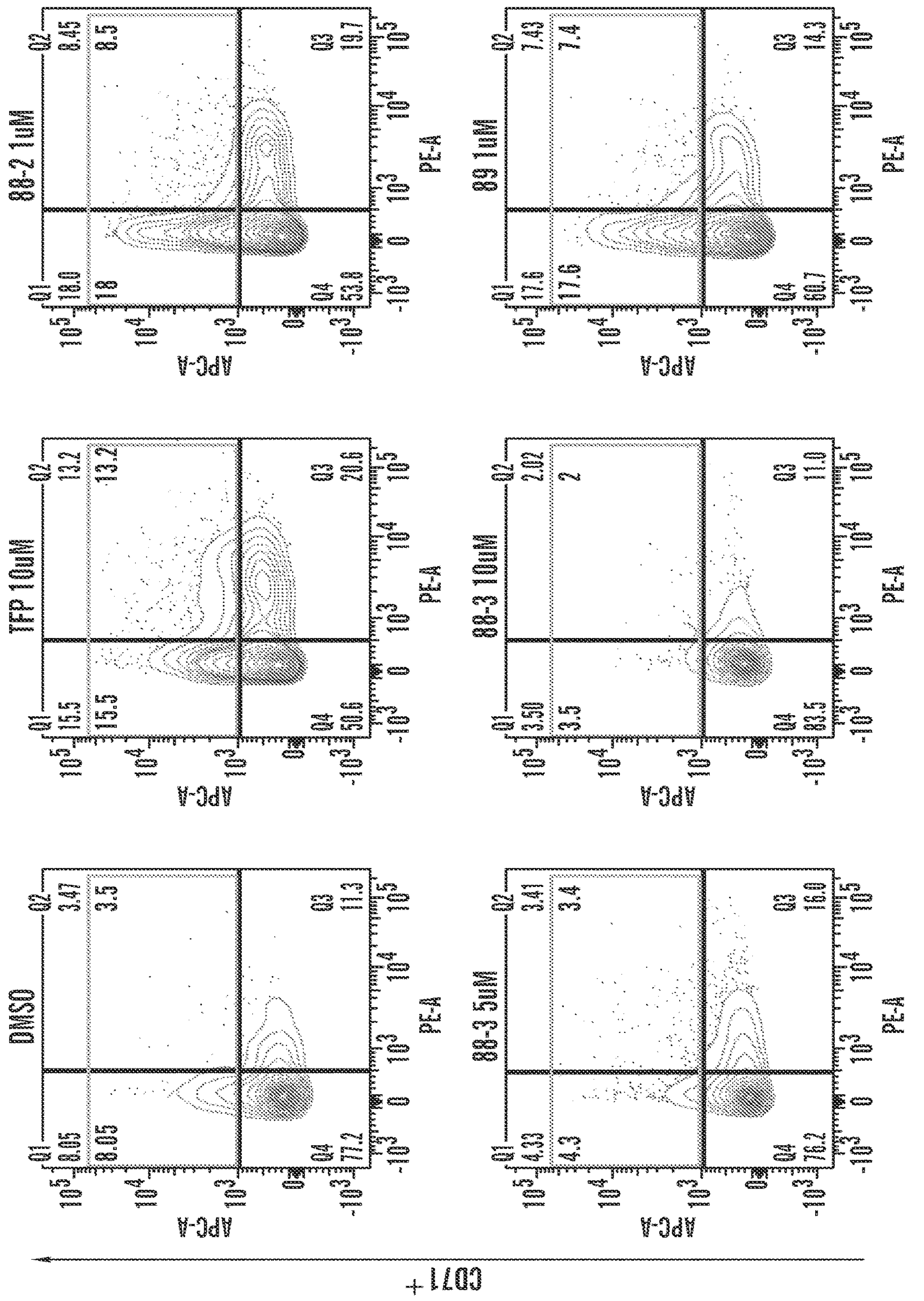
Figure 41:
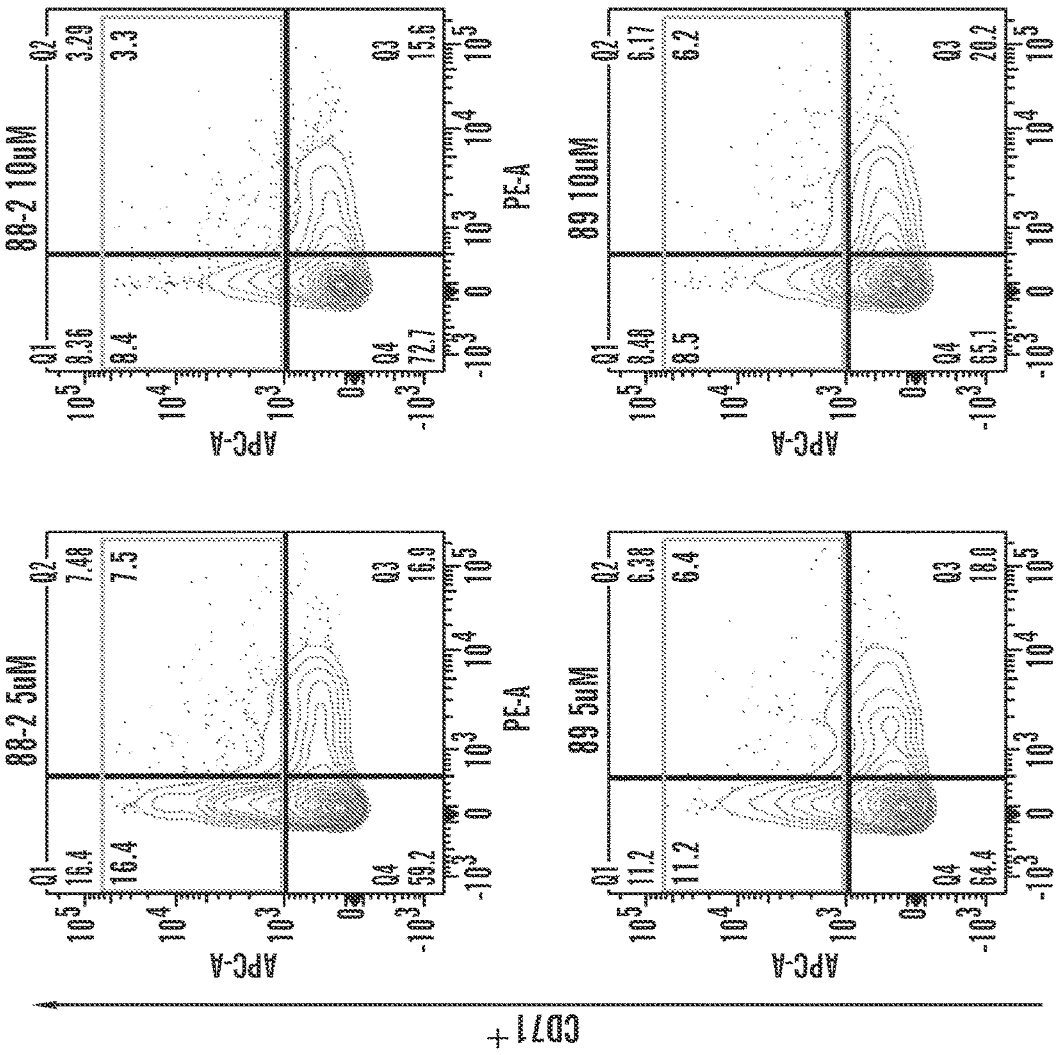

FIG. 41 Flow cytometry charts for $CD71^+$ cells in the presence of various phenothiazine derivatives as indicated in FIG. 40.

Figure 42:
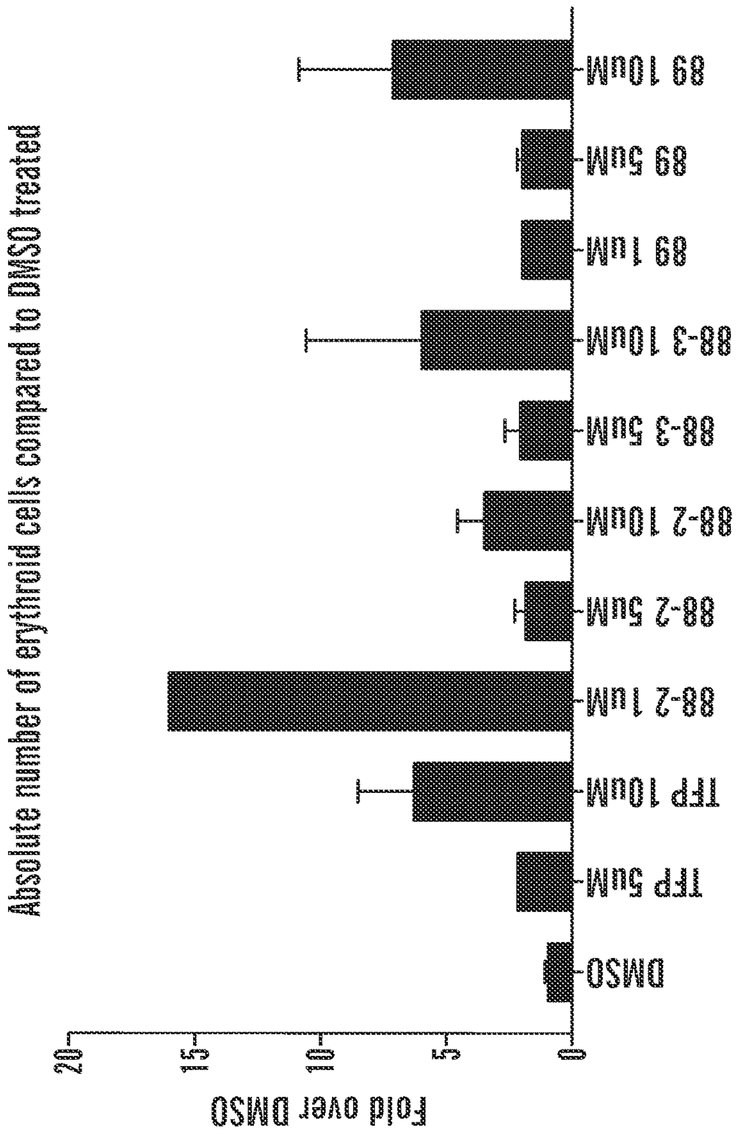

FIG. 42 is a bar graph depicting the absolute number of erythroid cells compared to DMSO treated cells. The phenothiazine derivatives increase the absolute number of erythroid cells.

FIG. 43A chart that includes a brief summary of the effects of the phenothiazine derivatives on Hb, behavior and Red Blood Cell (RBC) differentiation.

DETAILED DESCRIPTION OF THE INVENTION

The present invention is based, in part, upon the discovery that RSK signaling is upregulated in ribosomal protein deficient cells, e.g. RPA19 deficient cells. The inventors have discovered that RSK is activated upon RPS19 deficiency in CD34 cells and that inhibitors of RSK (p90s6K) as well as inhibitors of p70s6K increase hemoglobin (Hb) in rps29−/− zebrafish embryos, an in vivo model of ribosomal protein defect. The inventors have further determined that inhibitors of Chk2 rescue the Hb in rps29−/− embryos.

Accordingly, the invention relates to the use of novel classes of compounds, i.e. inhibitors of RSK (p90S6K), e.g. SL; inhibitors of p70S6K, e.g. PF; and inhibitors of rps6, to treat ribosomal disorders and ribosomopathies. In some embodiments, the invention relates to the use of specific Chk2 inhibitors, i.e. CCT and III, for treatment of ribosomal disorders and ribosomapathies, e.g. DBA. In some embodiments, the invention relates to the use of specific phenothiazine derivatives, e.g. PerSucc, ACV, and 221E, DB-4-088-2 (088-2); DB-4-088-3 (088-3); DB-4-086 (086); DB-4-087-2 (087-2); DB-4-087-3 (087-3); DB-4-089 (089), tri-fluoronated substituent derivatives, or a compound of Formula I or Formula II, to treat ribosomal disorders and ribosomopathies, e.g. DBA.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Definitions

The term "regulate" used herein in reference to expression of a gene, refers to producing an effect on, for example, gene expression. In some embodiments, the effect can be stimulatory, such as increasing expression of a gene. In some embodiments, the effect can be inhibitory, such as decreasing expression of a gene. The terms "regulate" and "modulate" are interchangeably used herein.

The terms "calmodulin inhibitor" used interchangeably herein, generally refers to an agent or molecule that inhibits the activity or expression of calmodulin. Calmodulin inhibitors can be of synthetic or biological origins. They can be organic, or inorganic molecules, or peptides, antibodies or antisense RNA that inhibit calmodulin. Inhibitors of calmodulin of the invention are chemical entities or molecules that can inhibit expression of calmodulin and/or biological activity of calmodulin, for example, compounds of TFP and FLU, prodrugs, derivatives and pharmaceutically acceptable salts thereof, have previously been determined to be useful in treatment of ribosomal disorders (See US publication 2015/0265627). Assays for monitoring Calmodulin activity are known in the art. See for example US publication 2015/0265627. Herein, the inventors have identified, previously undisclosed compounds that that work particularly well for treatment of ribosomal disorders, e.g. ACV, 221E and Per-Succ, DB-4-088-2 (088-2); DB-4-088-3 (088-3); DB-4-086 (086); DB-4-087-2 (087-2); DB-4-087-3 (087-3); DB-4-089 (089), tri-fluoronated substituent derivatives, or a compound of Formula I or Formula II (see FIGS. 25 and 32).

The term "ribosomal protein", are also referred to herein as "r-proteins" refers to any of the intracellular ribonucleoprotein particles concerned with protein synthesis; they consist of reversibly dissociable units and are found either bound to cell membranes or free in the cytoplasm. They may occur singly or occur in clusters (polyribosomes). They may occur singly or in clusters, called polyribosomes or polysomes, which are ribosomes linked by mRNA and are actively engaged in protein synthesis. Ribonucleoproteins (often referred to as "RNPs") are important in protein synthesis; they consist of two, one large (L) and one small (S), reversibly dissociable units (called also 60S and 40S subunits in eukaryotes (50S and 30S in bacteria)). The term includes any of the proteins that, in conjunction with rRNA, make up the ribosomal subunits involved in the cellular process of translation. The term encompasses proteins of the small (S) subunit and the large (L) subunit of the ribosomes. Due to the high conservation of both the RNA and proteins moieties of ribosomes and of the ribosome biogenesis machinery from yeast and bacteria, a large part of the knowledge about these organic molecules has come from the study of *E. coli* ribosomes, and also applies to humans. In the small (30S) subunit of *E. coli* ribosomes, the proteins denoted S4, S7, S8, S15, S17, S20 bind independently to 16S rRNA. After assembly of these primary binding proteins, S5, S6, S9, S12, S13, S16, S18, and S19 bind to the growing ribosome. These proteins also potentiate the addition of S2, S3, S10, S11, S14, and S21. Protein binding to helical junctions is important for initiating the correct tertiary fold of RNA and to organize the overall structure. Nearly all the proteins contain one or more globular domains. Moreover, nearly all contain long extensions that can contact the RNA in far-reaching regions. Additional stabilization results from the proteins' basic residues, as these neutralize the charge repulsion of the RNA backbone. Protein-protein interactions also exist to hold structure together by electrostatic and hydrogen bonding interactions. Theoretical investigations pointed to correlated effects of protein-binding onto binding affinities during the assembly process [2]

The term "ribosomal disorder" or "ribosomal protein disorder" refers to a disease or disorder linked to a mutated and/or abnormal function of a ribosome protein. It can include a disease due to mutation in a ribosomal protein, or a disease due to a decreased level, or partial loss of function, of a ribosomal protein, or alternatively, a disease due to an increased level of a ribosomal protein, as compared to a normal healthy control subject. The term ribosomal disorder includes genetic diseases of ribosomal proteins, including but not limited to, Diamond Blackfan anemia (DBA), myelodysplasia, Shwachman-Diamond Syndrome (SDS) and Treachers Collins Syndrome (TCS).

The term "ribosomopathy" or "ribosomopathies" refers to any disease or malfunction of ribosomes. Ribosomes are small organelles found in all cells which are involved in the production of proteins by translating messenger RNA. A disease or malfunction of ribosomes include (i) disease of ribosomal biogenesis proteins, (ii) disease of small nucleolar ribonuceloproteins, and (iii) diseases of ribosomal proteins (as discussed above in the definition of "ribosomal protein disorder"), and are all reviewed in Freed et al., Mol. Biosyst. 2010; 6 (3); 481-493 entitled "When ribosomes go bad: diseases of ribosome biogenesis", which is incorporated herein in its entirety by reference. Diseases of ribosomal biogenesis proteins include, but are not limited to Treachers Collins syndrome (TCS), male infertility due to a mutation inUTP14c, native American indian childhood cirrhosis (NAIC), Bowen-Conradi syndrome (BCS), alopecia neurological defect and endrocrinopathy syndrome (ANE syndrome), shwachman-diamond syndrome (SDS), candidate gene for primary open angle glaucoma (POAG), and modifier of neurofibromatosis type I (NF1). Diseases of small nucleolar ribonuceloproteins include, but are not limited to, Anauxetic dysplasia (AD), cartilage-hair dysplasia (also called metaphyscal chondrodysplaia, McKusick type; CCH), metaphyseal dysplasia without hypotrichosis (MDWH), Dyskeratosis congenita (also called Zinzzer-Engman-Cole syndrome), Hoyeraal-Hreidarsson syndrome (where some cases are severe variants of Dyskeratosis congenita), and Prader-Willi syndrome (PWS)

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

The term "functional derivative" and "mimetic" are used interchangeably herein, and refers to compounds which possess a biological activity (in particular functional biological activity) that is substantially similar to the biological activity of the entity or molecule for which it's a functional derivative of. The term functional derivative is intended to include the fragments, variants, analogues or chemical derivatives of a molecule. In certain embodiments, functional derivatives and functional analogues of calmodulin inhibitors (e.g., functional analogues of TFP, A-3, W-7, A-7, W-5 and CGS-9343) can be assessed for their biological activity using the assay as disclosed herein, where derivatives and analogues which inhibit calmodulin would be considered as functional derivatives or functional analogues of such calmodulin inhibitors.

The term "analog" as used herein refers to an agent that retains the same, or a substantially similar biological function (i.e., inhibition of calmodulin) and/or structure as the molecule or chemical or polypeptide it is an analogue of. Examples of analogs include peptidomimetics (a peptide analog), peptide nucleic acids (a nucleic acid analog), small and large organic or inorganic compounds, as well as derivatives and variants of a polypeptide or nucleic acid herein.

The term "substantially similar", when used to define the biological activity of a derivative or analogue of an inhibitor (e.g. inhibitor of p90S6k, or p70S6K, or Chk2, or calmodulin) as compared to the biological activity of the inhibitor to which it is a derivative or analogue of, means that a particular derivative or analogue differs from the initial parent inhibitor in chemical structure, by one or more groups or elements, including substitutions, deletions, or additions of groups of elements, the net effect of which is to retain at least some of the biological activity found in the initial parent inhibitor with respect to inhibition of kinase or other RSK, Chk2 activity and/or expression. Such biological activity of inhibition by a functional derivative or analogue of can be assessed by one of ordinary skill in the art using assays well known in the art, for example, in in vitro kinase assays, which measures phosphorylation of substrates.

The term "tissue" is intended to include intact cells, blood, blood preparations such as plasma and serum, bones, joints, muscles, smooth muscles, and organs.

The term "subject" includes human and other mammalian subjects that receive either prophylactic or therapeutic treatment. The term "subject" and "individual" are used interchangeably herein, and refer to an animal, for example a human, to whom treatment, including prophylactic treatment, with the cells according to the present invention, is provided. The "non-human animals" of the invention include mammals such as rats, mice, rabbits, sheep, cats, dogs, cows, pigs, and non-human primates.

The terms "a reference sample" or "a reference level" as used interchangeably herein refer to a negative control of the condition. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level or sample used herein refers to the level measured at a previous time point from a subject being treated.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate ribosomal protein function. As used herein with respect to a ribosomal protein disorder, the term treating is used to refer to the reduction of a symptom and/or a biochemical marker of a ribosomal protein disorder by at least 10%., for example a reduction of p21 and/or p53 levels in CD34+ cells in the subject, or a return of hemoglobin back to normal levels, or a restoration or prevention of craniofacial deformities. For example but are not limited to, a reduction of p21 and/or p53 levels in CD34+ cells in the subject, as an illustrative example only, by 10%, would be considered effective treatments by the methods as disclosed herein.

As used herein, the term "treating" includes preventing the progression and/or reducing or reversing at least one adverse effect or symptom of a condition, disease or disorder associated with a ribosomal protein disorder or ribosomopathy, for example, DBA. Accordingly, in some embodiments, treatment can be prophylactic in terms of completely or partially preventing a disease or sign or symptom of a ribosomal protein disorder or ribosomopathy. For example, subjects known to have a mutation in ribosomal protein or alternatively, low expression levels of a specific ribosomal protein, can be subjected to prophylactic treatment to prevent the onset of one or more symptoms associated with such a mutation in the ribosomal protein, and/or decreased levels in the ribosomal protein. In some embodiments, prophylactic treatment can be administered to subjects who had prior treatment of a disease associated with a ribosomal protein disorder. For example, for subjects who have received corticosteroids or blood transfusions for the treatment of DBA and/or other previous treatment to stabilize their DBA can be prophylactically treated (e.g. with a calmodulin inhibitor and/or calcium channel blocker as disclosed herein).

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

The term "prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

As used herein, "gene silencing" or "gene silenced" in reference to an activity of an RNAi molecule, for example a siRNA or miRNA refers to a decrease in the mRNA level in a cell for a target gene (e.g. p90S6k gene, or p70S6K gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. By way of an example only, in some embodiments RNAi agents which serve to inhibit or gene silence are useful in the methods, kits and compositions disclosed herein to inhibit the RSK p70S6K and p90S6K genes.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "gene product(s)" as used herein refers to include RNA transcribed from a gene, or a polypeptide encoded by a gene or translated from RNA.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. calmodulin, it refers to a reduction in protein or nucleic acid level or activity in a cell, a cell extract, or a cell supernatant. For example, such a decrease may be due to reduced RNA stability, transcription, or translation, increased protein degradation, or RNA interference. In some embodiments, a calmodulin inhibitor which is a small-molecule as disclosed herein can decrease the activity or expression of calmodulin. Preferably, this decrease is at least about 5%, at least about 10%, at least about 25%, at least about 50%, at least about 75%, at least about 80%, or even at least about 90% of the level of expression or activity under control conditions. The term "level" as used herein in reference to calmodulin refers to expression or activity of calmodulin.

The terms "up-regulate", "increase" or "activate" are all used herein to generally mean an increase by a statically significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The term "effective amount" is used interchangeably with the term "therapeutically effective amount" and refers to the amount of at least one agent, e.g., calmodulin inhibitor and/or calcium channel blocker of a pharmaceutical composition, at dosages and for periods of time necessary to achieve the desired therapeutic result, for example, to reduce or stop at least one symptom of the ribosomal disorder or ribosomopathy, for example a symptom of high levels of p53 and/or p21 in CD34+ cells in the subject. For example, an effective amount using the methods as disclosed herein would be considered as the amount sufficient to reduce a symptom of the ribosomal disorder or ribosomopathy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease. Accordingly, the term "effective amount" or "therapeutically effective amount" as used herein refers to the amount of therapeutic agent (e.g. the inhibitors of RSK p90 and p70S6K and specific Chk2 and calmodulin inhibitors disclosed herein) of pharmaceutical composition to alleviate at least one symptom of a ribosomal disorder or ribosomopathy, e.g. DBA. Stated another way, "therapeutically effective amount" of an inhibitor as disclosed herein is the amount of a calmodulin inhibitor or calcium channel blocker which exerts a beneficial effect on, for example, the symptoms of the ribosomal disorder or ribosomopathy. The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify the an inhibitor as disclosed herein which will achieve the goal of reduction in the severity of at least one symptom of a ribosomal protein disease or disorder or ribosomopathy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising an inhibitor of the invention by methods of administration such as parenteral or systemic administration.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application.

As used herein, the term "haloalkyl" refers to an alkyl substituted with one or more "halo" atoms. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to an aromatic 5-8 membered monocyclic, 8-12 membered fused bicyclic, or 11-14 membered fused tricyclic ring system. $C_x$ aryl and $C_x$-$C_y$aryl are typically used where X and Y indicate the number of carbon atoms in the ring system. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. In some embodiments, 1, 2, 3, or 4 hydrogen atoms of each ring may be substituted by a substituent.

Exemplary aryl or heteroaryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like.

Exemplary heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like.

Aryl and heteroaryls can be optionally substituted with one or more substituents at one or more positions with, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cyclyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N═, —$NR^N$—, —$N^+(O^-)$═, —O—, —S— or —$S(O)_2$—, —$OS(O)_2$—, and —SS—, wherein $R^N$ is H or a further substituent.

The term "hydroxy" means the radical —OH.

The term "nitro" means the radical —$NO_2$.

As used herein, the term, "aromatic" means a moiety wherein the constituent atoms make up an unsaturated ring system, all atoms in the ring system are $sp^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term “alkylaryl”, as used herein, refers to an alkyl group substituted with an aryl group. The term “alkylheteroaryl” refers to an alkyl group substituted with an heteroaryl.

The term “alkylthio” refers to an alkyl group, as defined above, having a sulfur radical attached thereto. In preferred embodiments, the “alkylthio” moiety is represented by one of —S-alkyl, —S-alkenyl, and —S-alkynyl. Representative alkylthio groups include methylthio, ethylthio, and the like. The term “alkylthio” also encompasses cycloalkyl groups, alkene and cycloalkene groups, and alkyne groups. “Arylthio” refers to aryl or heteroaryl groups.

The term “acyl” refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolid-2-one-5 pyrrolidinylcarbonyl-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term “alkylamino” means a nitrogen moiety having at least one straight or branched unsaturated aliphatic, cyclyl, or heterocyclyl radicals attached to the nitrogen. The term “alkylamino” includes “alkenylamino,” “alkynylamino,” “cyclylamino,” and “heterocyclylamino.” The term “arylamino” means a nitrogen moiety having at least one aryl radical attached to the nitrogen. For example —NHaryl, and —N(aryl)$_2$. The term “heteroarylamino” means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term “mono- or di-alkylamino” means —NH(alkyl) or —N(alkyl)(alkyl), respectively, such as —$NHCH_3$, —$N(CH_3)_2$, and the like. For example, representative amino groups include —$NHCH_3$, —$N(CH_3)_2$, —NH($C_1$-$C_{10}$alkyl), —N($C_1$-$C_{10}$alkyl)$_2$, and the like.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH3) as well as —$CR_aR_bR_c$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

A “pharmaceutically acceptable salt”, as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., “Pharmaceutical Salts”, *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, olcate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like: and organic acids such as 1,2-ethanedisulfonic acid, 2-hydroxyethanesulfonic acid, 2-naphthalenesulfonic acid, 3-phenylpropionic acid, 4-methylbicyclo[2,2,2]oct-2-ene-1-carboxylic acid, 4,4-methylenebis (3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl) benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of a pharmaceutical composition comprising at least one inhibitor as disclosed herein (e.g. the specific CHK2 and CAM inhibitors, or inhibitors of p70S6K, or p90S6K) such that it enters the animal's system and, thus, is subject to metabolism and other like processes, for example, subcutaneous administration.

The term "statistically significant" or "significantly" refers to statistical significance and generally means a two standard deviation (2 SD) below normal, or lower activity, e.g. inhibition of p70S6K, p90S6k, Chk2 activity, calmodulin activity. The term refers to statistical evidence that there is a difference. It is defined as the probability of making a decision to reject the null hypothesis when the null hypothesis is actually true. The decision is often made using the p-value.

The term "optional" or "optionally" means that the subsequent described event, circumstance or substituent may or may not occur, and that the description includes instances where the event or circumstance occurs and instances where it does not.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean ±1%. The present invention is further explained in detail by the following, including the Examples, but the scope of the invention should not be limited thereto.

This invention is further illustrated by the examples which should not be construed as limiting. The contents of all references cited throughout this application, as well as the figures and tables are incorporated herein by reference. All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

As used herein, "rps6" refers to ribosomal protein S6 (rpS6), a component of the 40S ribosomal subunit thought to be involved in regulating translation. While the true function of rpS6 is currently under investigation, studies have shown that it is involved in the regulation of cell size, cell proliferation, and glucose homeostasis. Studies show that the p70 ribosomal protein S6 kinases (S6K1 and S6K2) and p90 ribosomal protein S6 kinases (RSK) both phosphorylate rpS6 and that S6K1 and S6K2 predominate this function. Genebank accession, NM_001010 (See e.g., Magnuson Bl, et al. (2012). "Regulation and function of ribosomal protein S6 kinase (S6K) within mTOR signaling networks". Biochemical Journal 441 (1): 1-21).

P90S6K and P70S6K

Ribosomal s6 kinase (rsk) is a family of protein kinases. There are two subfamilies of rsk, 1) p90rsk referred to as p90S6K herein, also known as MAPK-activated protein kinase-1 (MAPKAP-K1), and 2) p70rsk referred to as p70S6K herein, also known as S6-H1 Kinase or simply S6 Kinase. Rsk is named for ribosomal protein s6, which is part of the translational machinery, but several other substrates have been identified, including other ribosomal proteins.

Cytosolic substrates of p90S6K include protein phosphatase 1; glycogen synthase kinase 3 (GSK3); L1 CAM, a neural cell adhesion molecule; Son of Sevenless, the Ras exchange factor; and Myt1, an inhibitor of cdc2, as well as others (Morten Frödin and Steen Gammeltoft. 1999. Role and regulation of 90 kDa ribosomal S6 kinase (RSK) in signal transduction. *Molecular and Cellular Endocrinology* 151 (1-2): 65-77). In certain embodiments, p90S6K activity is assessed using these substrates and phosphorylation monitored, e.g. in in vitro assays. RSKS are serine/threonine kinases and are activated by the MAPK/ERK pathway.

RSK (p90S6K) phosphorylation of SOS1 (Son of Sevenless) at Serines 1134 and 1161 creates a 14-3-3 docking site. This interaction of phospho SOS1 and 14-3-3 negatively regulates Ras-MAPK pathway. p90rsk also regulates transcription factors including cAMP response element-binding protein (CREB); estrogen receptor-α (ERα); IκBα/NF-κB; and c-Fos (Morten Frödin and Steen Gammeltoft Supra). There are several isoforms, variants, of the 90 kDa ribosomal S6 kinase (RSK), i.e. RSK1, RSK2, RSK3, and RSK 4 (the mutations of these isoforms are well known in the art, See e.g. Lara et al. 'A review of the p90-RSK family members: Common functions and isoform specificity', *Cancer Research* 73 (17) Sep. 1, 2013, OF1-8). p90S6K human protein sequences include e.g. those found in Genebank Accession numbers Q15418.2 (GI: 20178306); NP_066958.2 (GI: 19923570); NP_001305865.1 (GI: 974576789); NP_001305867.1 (GI: 974576791); NP_002944.2 (GI: 20149547); XP_005246023.1 (GI: 530361302). In certain embodiments, the inhibitor of p90S6K directly inhibits p90S6K by directly binding to p90S6K and inhibiting its kinase activity.

p70S6 Kinase (p70S6K)

Ribosomal protein S6 kinase beta-1 (S6K1), also known as p70S6 kinase (p70S6K), in humans is encoded by the RPS6KB1 gene. It is a serine/threonine kinase that acts downstream of PIP3 and phosphoinositide-dependent kinase-1 in the PI3 kinase pathway (Chung J, Grammer T C, Lemon K P, Kazlauskas A, Blenis J. (1994). "PDGF- and insulin-dependent pp70S6k activation mediated by phosphatidylinositol-3-OH kinase". *Nature*_370 (6484): 71-75; Chung J, Kuo C J, Crabtree G R, Blenis J. (1992). "Rapamycin-FKBP specifically blocks growth-dependent activation of and signaling by the 70 kd S6 protein kinases." *Cell* 69 (7): 1227-1236). mTOR is known to phosphorylate p70S6K at threonine 389 has and correlated with autophagy inhibition in various situations. In certain embodiments, inhibitors of mTor are the inhibitors of p70S6K. In alternative embodiments, the inhibitor of p70S6K directly inhibits p70S6K by directly binding to p70S6K and inhibiting its kinase activity.

Substrates of p70S6K include ribosome protein S6 as well as others. Phosphorylation of S6 induces protein synthesis at the ribosome. In certain embodiments, p70S6K activity is assessed using these substrates and phosphorylation monitored, e.g. in in vitro assays. p70S6K human protein sequences include e.g. those found in Genebank Accession numbers NP_001258971.1; NP_001258972.1; NP_001258973.1; NP_001258989.1; NP_003152.1. Reference mRNA sequences include e.g. NM_001272042; NM_001272043; NM 001272044; NM 001272060; NM_003161.

Inhibitors of p90S6K and p70S6K

Provided herein are methods for treating a subject with a ribosomal disorder or ribosomopathy, that comprise administering an effective amount of an inhibitor of ribosomal s6 kinase, RSK (p90S6k), to the subject to decrease p90S6K activity and decrease active p53 in at least one of CD34+ cells, erythroid cells or erythroid differentiated cells in the subject.

Any inhibitor of p90S6K can be used in methods of the invention. Some known inhibitors of p90S6K include for example, those described in Shiliang Li et al. "Identification of Inhibitors against p90 Ribosomal S6 Kinase 2 (RSK2) through Structure-Based Virtual Screening with the Inhibitor-Constrained Refined Homology Model" *J. Chem. Inf. Model.,* 2011, 51 (11), pp 2,939-2947, incorporated herein by reference in its entirety. Non-limiting examples of inhibitors are disclosed in the following patents and publications: U.S. Pat. No. 7,605,241, PCT./US2006/000709. Many are commercially available, e.g. Kempferol, Chemical Name: 3,5,7-Trihydroxy-2-(4-hydroxyphenyl)-4H-1-benzopyran-4-one; and BRD739, Chemical Name: 1-[(2-Phenylethyl) amino]-3H-naphtho[1,2,3-de]quinoline-2,7-dione; PF 4708671, Chemical name; 2-[[4-(5-Ethylpyrimidin-4-yl) piperazin-1-yl]methyl]-5-(trifluoromethyl)-1H-benzo[d] imidazole) and SL 0101-1 Chemical Name: 3-[(3,4-Di-O-acetyl-6-deoxy-α-L-mannopyranosyl)oxy]-5,7-dihydro-2-(4-hydroxyphenyl)-4H-1 benzopyran-4-one, which are available from Tocris Bioscience (Avonmouth, Bristol, BS11 9QD, United Kingdom); and FMK RSK inhibitor (p90 RSK specific) as described in: T L Nguyen et al. "Targeting RSK: an overview of small molecule inhibitors" *Anticancer Agents Med. Chem.* 2008, 8 (7), 710-716, and are available from e.g. Axon Medchem BV, Groningen, Netherlands.

In certain embodiments, the inhibitor of p90S6K is BI-D1870, or a derivative or analogue of BI-D1870 (BI). BI has the molecular formula (MF) $C_{18}H1_{9}FN_{4}O_{2}$ and is a potent and specific inhibitor of each of the p90 ribosomal S6 kinase (RSK) isoforms in vitro and in vivo. Thus it inhibits RSK1, RSK2, RSK3 and RSK4 in vitro (IC50 values 31 nM, 24 nM, 18 nM, and 15 nM, respectively), (available from Axon Medchem BV, Groningen, Netherlands). BI-D1870 (BI) has the following structure:

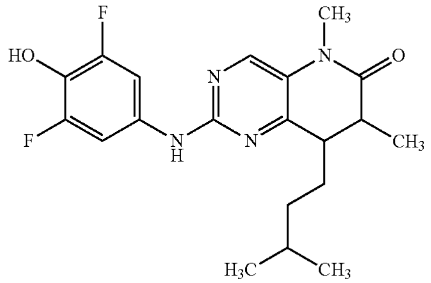

In certain embodiments, the inhibitor of p90S6k is SL0101 (SL), or a derivative or analogue of SL0101 (SL), wherein SL0101 (SL) has the following structure:

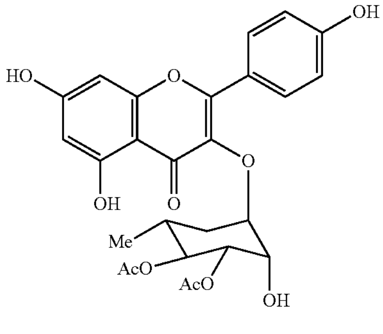 [SMILES: CC(=O)OC1C(C)CC(Oc2c(-c3ccc(O)cc3)oc3cc(O)cc(O)c3c2=O)C(O)C1OC(C)=O]

SL is a selective inhibitor of ribosomal S6 kinase (RSK) and has selectivity for RSK 2, (IC50=89 nM for RSK2). SL Does not inhibit upstream kinases such as MEK, Raf and PKC.

Also provided is a method of treating a subject with a ribosomal disorder or ribosomopathy, comprising administering an effective amount of an inhibitor of RSK (p70S6K). Any inhibitor of p70S6K can be used in methods of the invention. Some known inhibitors of p70S6K include for example, those described in Upul Bandaragea et al. "4-(Benzimidazol-2-yl)-1,2,5-oxadiazol-3-ylamine derivatives: Potent and selective p70S6 kinase inhibitors" *Bioorganic & Medicinal Chemistry Letters* 19 (17), 1 Sep. 2009, Pages 5191-5194; and rapamycin and its derivatives, and others e.g. described in Sandrine Faivre et al. "Current development of mTOR inhibitors as anticancer agents" *Nature Reviews Drug Discovery* 5, 671-688 (August 2006 each incorporated herein by reference in its entirety. Many are commercially available, e.g. PF 4708671 MF $C_{19}H_{21}F_3N_6$ RSK inhibitor (p70 RSK specific) (available from Axon Medchem BV, Groningen, Netherlands); and DG2, MF $C_{16}H_{17}BrN_6O$, a RSK inhibitor (p70 ribosomal S6 kinase 1 specific).

In certain embodiments, the inhibitor of p70S6k is PF-4708671 (PF), or a derivative or analogue of PF-4708671 (PF), wherein PF-4708671 (PF) has the following structure:

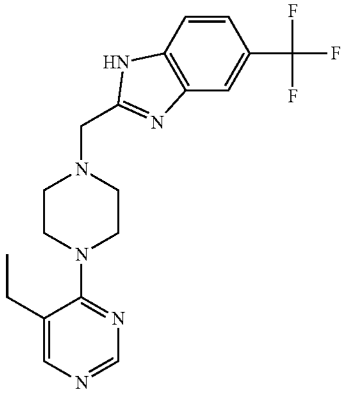 [SMILES: CCc1cncnc1N1CCN(Cc2nc3cc(C(F)(F)F)ccc3[nH]2)CC1]

The ability of a compound to inhibit the target proteins identified herein, e.g. p70S6K, p90SKs, can be assessed by measuring a decrease in kinase activity of the inhibitors as compared to the activity of the proteins in the absence of the respective inhibitor.

Other Inhibitors

Also provided is a method of treating a subject with a ribosomal disorder or ribosomopathy, comprising administering an effective amount of an inhibitor of Chk2 to the subject to decrease active p53 in at least one of CD34+ cells, erythroid cells or erythroid differentiated cells in the subject, wherein the inhibitor of Chk2 comprises a compound selected from the group consisting of CCT and III, or derivatives thereof, wherein CCT and III have the following structures:

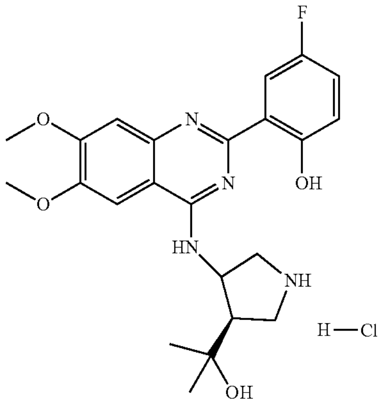

CCT

III

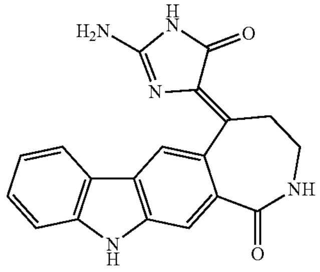

Checkpoint kinases (Chks) (e.g. Chk1 and Chk2) are serine/threonine kinases that are involved in the control of the cell cycle. They are essential components to delay cell cycle progression in normal and damaged cells and can act at all three cell cycle checkpoints.

As used herein "CCT" refers to CCT 241533 dihydrochloride, available from Tocris biosciences Supra. CCT is a potent Chk2 inhibitor (IC50=3 nM). Shows >63-fold selectivity for Chk1 over Chk2 and a panel of 84 other kinases. CCT inhibits Chk2 activation in response to etoposide-induced DNA damage in HT29 cells and blocks ionizing radiation-induced apoptosis of mouse thymocytes.

Phenothiazine Compounds

Also provided is a method of treating a subject with a ribosomal disorder or ribosomopathy, comprising administering an effective amount of an inhibitor of calmodulin to the subject to decrease active p53 in at least one of CD34+ cells, erythroid cells or erythroid differentiated cells in the subject, wherein the inhibitor of calmodulin is a phenothiazine compound, or a derivative or analogue of the phenothiazine compound, wherein the phenothiazine compound is selected from the group consisting of ACV-1-235 (ACV); JJM-II-221E (221E); and DB1026 (PerSucc) having the following structures:

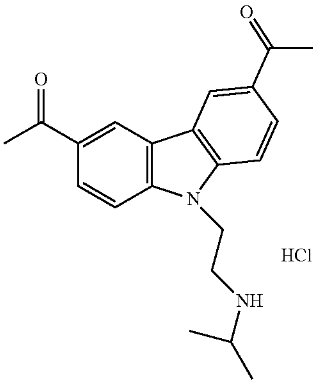

HCl

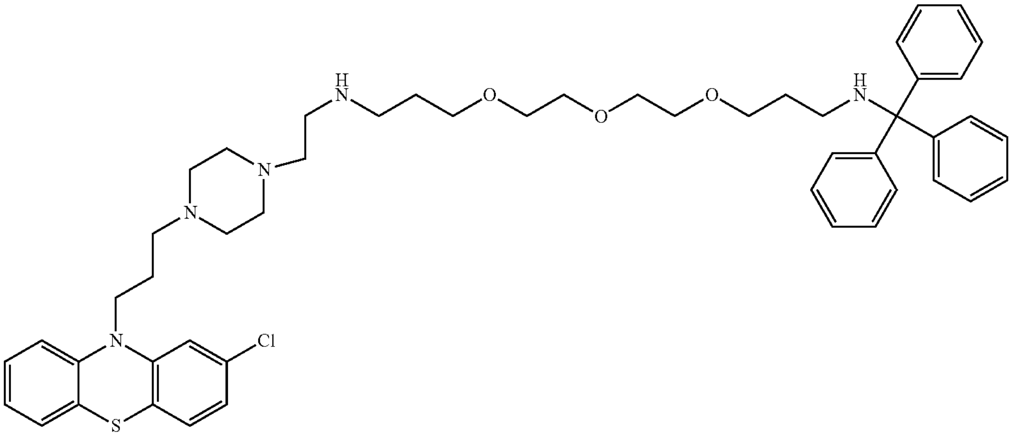

JJM-II-221E

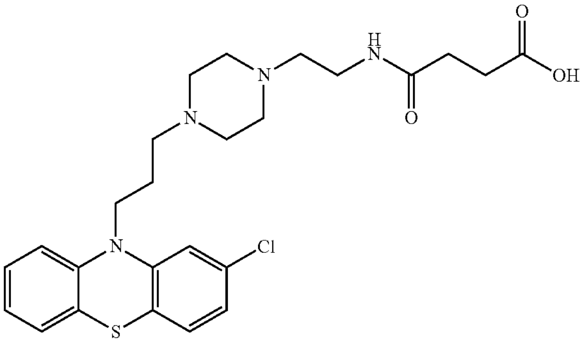

Also provided is a method of treating a subject with a ribosomal disorder or ribosomopathy, comprising administering an effective amount of an inhibitor of calmodulin to the subject to decrease active p53 in at least one of CD34+ cells, erythroid cells or erythroid differentiated cells in the subject, wherein the inhibitor of calmodulin is a phenothiazine compound, or a derivative or analogue of the phenothiazine compound, and wherein the phenothiazine compound is selected from the group consisting of DB-4-083 (083); DB-4-084 (084); DB-4-088-2 (088-2); DB-4-088-3 (088-3); DB-4-086 (086); DB-4-087-(087-2); DB-4-087-3 (087-3); DB-4-089 (089) having the following structures:

DB-4-083

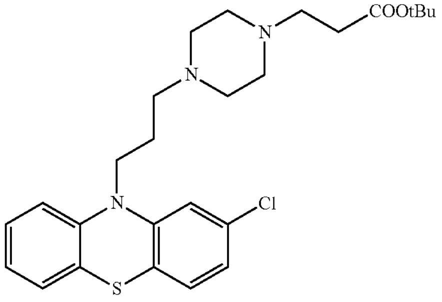

DB-4-084
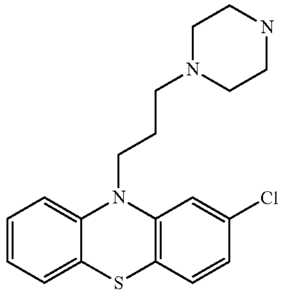
DB-4-086
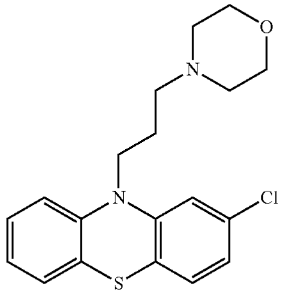
DB-4-087-2
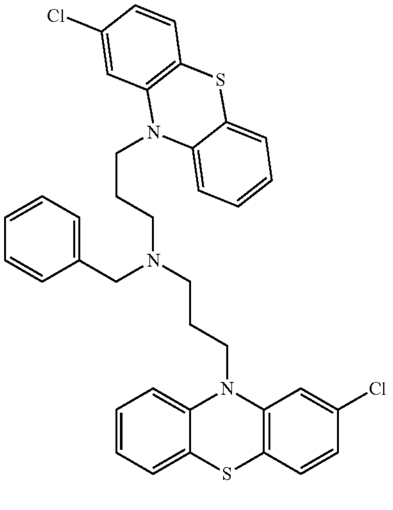
DB-4-088-2
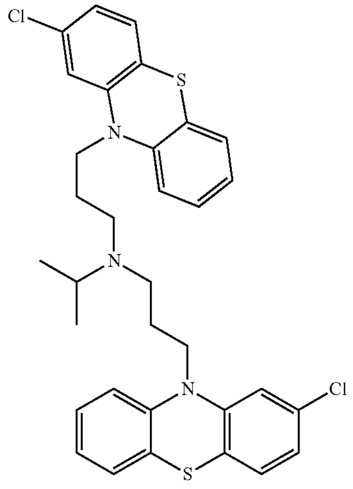
DB-4-089
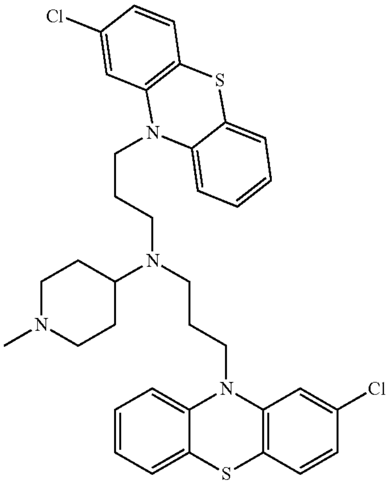
DB-4-088-3
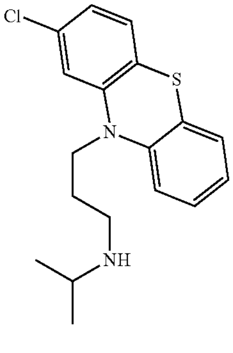

DB-4-087-3

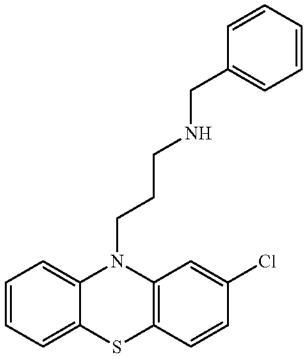

In certain embodiments, the phenothiazine compound to treat ribosomal disorders and ribosomopathies, e.g. DBA, is a compound of Formula (I):

FORMULA (I)

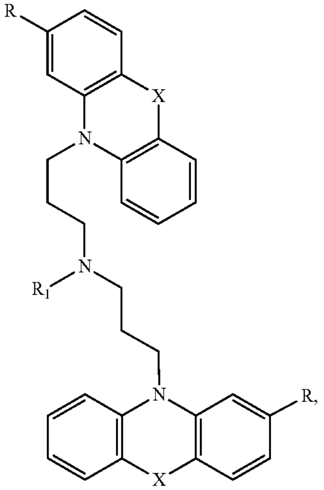

wherein:

X is O or S;

$R^1$ is H, alkyl, alkenyl, alkynyl, cyclyl, heterocyclyls, acyl, aryl, heteroaryl, alkylheteroaryl or alkylaryl;

each R is independently H, halo, alkyl, alkyl, alkenyl, alkynyl, haloalkyl, CN, OH, $NH_2$, alkylamino, dialkylamino, $CO_2H$, acyl, SH, thioalkoxy, $SO_2H$, or $SO_3H$; and isomers and pharmaceutically acceptable salts thereof.

In certain embodiments, X is S in compounds of Formula (I). In some other embodiments, X is O in compounds of Formula (I).

The $R^1$ group in compounds of Formula (I) can be selected from the group consisting of H, alkyl, cyclyl, heterocyclyls, acyl, aryl, heteroaryl, alkylheteroaryl and alkylaryl. Optionally, alkyl, cyclyl, heterocyclyls, acyl, aryl, heteroaryl, alkylheteroaryl and alkylaryl of the $R^1$ group can be substituted with 1, 2, 3 or 4 substituents.

In some embodiments, $R^1$ is a $C_1$-$C_6$ alkyl. Exemplary alkyls for the $R^1$ group include, but are not limited to methyl, ethyl, propyl, isopropyl, n-butyl, t-butyl, sec-butyl, isobutyl, pentyl and hexyl. In some embodiments, $R^1$ is isopropyl.

In still some other embodiments, $R^1$ is an optionally substituted alkylaryl, for example a $C_1$-$C_6$alkylaryl, which can be optionally substituted. Exemplary aryl for the alkylaryl of the $R^1$ group include, $C_1$-$C_6$alkylphenyl. In some embodiments, $R^1$ is benzyl.

In yet other embodiments, $R^1$ is a heterocyclyls, optionally substituted with one, two, three or four substituents. Exemplary heterocyclyls for the $R^1$ group include, but are not limited to, optionally substituted piperidinyl. In some embodiments, $R^1$ is 4-piperidinyl, optionally substituted at the N atom. For example, $R^1$ is N-methylpiperidin-4-yl.

In compounds of Formula (I), the R groups can be same or different and are independently selected from the group consisting of H, halo, alkyl, haloalkyl, CN, OH, $NH_2$, alkylamino, dialkylamino, $CO_2H$, acyl, SH, thioalkoxy, $SO_2H$, and $SO_3H$. In some embodiments, each R independently is H, halo, $C_1$-$C_6$alkyl, $C_1$-$C_6$haloalkyl, OH, $C_1$-$C_6$alkoxy, $NH_2$, $NO_2$, $C_1$-$C_6$alkylamino, di($C_1$-$C_6$alkyl)amino, CN or $CO_2H$.

In some further embodiments, each R independently is H, Cl, F, Br, methyl, trifluoromethyl, OH, $NH_2$, $NO_2$, CN or $CO_2H$.

In some embodiments of compounds of Formula (I), $R^1$ is alkyl, heterocyclyl, or alkylaryl, each of which can be optionally substituted; and each R is H, halo, alkyl or haloalkyl.

In some embodiments, the phenothiazine compound to treat ribosomal disorders and ribosomopathies, e.g. DBA, is a compound of Formula II:

FORMULA (II)

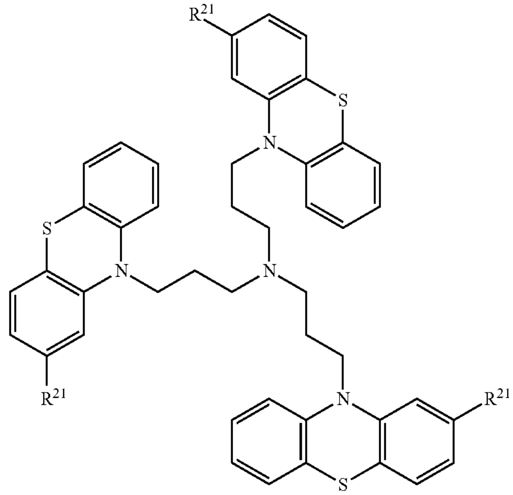

wherein:

each $R^{21}$ is independently selected from the group consisting of H, halo, alkyl, haloalkyl, CN, OH, $NH_2$, alkylamino, dialkylamino, $CO_2H$, acyl, SH, thioalkoxy, $SO_2H$, and $SO_3H$;

isomers and pharmaceutically acceptable salts thereof.

In compounds of Formula (II), all $R^{21}$ can be the same, all different or two same and one different. In some embodiments, each $R^{21}$ independently is H, halo, $C_1$-$C_6$alkyl, $C_1$-$C_6$haloalkyl, OH, $C_1$-$C_6$alkoxy, $NH_2$, $NO_2$, $C_1$-$C_6$alkylamino, di($C_1$-$C_6$alkyl)amino, CN or $CO_2H$. For example, each $R^{21}$ independently can be H, Cl, F, Br, methyl, trifluoromethyl, OH, $NH_2$, $NO_2$, CN or $CO_2H$.

In one embodiment, the phenothiazine compound to treat ribosomal disorders and ribosomopathies, e.g. DBA, is the compound of structure:

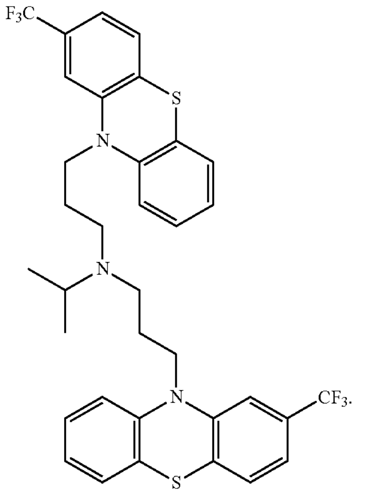 [SMILES: CC(C)N(CCCN1c2ccccc2Sc2ccc(C(F)(F)F)cc21)CCCN1c2ccccc2Sc2ccc(C(F)(F)F)cc21]

Also provided is a method of treating a subject with a ribosomal disorder or ribosomopathy, comprising administering an effective amount of the is a calcium channel blocker BAPTA-AM or derivative or analogue thereof to the subject to decrease active p53 in at least one of CD34+ cells wherein BAPTA-AM has the following structure:

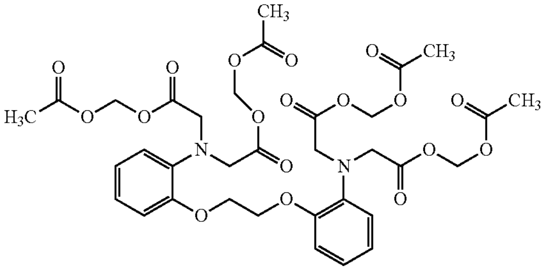 [SMILES: CC(=O)OCOC(=O)CN(CC(=O)OCOC(C)=O)c1ccccc1OCCOc1ccccc1N(CC(=O)OCOC(C)=O)CC(=O)OCOC(C)=O]

RNAi Inhibitors of p90S6K and p70S6K and rbs6

As discussed herein, the inventors have discovered that inhibition of the rsk proteins p90S6K and p70S6K and inhibitors of rps6, can be used in the methods for the treatment of ribosome protein disorders and ribosomopathy as disclosed herein. In some embodiments, the inhibitor in not a small molecule compound, but rather a protein inhibitor, and in some embodiments, the inhibitor is any nucleic acid which inhibits the function of p90S6K and p70S6K or the expression of p90S6K and p70S6K from its gene. In some embodiments, an inhibitor of p90S6K and p70S6K is a gene silencing agent.

Human p90S6K is also known by aliases; HU-1, MAPKAPK1A, RSK, RSK1, p90Rsk, 90 kDa ribosomal protein S6 kinase, 1MAP kinase-activated protein kinase, 1aMAPK-activated protein kinase 1aMAPKAP kinase, is encoded by nucleic acid sequence, chromosome 1, NC_000001.11 (26529758 . . . 26575029). One *Homo sapiens* ribosomal protein S6 kinase A2 (RPS6KA2) variant, i.e., transcript variant 1, is mRNA Genebank NM_021135.5, which is SEQ ID NO: 1 herein, and has an amino acid of SEQ ID NO: 2. Inhibition of the p90S6K gene can be by gene silencing RNAi molecules according to methods commonly known by a skilled artisan. For example, a gene silencing siRNA oligonucleotide duplexes targeted specifically to human p90S6K can readily be used to knockdown p90S6K expression. p90S6K mRNA can be successfully targeted using siRNAs; and other siRNA molecules may be readily prepared by those of skill in the art based on the known sequence of the target mRNA. Accordingly, in avoidance of any doubt, one of ordinary skill in the art can design nucleic acid inhibitors, such as RNAi (RNA silencing) agents to the nucleic acid sequence of SEQ ID NO: 1 which is as follows:

```
ORIGIN
                                                      (SEQ ID NO: 1)
  1 aggcgtggcg cgtggccggc gctggtactc gcaggggagg cggagaagga ggcggaggga

 61 gcgattgtgg ccccggccgc ggtggccggc gcggcctgcc ctttgtgacc gcagctcgcg

121 ccccacgccc cgcgcccatg gccgccgtgc cgggctccct ggccacgcgt gcccgcccgc

181 ggacctgagc cccgcgcctg ggatgccggg gatgcgcgtc ccccggccct gcggctgctc

241 cgggctgggc gcggggcgat ggacctgagc atgaagaagt tcgccgtgcg caggttcttc

301 tctgtgtacc tgcgcaggaa gtcgcgctcc aagagctcca gcctgagccg gctcgaggaa

361 gaaggcgtcg tgaaggagat agacatcagc catcatgtga aggagggctt tgagaaggca

421 gatccttccc agtttgagct gctgaaggtt ttaggacaag gatcctatgg aaaggtgttc

481 ctggtgagga aggtgaaggg gtccgacgct gggcagctct acgccatgaa ggtccttaag

541 aaagccaccc taaaagttcg ggaccgagtg agatcgaaga tggagagaga catcttggca

601 gaagtgaatc acccctcat tgtgaagctt cattatgcct ttcagacgga aggaaagctc

661 tacctgatcc tggacttcct gcggggaggg gacctcttca cccggctctc caaagaggtc

721 atgttcacgg aggaggatgt caagttctac ctggctgagc tggccttggc tttagaccat

781 ctccacagcc tggggatcat ctacagagat ctgaagcctg agaacatcct cctggatgaa
```

-continued

```
 841 gaggggcaca ttaagatcac agatttcggc ctgagtaagg aggccattga ccacgacaag
 901 agagcgtact ccttctgcgg gacgatcgag tacatggcgc ccgaggtggt gaaccggcga
 961 ggacacacgc agagtgccga ctggtggtcc ttcggcgtgc tcatgtttga gatgctcacg
1021 gggtccctgc cgttccaggg gaaggacagg aaggagacca tggctctcat cctcaaagcc
1081 aagctgggga tgccgcagtt cctcagtggg gaggcacaga gtttgctgcg agctctcttc
1141 aaacggaacc cctgcaaccg gctgggtgct ggcattgacg gagtggagga aattaagcgc
1201 catcccttct ttgtgaccat agactggaac acgctgtacc ggaaggagat caagccaccg
1261 ttcaaaccag cagtgggcag gcctgaggac accttccact ttgaccccga gttcacagcg
1321 cggacgccca cagactctcc tggcgtcccc ccgagtgcaa acgctcatca cctgtttaga
1381 ggattcagct ttgtggcctc aagcctgatc caggagccct cacagcaaga tctgcacaaa
1441 gtcccagttc acccaatcgt gcagcagtta cacgggaaca acatccactt caccgatggc
1501 tacgagatca aggaggacat cggggtgggc tcctactcag tgtgcaagcg atgtgtgcat
1561 aaagccacag acaccgagta tgccgtgaag atcattgata agagcaagag agacccctcg
1621 gaagagattg agatcctcct gcggtacggc cagcacccga acatcatcac cctcaaggat
1681 gtctatgatg atggcaagtt tgtgtacctg gtaatggagc tgatgcgtgg tggggagctc
1741 ctggaccgca tcctccggca gagatacttc tcggagcgcg aagccagtga cgtcctgtgc
1801 accatcacca agaccatgga ctacctccat tcccaggggg ttgttcatcg agacctgaag
1861 ccgagtaaca tcctgtacag ggatgagtcg gggagcccag aatccatccg agtctgcgac
1921 ttcggctttg ccaagcagct gcgcgcgggg aacgggctgc tcatgacacc ctgctacacg
1981 gccaatttcg tggccccgga ggtcctgaag cgtcaaggct atgatgcggc gtgtgacatc
2041 tggagtttgg ggatcctgtt gtacaccatg ctggcaggat ttaccccttt tgcaaatggg
2101 ccagacgata cccctgagga gattctggcg cggatcggca gtgggaagta tgccctttct
2161 gggggaaact gggactcgat atctgacgca gctaaagacg tcgtgtccaa gatgctccac
2221 gtggaccctc atcagcgcct gacggcgatg caagtgctca aacacccgtg ggtggtcaac
2281 agagagtacc tgtccccaaa ccagctcagc cgacaggacg tgcacctggt gaagggcgcg
2341 atggccgcca cctactttgc tctaaacaga acacctcagg ccccgcggct ggagcccgtg
2401 ctgtcatcca acctggctca gcgcagaggc atgaagagac tcacgtccac gcggctgtag
2461 cgggtgggac cctggcccca gcgtcccctg ccagcatcct cgtgggctca cagaccccgg
2521 cctcggagcc cgtctggcac ccagagtgac cacaagtcca gcagggaggc ggcgcccgcc
2581 ctcgccgtgt ccgtgttttc tttttcagcc ccggagaggg tcctgacctg ggggcttctc
2641 caagcctcac tgcgccagcc tccccgcccg ctctcttttc tcccaagcga aaccaaatgc
2701 gccccttcac ctcgcgtgcc cgtgcgaggc cgggggcttc tttcagagcc cgcgggtcct
2761 ctcatacatg gcttctgttt ctgccgagag atctgttttc caattatgaa gccggtcggt
2821 ttggtcagac tcccgacacc cacgtcccag gtacccggtg ggaaagtggc agtgcgaggg
2881 cgcagccatt ggtggttgca gggccccaga gggctggggt gacctggcat cccggggctc
2941 cccacgggct ggatgacggg gttggcactg tggcgtccag gaggagatgc ctggttctgc
3001 ccaaaataat ccaaagagcc gtttcctcct cgcccttcag tttttgcctg aggtgctggg
3061 tagcccatcc tttcctctgt cccagattca aatgaggagt aagagcccag acgagaggaa
3121 ggcaggctgg atctttgcct tgagagctcc gtgtcaccag gatggaaggg ggtgcctctc
3181 ggaggagcct gtgtccacct ccagtctcgg ctttccccgg ggggccaagc gcactgggct
```

-continued 3241 gccgtctgtc cccagctccc gtggccacac agctatctgg aggctttgca gggagtcgtg 3301 ggttctcgca cctgctcagc cctgtgtcgg cttcctgtgt gctcacctaa agctgtggtt 3361 ttgctgtgtt cacttcgatt tttctggtct gtggagaaac tgtgaattgg agaaatggag 3421 ctctgtggct tcccacccaa accttctcag tccagctgga ggctggaggg agacacaggc 3481 cccacccagc agactgaggg gcagaggcac aggtgggagg gcagcggaga tcagcgtgga 3541 caggagcgat gcactttgta gatgctgtgg ctttgtgttg cgttttgtgt ctctgttgca 3601 cagatctgtt ttttcacact gatccgtatt cccctgggtg tgcacacagg gcgggtgtgg 3661 ggcatttagg ccatgctgtg ctctacttca ttgagtaaaa tcgagtgaga ggttccgggc 3721 agcaggatcg acgcccagtc cagccggcag agggaacaca cgggtccttc attgtcctgt 3781 aagggtgttg aagatgctcc ctggcggccc ccaagcagac tagatgggag gaggcgccgc 3841 tcagcccctc accctgcatc actgaagagc ggcgcctctg cagcaagcag ggcttcagga 3901 ggtgcccgct ggccacagcc aggttttccc taagaagatg ttattttgtt gggttttgtt 3961 ccccctccat ctcgattctc gtacccaact aaaaaaaaaa aaataaagaa aaaatgtgct 4021 gcgttctgaa aaataactcc ttagcttggt ctgattgttt tcagacctta aaatataaac 4081 ttgtttcaca agctttaatc catgtggatt ttttttttct tagagaacca caaaacataa 4141 aaggagcaag tcggactgaa tacctgtttc catagtgccc acagggtatt cctcacattt 4201 tctccataga agatgctttt tcccaaggct agaacgactt ccaccatgat qaatttqctt 4261 tttaggtctt aattatttca cttcttttta gaaacttagg aagaagtgga taatcctgag 4321 gtcacacaat ctgtcctccc agaaatgaac aaaagtcatc accttttctg cttgctacac 4381 aggcaacgat tcccccatca gctgcccgga ccctttggcc tggcttggtg tgcaggcctg 4441 tctgtttgct taaagtcagt gggttctggt gcagggagtg agaagtgggg gaagtgaaag 4501 ggaaagcatc cgtgagaaag cggccacggt tttccctcct tgtgtgccca tggggcacca 4561 gctcatggtc tttttcagtc atcccagttt gtacagactt agcttctgaa ctctaagaat 4621 gccaaaggga ccgacgagac tccccatcac agcgagctct gtccttacat gtatttgatg 4681 tgcatcagcg gaggagaaca ctggcttggc cctgctccgc tgagtgtctg tgaaatacct 4741 ctactttccc tcccatatcc agaacaaaat gatacttgac atccttccac aaaagtcagc 4801 ctaaagaagt tatggtatca tatgttaaac taagctttca aaaaccttag tgaaatagca 4861 agtgactgct ttcaagcagc agtcgacatg taaatgaagg tgttcttaga attcgcattt 4921 tgccagctca gcgcacctcc acaacgaatg aaatgctccg tatgatttgc acaaatgaca 4981 tagacctccc caaaagttaa ctggctctcc ttcctcacac agttcatcat aacccaaccc 5041 cccacccccg ggtcatgaaa atcacagaac ttataaacac attgaaccct agatctcagg 5101 cttcctgacc taccgccagt ggccccttgc tggccaccct atagggtcct ccttccctgg 5161 cagcccccca tgtgggagaa atacctgatt ctcccaatct gcagtgggag agctttgctg 5221 aattccatcc caaagtcaaa catgggcaag aggtgaggat ttcactttta ccctcaagtc 5281 cgatttgtct gtgattttaa actaactgtg tatgtattga tgtttggaag attgtttgaa 5341 ttttaaagtg ataatagtac ttaatgttat ccagtattgt tcattaaatg gtgttatcct 5401 aaagctgcac ttgggatttt tacctaacgc tttactgatt ctctcaagca catggcaaag 5461 tttgatttgc actccgttca tttctgacac gttttgctgc ctcctacctt tctaagcgtc 5521 atgcaaattc gagaatggag aaggacgctg ccggtccctg agcggtgtgg agagggcgga 5581 aggtggactc cagcgcagct tgaggggctg aggacggagg ctgcagcatc tgtgtcgttc 5641 tactgagcac gcttctctgc ctcgctcctg actcagcact ttgttcactg gctcagcagt -continued 5701 tatgtttaca catcattttt atgttcctgc tttgtaattc atgtttgaga tgggtggcca 5761 ctgtacagat atttattacg ctttccagac tttctgaata gattttttttg aataaacatg 5821 gttttatgaa gtgtaatctt tttctagcct aacaataaaa aaaaaaaaaa a SEQ ID NO: 1 encodes the following amino acid sequence, i.e. SEQ ID NO: 2:

(SEQ ID NO: 2)

MDLSMKKFAVRRFFSVYLRRKSRSKSSSLSRLEEEGVVKEIDISHHVKE

GFEKADPSQFELLKVLGQGSYGKVFLVRKVKGSDAGQLYAMKVLKKATL

KVRDRVRSKMERDILAEVNHPFIVKLHYAFQTEGKLYLILDFLRGGDLF

TRLSKEVMFTEEDVKFYLAELALALDHLHSLGIIYRDLKPENILLDEEG

HIKITDFGLSKEAIDHDKRAYSFCGTIEYMAPEVVNRRGHTQSADWWSF

GVLMFELTGSLPFQGKDRKETMALILKAKLGMPQFLSGEAQSLLRALFK

RNPCNRLGAGIDGVEEIKRHPFFVTIDWNTLYRKEIKPPKFPAVGRPED

TFHFDPEFTARTPTDSPGVPPSANAHHLFRGFSFVASSLIQEPSQQDLH

KVPVHPIVQQLHGNNIHFTDGYEIKEDIGVGSYSVCKRCVHDATDTEYA

VKIIDKSKRDPSEEIEILLRYGQHPNIITLKDVYDDGKFVYLVMELMRG

GELLDRILRQRYFSEREADSVLCTITKTMDYLHSQGVVHRDLKPSNILY

RDESGSPESIRVCDFGFAKQLRAGNGRIGSGKYALSGGNWDSISDAAKD

-continued

VVSKMLHVDPHQRLTAMQVLKHPWVVNREYLSPNQLSRQDVHLVKGAMA

ATYFALNRTPQAPRLEPVLSSNLAQRRGMKRLTSTRL

Human p70S6K is also known by aliases; p70 S6KA; p70(S6K)-alpha; p70-alpha; p70-S6K; PS6K; S6K; S6K-beta-1; S6K1; STK14A; and RPS6KB1 and is encoded by e.g. Homo sapiens ribosomal protein S6 kinase B1 (RPS6KB1), transcript variant 1, mRNA Accession: NM_001272060.1 GI: 440546415 nucleic acid sequence (SEQ ID NO: 3), and has an amino acid of (SEQ ID NO: 4). Inhibition of the p70S6K gene can be by gene silencing RNAi molecules according to methods commonly known by a skilled artisan. For example, a gene silencing siRNA oligonucleotide duplexes targeted specifically to human p70S6K can readily be used to knockdown p70S6K expression. p70S6K mRNA can be successfully targeted using siRNAs; and other siRNA molecules may be readily prepared by those of skill in the art based on the known sequence of the target mRNA. Accordingly, in avoidance of any doubt, one of ordinary skill in the art can design nucleic acid inhibitors, such as RNAi (RNA silencing) agents to the nucleic acid sequence of NM_001272060 which is as follows:

(SEQ ID NO: 3)

1 gtttggcttc acggaaccct gtacgcatgc tcctacgctg aactttagga gccagtctaa 61 ggcctaggcg cagacgcact gagcctaagc agccggtgat ggcggcagcg gctgtggtgg 121 ctgcggcggg tccgggccca tgaggcgacg aaggaggcgg gacggctttt acccagcccc 181 ggacttccga gacagggaag ctgaggacat ggcaggagtg tttgacatag acctggacca 241 gccagaggac gcgggctctg aggatgagct ggaggagggg ggtcagttaa atgaaagcat 301 ggaccatggg ggagttggac catatgaact tggcatggaa cattgtgaga aatttgaaat 361 ctcagaaact agtgtgaaca gagggccaga aaaaatcaga ccagaatgtt ttgagctact 421 tcgggtactt ggtaaagggg gctatggaaa ggtttttcaa gtacgaaaag taacaggagc 481 aaatactggg aaaatatttg ccatgaaggt gcttaaaaag gcaatgatag taagaaatgc 541 taaagataca gctcatacaa aagcagaacg gaatattctg gaggaagtaa agcatccctt 601 catcgtggat ttaatttatg cctttcagac tggtggaaaa ctctacctca tccttgagta 661 tctcagtgga ggagaactat ttatgcagtt agaaagagag ggaatattta tggaagacac 721 tgcctgcttt tacttggcag aaatctccat ggctttgggg catttacatc aaaaggggat 781 catctacaga gacctgaagc cggagaatat catgcttaat caccaaggtc atgtgaaact 841 aacagacttt ggactatgca aagaatctat tcatgatgga acagtcacac acacattttg 901 tggaacaata gaatacatgg cccctgaaat cttgatgaga agtggccaca atcgtgctgt 961 ggattggtgg agtttgggag cattaatgta tgacatgctg actggagcac ccccattcac 1021 tggggagaat agaaagaaaa caattgacaa aatcctcaaa tgtaaactca atttgcctcc 1081 ctacctcaca caagaagcca gagatctgct taaaaagctg ctgaaaagaa atgctgcttc 1141 tcgtctggga gctggtcctg gggacgctgg agaagttcaa gctcatccat tctttagaca -continued

```
1201 cattaactgg gaagaacttc tggctcgaaa ggtggagccc ccctttaaac ctctgttgca
1261 atctgaagag gatgtaagtc agtttgattc caagtttaca cgtcagacac ctgtcgacag
1321 cccagatgac tcaactctca gtgaaagtgc caatcaggtc tttctgggtt ttacatatgt
1381 ggctccatct gtacttgaaa gtgtgaaaga aaagttttcc tttgaaccaa aaatccgatc
1441 acctcgaaga tttattggca gcccacgaac acctgtcagc ccagtcaaat tttctcctgg
1501 ggatttctgg ggaagaggtg cttcggccag cacagcaaat cctcagacac ctgtggaata
1561 cccaatggaa acaagtggca tagagcagat ggatgtgaca atgagtgggg aagcatcggc
1621 accacttcca atacgacagc cgaactctgg gccatacaaa aaacaagctt ttcccatgat
1681 ctccaaacgg ccagagcacc tgcgtatgaa tctatgacag agcaatgctt ttaatgaatt
1741 taaggcaaaa aaggtggaga gggagatgtg tgagcatcct gcaaggtgaa acgactcaaa
1801 atgacagttt cagagagtca atgtcattac atagaacact tcagacacag gaaaaataaa
1861 cgtggatttt aaaaaatcaa tcaatggtgc aaaaaaaaac ttaaagcaaa atagtattgc
1921 tgaactctta ggcacatcaa ttaattgatt cctcgcgaca tcttctcaac cttatcaagg
1981 attttcatgt tgatgactcg aaactgacag tattaagggt aggatgttgc ttctgaatca
2041 ctgttgagtt ctgattgtgt tgaagaaggg ttatcctttc attaggcaaa gtacaaaatt
2101 gcctataata cttgcaacta aggacaaatt agcatgcaag cttggtcaaa ctttttccag
2161 caaaatggaa gcaaagacaa aagaaactta ccaattgatg ttttacgtgc aaacaacctg
2221 aatctttttt ttatataaat atatattttt caaatagatt tttgattcag ctcattatga
2281 aaaacatccc aaactttaaa atgcgaaatt attggttggt gtgaagaaag ccagacaact
2341 tctgtttctt ctcttggtga aataataaaa tgcaaatgaa tcattgttaa ccacagctgt
2401 ggctcgtttg agggattggg gtggacctgg ggtttatttt cagtaaccca gctgcaatac
2461 ctgtctgtaa tatgagaaaa aaaaaatgaa tctatttaat catttctact tgcagtactg
2521 ctatgtgcta agcttaactg gaagccttgg aatgggcata agttgtatgt cctacatttc
2581 atcattgtcc cgggcctgca ttgcactgga aaaaaaaatc gccacctgtt cttacaccag
2641 tatttggttc aagacaccaa atgtcttcag cccatggctg aagaacaaca gaagagagtc
2701 aggataaaaa atacatactg tggtcggcaa ggtgagggag atagggatat ccaggggaag
2761 agggtgttgc tgtggcccac tctctgtcta atctctttac agcaaattgg taagattttc
2821 agttttactt ctttctactg tttctgctgt ctaccttcct tatatttttt tcctcaacag
2881 ttttaaaaag aaaaaaaggt ctattttttt ttctcctata cttgggctac atttttttgat
2941 tgtaaaaata tttgatggcc ttttgatgaa tgtcttccac agtaaagaaa acttagtggc
3001 ttaatttagg aaacatgtta acaggacact atgtttttga aattgtaaca aaatctacat
3061 aaatgattta caggttaaaa gaataaaaat aaaggtaact ttacctttct taaatatttc
3121 ctgccttaaa gagagcattt ccatgacttt agctggtgaa agggtttaat atctgcagag
3181 ctttataaaa atatatttca gtgcatactg gtataataga tgatcatgca gttgcagttg
3241 agttgtatca cctttttttgt ttgtctttta taatgtcttc agtctgagtg tgcaaagtca
3301 atttgtaata ttttgcaacc ctaggatttt tttaaataga tgctgcttgc tatgttttca
3361 aaccttttttg agccatagga tccaagccat aaaattcttt atgcatgttg aattcagtca
3421 gaaaagagca aggctttgct ttttgaaatt gcaactcaaa tgagatggga tgaaatccta
3481 tgacagtaag caaaaacaga accatgaaaa atgattggac atacaccttt tcaattgtgg
3541 caataattga aagaatcgat aaaagttcat ctttggacag aaagccttta aaaaaaaaat
```

-continued

```
3601 cactccctct tccccctcct cccttattgc agcagcctac tgagaacttt gactgttgct
3661 ggtaaattag aagctacaat aataattaag ggcagaaatt atacttaaaa agtgcagatc
3721 cttgttcttt gacaatttgt gatgtctgaa aaaacagaac ccgaaaagct atggtgatat
3781 gtacaggcat tatttcagac tgtaaatggc ttgtgatact cttgatactt gttttcaaat
3841 atgtttacta actgtagtgt tgactgcctg accaaattcc agtgaaactt atacaccaaa
3901 atattcttcc taggtcctat ttgctagtaa catgagcact gtgattggct ggctataacc
3961 accccagtta aaccattttc ataattagta gtgccagcaa tagtggcaaa cactgcaact
4021 tttctgcata aaaagcatta attgcacagc taccatccac acaaatacat agtttttctg
4081 acttcacatt tattaagtga aatttatttc ccatgctgtg gaaagtttat tgagaacttg
4141 tttcataaat ggatatccct actatgactg tgaaaacatg tcaagtgtca cattagtgtc
4201 acagacagaa agcacacacc tatgcaatat ggcttatcta tatttatttg taaaaatcca
4261 agcatagttt aaaatatgat gtcgatatta ctagtcttga gtttctaaga gggttcttta
4321 tgttatacca ggtaagtgta taaaagagat taagtgcttt tttttcatca cttgattatt
4381 ttctttaaaa tcagctatta caggatattt ttttatttta tacatgctgt tttttaatta
4441 aaatataatc actgaagttt actaatttga ttttataagg tttgtagcat tacagaataa
4501 ctaaactggg atttataaac cagctgtgat taacaatgta aagtattaat tattgaactt
4561 tgaaccagat ttttaggaaa attatgttct ttttcccccct ttatggtctt aactaatttg
4621 aatccttcaa gaaggatttt tccatactat tttttaagat agaagataat ttgtgggcag
4681 gggtggagga tgcatgtatg atactccata aattcaacat tctttactat aggtaatgaa
4741 tgattataaa caagatgcat cttagatagt attaatatac tgagccttgg attatatatt
4801 taatatagga cctattttga atattcagtt aatcatatgg ttcctagctt acaagggcta
4861 gatctaagat tattcccatg agaaatgttg aatttatgaa gaatagattt taaggctttg
4921 aaaatggtta atttctcaaa aacatcaatg tccaaacatc taccttttttt catagggagta
4981 gacactagca agctggacaa actatcacaa aagtatttgt cacacataac ctgtggtctg
5041 ttgctgatta atacagtact ttttcttgtg tgattcttaa cattatagca caagtattat
5101 ctcagtggat tatccggaat aacatctgaa agatgggttc atctatgttt gtgtttgctc
5161 tttaaactat tgtttctcct atcccaagtt cgctttgcat ctatcagtaa ataaaattct
5221 tcagctgcct tattaggagt gctatgaggg taacacctgt tctgcttttc atcttgtatt
5281 tagttgactg tattatttga tttcggattg aatgaatgta aatagaaatt aaatgcaaat
5341 ttgaatgaac ataaaaaaaaa aaaaaaaa
```

SEQ ID NO: 3 encodes SEQ ID NO: 4, which is as follows:

```
                                    (SEQ ID NO: 04)
MAGVFDIDLDQPEDAGSEDELEEGGQLNESMDHGGVGPYELGMEHCEKF

EISETSVNRGPEKIRPECFELLRVLGKGGYGKVFQVRKVTGANTGKIFA

MKVLKKAMIVRNAKDTAHTKAERNILEEVKHPFIVDLIYAFQTGGKLYL

ILEYLSGGELFMQLEREGIFMEDTACFYLAEISMALGHLHQKGIIYRDL

KPENIMLNHQGHVKLTDFGLCKESIHDGTVTHTFCGTIEYMAPEILMRS

GHNRAVDWWSLGALMYDMLTGAPPFTGENRKKTIDKILKCKLNLPPYLT

QEARDLLKKLLKRNAASRLGAGPGDAGEVQAHPFFRHINWEELLARKVE
```

-continued

```
PPFKPLLQSEEDVSQFDSKFTRQTPVDSPDDSTLSESANQVFLGFTYVA

PSVLESVKEKFSFEPKIRSPRRFIGSPRTPVVSPKFSPGDFWGRGASAS

TANPQTPVEYPMETSGIEQMDVTMSGEASAPLPIRQPNSGPYKKQAFPM

ISKRPEHLRMNL.
```

In certain embodiments, rps6 is inhibited. Inhibition of the rps6 gene can be by gene silencing RNAi molecules according to methods commonly known by a skilled artisan. For example, a gene silencing siRNA oligonucleotide duplexes targeted specifically to human rps6 (GenBank No: NM_001010.2) can readily be used to knockdown rps6 expression. Rps6 mRNA can be successfully targeted using siRNAs; and other siRNA molecules may be readily prepared by those of skill in the art based on the known sequence of the target mRNA. Accordingly, in avoidance of any doubt, one of ordinary skill in the art can design nucleic acid inhibitors, such as RNAi (RNA silencing) agents to the nucleic acid sequence of SEQ ID NO: 5 which is as follows:

```
                                                      (SEQ ID NO: 5)
  1 cctcttttcc gtggcgcctc ggaggcgttc agctgcttca agatgaagct gaacatctcc

 61 ttcccagcca ctggctgcca gaaactcatt gaagtggacg atgaacgcaa acttcgtact

121 ttctatgaga agcgtatggc cacagaagtt gctgctgacg ctctgggtga agaatggaag

181 ggttatgtgg tccgaatcag tggtgggaac gacaaacaag gtttccccat gaagcagggt

241 gtcttgaccc atggccgtgt ccgcctgcta ctgagtaagg ggcattcctg ttacagacca

301 aggagaactg gagaaagaaa gagaaaatca gttcgtggtt gcattgtgga tgcaaatctg

361 agcgttctca acttggttat tgtaaaaaaa ggagagaagg atattcctgg actgactgat

421 actacagtgc ctcgccgcct gggccccaaa agagctagca gaatccgcaa acttttcaat

481 ctctctaaag aagatgatgt ccgccagtat gttgtaagaa agcccttaaa taaagaaggt

541 aagaaaccta ggaccaaagc acccaagatt cagcgtcttg ttactccacg tgtcctgcag

601 cacaaacggc ggcgtattgc tctgaagaag cagcgtacca agaaaaataa agaagaggct

661 gcagaatatg ctaaactttt ggccaagaga atgaaggagg ctaaggagaa gcgccaggaa

721 caaattgcga agagacgcag actttcctct ctgcgagctt ctacttctaa gtctgaatcc

781 agtcagaaat aagatttttt gagtaacaaa taaataagat cagactctg.
```

Of course on of skill in the art will understand that other variants of these exemplified nucleic acid sequences can be targeted.

One of skill in the art will understand that an inhibitor of p90S6K and p70S6K, or rps6, can be any agent which inhibits the function of p90S6K and p70S6K, such as antibodies, gene silencing RNAi molecules and the like. Commercial neutralizing antibodies and fragments of antibodies against p90S6K, p70S6K, and rps6, are encompassed for use in the methods and compositions as disclosed herein.

A person skilled in the art is able to test whether a certain compound acts as a p90S6K and p70S6K inhibitor. Test systems for p90S6K and p70S6K activity of certain compounds are well known in the art. For instance, such test systems are described in Roux et al. 'Phosphorylation of p90 Ribosomal S6 Kinase (RSK) Regulates Extracellular Signal-Regulated Kinase Docking and RSK Activity' *Mol Cell Biol.* 2003 July; 23 (14): 4796-4804; and Sapkota et al. 'BI-D1870 is a specific inhibitor of the p90 RSK (ribosomal S6 kinase) isoforms in vitro and in vivo' *Biochem J.* 2007 Jan. 1; 401 (Pt 1): 29-38. See also, Masuda-Robens et al. 'Assays for monitoring p70 S6 kinase and RSK activation'. *Methods Enzymol.* 2001; 333:45-55. There are also commercial assays available in the art, e.g. p70 S6K activity kit-ADI-EKS-470-Enzo Life Sciences (Farmingdale, NY); and p70 S6K Activity Kit (ab139438) from Abcam (Cambridge, MA).

In addition, as described herein, the ability to rescue at least one of the morphological, hematopoietic or endothelial defects in the Rps29−/− zebrafish embryo and/or prevent p53 function and nuclear accumulation in A549 lung cancer cell line that have had RPS19 knocked down by siRNA, or reduce p21 levels or increase erythroid markers in CD34+ cells that have had RPS19 knocked down by siRNA is a means for monitoring activity of the inhibitors of p90S6K and p70S6K.

In some embodiments, the specific calmodulin inhibitor as disclosed herein (e.g. the phenothiazine derivatives of FIG. 24 or FIG. 33, or PerSucc, or 221E, or ACV of FIG. 32, or the compounds of Formula I and formula II and analogues or derivative thereof can be assessed by one of ordinary skill in the art using assays well known in the art, for example, inhibition of calmodulin may, inter alia, be determined in the following in vitro assay, which measured the calmodulin-dependent activation of myosin light chain kinase (MLCK). Activated MLCK phosphorylates chicken gizzard myosin light chain. If calmodulin is inhibited the rate of myosin light chain phosphorylation is reduced. To test this, the following experiment is carried out (according to Itoh et al. Biochem. Pharm. 1986, 35:217-220). The reaction mixture (0.2 ml) contains 20 mM Tris-HCI (pH 7.5), 0.05 mM [γ-32P] ATP (1 μCi/assay tube), 5 mM MgCI2, 10 μM myosin light chain, 24 nM calmodulin and 0.1 mM CaCI2. MLCK (specific activity: 4.5 moles/min/mg) concentration from chicken gizzard is 0.1 μg/ml. The incubation is carried out at 30° C. for 4 min. The reaction is terminated by addition of 1 ml of 20% trichloroacetic acid. Then 0.1 ml of bovine serum albumin (1 mg/ml) is added to the reaction mixture. The sample is then centrifuged for 10 min, the pellet is resuspended in 5% trichloroacetic acid. The final pellet is dissolved in 2 ml of 1 N NaOH and the radioactivity measured in a liquid scintillation counter. Trypsin-treated MLCK can be prepared as described in Itoh et al. J Pharmacol. Exp. Ther. 1984, 230, p 737. The reaction is initiated by the addition of the ATP and is carried out in the presence of the potential inhibitors or—as a control—in the presence of their solvent. Different concentrations of the compounds will be tested in the above assay. The concentration of the compound which results in 50% decrease of kinase activity will be the IC50 concentration.

In some embodiments, a p90S6K and p70S6K inhibitor, rps6, or the specific Chk2 inhibitors and Cam inhibitors as disclosed herein can inhibit or decrease the activity of the indicated RSK, rps6, Chk2 or Cam by at least about 10%, relative to the activity level in the absence of inhibitors e.g., at least about 15%, at least about 20%, at least about 30%, at least about 40%, at least about 50%, at least about 60%, at least about 70%, at least about 80%, at least about 90%, 95%, 99% or even 100%. In certain embodiments, inhibitors as disclosed herein can decrease expression of the respective protein by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of the inhibitor.

The expression of p90S6K and p70S6K or Chk2 or Cam or rps6 includes the amount of respective RNA transcribed from a gene, that encodes the protein, and/or the amount of the amount of protein that is obtained by translation of RNA transcribed from a gene. For example, a p90S6K and p70S6K inhibitor as disclosed herein can inhibit expression of p90S6K, p70S6K, Chk2, or Cam or rps6 by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of the inhibitor.

Additionally, ability of a compound to inhibit p90S6K and p70S6K, can be also assessed by measuring a decrease in or an inhibition of biological kinase activity as compared to a negative control, e.g. the experimental condition in the absence of the inhibitors. Accordingly, a p90S6K and p70S6K inhibitor as disclosed herein can inhibit biological kinase activity of p90S6K and p70S6K, by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of the inhibitor.

In some embodiments, the ability of the inhibitors to inhibit p90S6K or p70S6K, rps6, or Chk2, or Cam, is assessed by rescuing least one of the morphological, hematopoietic or endothelial defects in the Rps29−/− zebrafish embryo and/or prevent p53 function and nuclear accumulation in A549 lung cancer cell line that have had RPS19 knocked down by siRNA, or reduce p21 levels or increase erythroid markers in CD34+ cells that have had RPS19 knocked down by siRNA as demonstrated in the Examples herein, as compared to a reference condition without treatment with such inhibitor.

The dosages of inhibitor to be administered can be determined by one of ordinary skill in the art depending on the clinical severity of the disease, the age and weight of the patient, the exposure of the patient to conditions that may precipitate outbreaks of psoriasis, and other pharmacokinetic factors generally understood in the art, such as liver and kidney metabolism. The interrelationship of dosages for animals of various sizes and species and humans based on $mg/m^3$ of surface area is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the therapeutic response. Doses can be divided and administered on a daily basis or the dose can be reduced proportionally depending on the therapeutic situation.

Typically, these drugs will be administered orally, and they can be administered in conventional pill or liquid form. If administered in pill form, they can be administered in conventional formulations with excipients, fillers, preservatives, and other typical ingredients used in pharmaceutical formations in pill form. Typically, the drugs are administered in a conventional pharmaceutically acceptable formulation, typically including a carrier. Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

The pharmaceutically acceptable formulation can also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the inhibitor disclosed herein and other ingredients.

The drugs can also be administered in liquid form in conventional formulations, that can include preservatives, stabilizers, coloring, flavoring, and other generally accepted pharmaceutical ingredients. Typically, when the drugs are administered in liquid form, they will be in aqueous solution. The aqueous solution can contain buffers, and can contain alcohols such as ethyl alcohol or other pharmaceutically tolerated compounds.

Alternatively, the drugs can be administered by injection by one of several routes well known in the art. It is, however, generally preferred to administer the drugs orally.

The drugs can be administered from once per day to up to at least five times per day, depending on the severity of the disease, the total dosage to be administered, and the judgment of the treating physician. In some cases, the drugs need not be administered on a daily basis, but can be administered every other day, every third day, or on other such schedules. However, it is generally preferred to administer the drugs daily.

In some embodiments, prodrugs of inhibitors disclosed herein also fall within the scope of the invention. As used herein, a "prodrug" refers to a compound that can be converted via some chemical or physiological process (e.g., enzymatic processes and metabolic hydrolysis) to a functionally active inhibitor (e.g. inhibitors of rps6; p90S6k or p70S6k inhibitors; or the RSk p90 inhibitors SL, or B1; p70s6K inhibitor PF; Cam inhibitor, TF and FLU; Ca2+ Chelator BABTA; chk2 inhibitors CCT and III, and the inhibitors PerSuc, 221E and ACV; or e.g. the inhibitors of FIG. 33, or the compounds of Formula I or Formula II.

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5 (4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11,:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.,* 15 (2): 143-53 (1990); Balimane and Sinko, "Involvement of multiple transporters in the oral absorption of nucleoside analogues", *Adv. Drug Delivery Rev.,* 39 (1-3): 183-209 (1999); Browne, "Fosphenytoin (Cerebyx)", *Clin. Neuropharmacol.* 20 (1): 1-12 (1997); Bundgaard, "Bioreversible derivatization of drugs—principle and applicability to improve the therapeutic effects of drugs", *Arch. Pharm. Chemi* 86 (1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8 (1): 1-38 (1992); Fleisher et al. "Improved oral drug delivery: solubility limitations overcome by the use of prodrugs", Arfv. *Drug Delivery Rev.* 19 (2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.,* 72 (3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.,* 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Prodrug, molecular structure and percutaneous delivery", *Des. Biopharm. Prop. Prodrugs Analogs.* [*Symp.*] Meeting Date 1976, 409-21. (1977); Nathwani and Wood, "Penicillins: a current review of their clinical pharmacology and therapeutic use", *Drugs* 45 (6): 866-94 (1993); Sinhababu and Thakker, "Prodrugs of anticancer agents", *Adv. Drug Delivery Rev.* 19 (2): 241-273 (1996); Stella et al., "Prodrugs. Do they have advantages in clinical practice?", *Drugs* 29 (5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39 (1-3): 117-151 (1999); Taylor, "Improved passive oral drug delivery via prodrugs", *Adv. Drug Delivery Rev.,* 19 (2): 131-148 (1996); Valentino and Borchardt, "Prodrug strategies to enhance the intestinal absorption of peptides", *Drug Discovery Today* 2 (4): 148-155 (1997); Wiebe and Knaus, "Concepts for the design of anti-HIV nucleoside prodrugs for treating cephalic HIV infection", *Adv. Drug Delivery Rev.:* 39 (1-3): 63-80 (1999); Waller et al., "Prodrugs", *Br. J. Clin. Pharmac.* 28: 497-507 (1989), content of all of which is herein incorporated by reference in its entirety.

The inhibitors disclosed herein also include pharmaceutically acceptable salts thereof. As used herein, the term "pharmaceutically-acceptable salts" refers to the conventional nontoxic salts or quaternary ammonium salts of the inhibitors as disclosed herein, e.g., from non-toxic organic or inorganic acids. These salts can be prepared in situ in the administration vehicle or the dosage form manufacturing process, or by separately reacting an inhibitor in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Treatment of Ribosomal Disorders and Ribosomopathies

In some embodiments, the inhibitors as disclosed herein can be used to treat various disease and disorders associated with ribosomal proteins or ribosomopathies. For instance, the inhibitors can be used to treat a subject who has a mutation in one or more ribosomal proteins, or have a decreased level of the ribosomal protein.

In some embodiments, the inhibitors as disclosed herein can be used in a method of treating a subject with a ribosomal disorder such as Diamond Blackfan Anemia (DBA). There are a variety of types of Diamond Blackfan anemia, for example, where the subject has DBA1, DBA2, DBA3, DBA4, DBA5, DBA6, DBA7, or DBA8. Diamond Blackfan anemia (DBA), also known as Blackfan-Diamond anemia and Inherited erythroblastopenia, is a congenital erythroid aplasia that usually presents in infancy. DBA patients have low red blood cell counts (anemia). The rest of their blood cells (the platelets and the white blood cells) are normal. This is in contrast to Shwachman-Bodian-Diamond syndrome, in which the bone marrow defect results primarily in neutropenia, and Fanconi anemia, where all cell lines are affected resulting in pancytopenia. A variety of other congenital abnormalities may also occur. Diamond Blackfan anemia is characterized by anemia (low red blood cell counts) with decreased erythroid progenitors in the bone marrow. This usually develops during the neonatal period. About 47% of affected individuals also have a variety of congenital abnormalities, including craniofacial malformations, thumb or upper limb abnormalities, cardiac defects, urogenital malformations, and cleft palate. Low birth weight and generalized growth delay are sometimes observed. DBA patients have a modest risk of developing leukemia and other malignancies.

Typically, a diagnosis of DBA is made through a blood count and a bone marrow biopsy. A diagnosis of DBA is made on the basis of anemia, low reticulocyte (immature red blood cells) counts, and diminished erythroid precursors in bone marrow. Features that support a diagnosis of DBA include the presence of congenital abnormalities, macrocytosis, elevated fetal hemoglobin, and elevated adenosine deaminase levels in red blood cells. Most patients are diagnosed in the first two years of life. However, some mildly affected individuals only receive attention after a more severely affected family member is identified. About 20-25% of DBA patients may be identified with a genetic test for mutations in the RPS19 gene. Approximately 10-25% of DBA cases have a family history of disease, and most pedigrees suggest an autosomal dominant mode of inheritance.

Accordingly, in some embodiments, the inhibitors as disclosed herein can be used in a method of treating a subject that has a mutation in ribosomal protein 19 (RPS19). The phenotype of DBA patients indicates a hematological stem cell defect specifically affecting the erythroid progenitor population. The RPS19 protein is involved in the production of ribosomes. Disease features may be related to the nature of RPS19 mutations. The disease is characterized by dominant inheritance, and therefore arises due to a partial loss of RPS 19 protein function. I In alternative embodiments, the inhibitors as disclosed herein can be used in a method of treating a subject with a mutation in ribosomal protein from at least one of, but not limited to RPS7, RPS10, RPS19, RPS24, PRS26, RPS17, PRS27L RPS29, RPL35A, PRL5 and PPL11. For example, a mutation or variant in RPS19 causes DBA1, and a mutation or variant in RPS24 causes DBA3, a mutation or variant in RPS17 causes DBA4, a mutation or variant in RPS34A causes DBA5, a mutation or variant in RPL5 causes DBA6, a mutation or variant in RPL11 causes DBA7, and a mutation or variant in RPS7 causes DBA8.

In some embodiments, a subject with a ribosomal disorder has a mutation in a ribosomal protein selected from the group consisting of: rPL2A, rPL2B, rPL3, rpL4A, rPL4B, rPL7A, rPL7B, rPL10, rPL11, rPL16A, rPL17A, rPL17B, rPL18A, rPL18B, Rpl19A, rPL19, rPL25, rPL29, rpL31A, rpL31B, rPL36A, rPL40A, rPS1A, rPS6A, rPS6B, rPS14A, rPS15, rPS19, rPS23B, rPS25A, rPS26B, rPS29, rPS29B and rPS31.

In some embodiments of all aspects of the present invention, the method further comprises administering another therapeutic agent to treat the ribosomal protein defect, selected from the group consisting of: corticosteroids, blood transfusions and bone marrow transplants and other treatments known to persons of ordinary skill in the art. Corticosteroids can be used to treat anemia in DBA. Blood transfusions can also be used to treat severe anemia in DBA. Periods of remission may occur, during which transfusions and steroid treatments are not required. Bone marrow transplantation (BMT) can cure hematological aspects of DBA, adverse events in transfusion patients can occur (Diamond Blackfan Anemia Foundation; Pospisilova D et al., (2007). "Successful treatment of a Diamond-Blackfan anemia patient with amino acid leucine.". Haematologica 92 (5): e66.)

In some embodiments of all aspects of the present invention, inhibitors are administered to the subject increases the number of CD71+ erythroid cells in the subject and/or increases hemoglobin levels in the subject.

In some embodiments of all aspects of the present invention, the methods and inhibitors and as disclosed herein can be used to treat a subject with a ribosomal disorder, such as DBA has a symptom of macrocytic anemia and/or craniofacial abnormalities.

In another embodiment, an inhibitor as disclosed herein can be used in a method of treating a subject with a ribosomal disorder such as myelodysplasia, for example, but not limited to 5q-myelodysplasia. Myelodysplasia or myelodysplastic syndromes (MDS, formerly known as preleukemia) are a diverse collection of hematological (blood-related) medical conditions that involve ineffective production (or dysplasia) of the myeloid class of blood cells, and where the bone marrow does not function normally and produces insufficient number of normal blood cells.

Patients with MDS often develop severe anemia and require frequent blood transfusions. In most cases, the disease worsens and the patient develops cytopenias (low blood counts) caused by progressive bone marrow failure. In about one third of patients with MDS, the disease transforms into acute myelogenous leukemia (AML), usually within months to a few years.

The myelodysplastic syndromes are all disorders of the stem cell in the bone marrow. In MDS, hematopoiesis (blood production) is disorderly and ineffective. The number and quality of blood-forming cells decline irreversibly, further impairing blood production.

MDS affects the production of any, and occasionally all, types of blood cells including red blood cells, platelets, and white blood cells (cytopenias). About 50 percent of pediatric myelodysplasia can be classified in five types of MDS: refractory anemia, refractory anemia with ring sideroblasts, refractory anemia with excess blasts, refractory anemia with excess blasts in transformation, and chronic myelomonocytic leukemia. The remaining 50 percent typically present with isolated or combined cytopenias such as anemia, leucopenia and/or thrombocytopenia (low platelet count). Although chronic, MDS progresses to become acute myeloid leukemia (AML) in about 30 percent of patients.

The median age at diagnosis of a MDS is between 60 and 75 years; a few patients are younger than 50; MDS diagnoses are rare in children. Males are slightly more commonly affected than females. Signs and symptoms are nonspecific and generally related to the blood cytopenias include, but are not limited to:

(a) Anemia (low RBC count or reduced hemoglobin)—chronic tiredness, shortness of breath, chilled sensation, sometimes chest pain
(b) Neutropenia (low neutrophil count)—increased susceptibility to infection
(c) Thrombocytopenia (low platelet count)—increased susceptibility to bleeding and ecchymosis (bruising), as well as subcutaneous hemorrhaging resulting in purpura or petechia[5]

Many individuals are asymptomatic, and blood cytopenia or other problems are identified as a part of a routine blood count: neutropenia, anemia and thrombocytopenia (low cell counts of white and red blood cells, and platelets, respectively); splenomegaly or rarely hepatomegaly; abnormal granules in cells, abnormal nuclear shape and size; and/or chromosomal abnormalities, including chromosomal translocations and abnormal chromosome number.

Although there is some risk for developing acute myelogenous leukemia, about 50% of deaths occur as a result of bleeding or infection. Leukemia that occurs as a result of myelodysplasia is notoriously resistant to treatment.

5q-myelodysplasia, (also known as chromosome 5q deletion syndrome, chromosome 5q monosomy, or 5q-syndrome) is a rare disorder caused by loss of part of the long arm (q arm, band 5q31.1) of human chromosome 5. 5q-myelodysplasia is characterized by macrocytic anemia often thrombocytosis, erythroblastopenia, megakaryocyte hyperplasia with nuclear hypolobation and an isolated interstitial deletion of chromosome 5. The 5q-syndrome is found predominantly in females of advanced age.

Some subjects with 5q-myelodysplasia have a decrease in Rps14 expression. Deletion of the miR-145 and miR-146 loci has been associated with elevated platelet count and megakaryocytic dysplasia associated with the 5q-syndrome. 5q-myelodysplasia affects bone marrow cells causing treatment-resistant anemia and myelodysplastic syndromes that may lead to acute myelogenous leukemia. Examination of the bone marrow shows characteristic changes in the megakaryocytes. They are more numerous than usual, small and mononuclear. There may be accompanying erythroid hypoplasia in the bone marrow. Accordingly, in some embodiments, a subject with 5q-myelodysplasia can have dysplastic bone marrow. Subjects with 5q-myelodysplasia can be treated with Lenalidomide (Bennett J et al. (2006). "Lenalidomide in the myelodysplastic syndrome with chromosome 5q deletion". N. Engl. J. Med. 355 (14): 1456-65; Raza et al., (2008). "Phase 2 study of lenalidomide in transfusion-dependent. low-risk, and intermediate-1 risk myelodysplastic syndromes with karyotypes other than deletion 5q". Blood 111 (1): 86-93.)

In some embodiments of all aspects of the present invention, the methods and inhibitors as disclosed herein can be used to treat a subject with a ribosomopathy such as Shwachman-Diamond syndrome, for example, where the subject has a mutation in Sbds. In some embodiments, a subject with Shwachman-Diamond syndrome has one or more symptoms selected from pancreatic insufficiency, bone marrow dysfunction, skeletal deformities.

In another embodiment, an inhibitor as disclosed herein can be used in a method of treating a subject with a ribosomopathy such as Treacher Collins Syndrome, for example, where the subject has a mutation in TCOF1 (nucleolar). Treacher-Collins syndrome is a condition that is passed down through families (hereditary) that leads to problems with the structure of the face. Treacher-Collins syndrome is caused by a defective protein called treacle. The condition is passed down through families (inherited). This condition may vary in severity from generation to generation and from person to person. Symptoms of Treacher-Collins syndrome include at least one of, but are not limited to: abnormal or almost completely missing outer part of the ears, hearing loss, very small jaw (micrognathia), very large mouth, defect in the lower eyelid (coloboma), scalp hair that reaches to the cheeks, cleft palate. Accordingly, a subject with Treacher Collins Syndrome has one or more craniofacial deformities. While a child with Treacher Collins Syndrome usually will show normal intelligence, diagnosis can be made on the bases of an examination of the infant which may reveal a variety of problems, including: (a) Abnormal eye shape, (b) Flat cheekbones, (c) Clefts in the face, (d) Small jaw, (e) Low-set ears, (f) Abnormally formed ears, (g) Abnormal ear canal, (h) Hearing loss, (i) Defects in the eye (coloboma that extends into the lower lid), (j) Decreased eyelashes on the lower eyelid, (k) genetic tests can help identify gene changes linked to this condition. The diagnosis of Treacher Collins Syndrome also relies upon clinical and radiographic findings, and there is a set of typical symptoms within Treacher Collins Syndrome which can be detected by a critical clinical view. The wide spectrum of diseases which have similar characteristics make it sometimes difficult to diagnose TCS. The OMENS classification was developed as a comprehensive and stage-based approach to differentiate the diseases. This acronym describes five distinct dysmorphic manifestations, namely O; orbital asymmetry, M; mandibular hypoplasia, E; auricular deformity, N; nerve development and S; soft-tissue disease.

Selection of Subjects for Administration with a Pharmaceutical Composition Comprising the Inhibitor In some embodiments, a subject amenable or suitable for treatment with a composition comprising an inhibitor as disclosed herein can be selected based on decreased levels of hematopoietic cells and decreased flk1 expression in CD34+ cells, as compared to a control reference normal levels of hematopoetic cells and flk1 expression level from a normal subject. Additionally, a subject amenable or suitable for treatment with a composition comprising an inhibitor as disclosed herein can be selected based on increased levels of p21 expression in CD34+ cells as compared to a control reference p21 expression level. In some embodiments, a subject amenable or suitable for treatment with a composition comprising an inhibitor as disclosed herein can be selected based on decreased CD71+ expression and decreased glycophorin A (GPA) expression in CD34+ cells as compared to a control reference CD71+ and GPA expression level, e.g., in a sample from a normal subject not having a ribosomal disorder or ribosomopathy. In some embodiments, the normal reference levels are the based on the level of hematopoietic cells, flk1 expression, CD71+ expression, GPA expression, p21 expression levels in a sample from a normal subject not having a ribosomal disorder or ribosomopathy, or a control cell line, or cells from a normal tissue sample, where in the tissue sample is a biological tissue sample from a tissue matched, and species matched and age matched biological sample.

In some embodiments, the levels of flk1 expression, CD71+ expression, GPA expression, and p21 expression levels are measured in a biological sample comprising hematopoietic cells or erythroid cells or erythroid differentiated cells. In some embodiments, a biological sample obtained from the subject comprises cancer cells, and can be a biological sample which is serum plasma, blood or tissue sample. In alternative embodiments, the biological sample includes, for example blood, plasma, serum, urine, spinal fluid, plural fluid, nipple aspirates, lymph fluid, external secretions of the skin, respiratory, internal and genitourinary tracts, bile, tears, sweat, saliva, organs, milk cells and primary ascite cells, biopsy tissue sample, an in vitro or ex vivo cultivated biopsy tissue sample.

Pharmaceutical Compositions Comprising the Inhibitor

Another aspect of the present invention relates to pharmaceutical compositions for treatment of diseases or disorders associated with ribosomal proteins or dysfunction or where a subject has a ribosomopathy, e.g., DBA, myelodysplasia, for example, but not limited to 5q-myelodysplasia, Shwachman-Diamond syndrome and Treacher Collins Syndrome. In some embodiments, a pharmaceutical composition of the invention comprises a therapeutically effective amount of at least one of the inhibitors as disclosed herein. In one embodiment, the inhibitor is, for example, but not limited to, inhibitors of rps6; the RSk p90 inhibitors SL, or B1; p70s6K inhibitor PF; Cam inhibitor, TF and FLU; Ca2+

Chelator BABTA; chk2 inhibitors CCT and III, and the inhibitors PerSuc, 221E and ACV; or e.g. the inhibitors of FIG. 33, or the compounds of Formula I or Formula II.

An inhibitor as disclosed herein can be used in an amount of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, an inhibitor can be used in an amount of about 0.1 to 1000 μg/kg of body weight or about 1 to 100 μg/kg of body weight or about 10 to 50 μg/kg of body weight. In some embodiments, the inhibitor as disclosed herein can be used at a concentration of about 0.001 mg/ml or 0.1 mg/ml or a higher concentration of 0.1 mg/ml. In some embodiments, a pharmaceutical composition comprises at least one inhibitor at a concentration of about 0.01 μM to 300 μM, or about 0.1 μM to 150 μM, or about 1 μM to 50 μM, or about 1 μM to 25 μM. The dosage may vary within this range depending upon the dosage form employed and the route of administration utilized.

Depending on routes of administration, one of skill in the art can determine and adjust an effective dosage of an inhibitor disclosed herein to a subject such as a human subject accordingly, by determining pharmacokinetics and bioavailability of an inhibitor and analyzing dose-response relationship specific to an inhibitor in animal models such as a mouse.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$). Compositions that exhibit large therapeutic indices, are preferred.

The data obtained from the cell culture assays and animal studies can be used in formulating a range of dosage for use in humans. The therapeutically effective dose can be determined by one of ordinary skill in the art, e.g. using cell culture assays. A dose can be formulated in animal models to achieve a circulating plasma concentration range that includes the IC50 (i.e., the concentration of the therapeutic which achieves a half-maximal inhibition of symptoms) as determined in cell culture by methods disclosed in the Examples. An effective dose of the inhibitor can be determined in an animal model by measuring the levels of hemoglobin over the course of treatment with the inhibitor as compared to no treatment. In some embodiments, a dosage comprising the inhibitor is considered to be effective if the dosage increases hemoglobin levels, red cell number, and/or reduces expression of p21 in CD34+ cells by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of the inhibitor). In some embodiments, a therapeutically effective amount of the inhibitor administered to a subject is dependent upon factors known to a person of ordinary skill, including bioactivity and bioavailability of the inhibitor (e.g. half-life and stability of the inhibitor in the body), chemical properties of the inhibitor (e.g. molecular weight, hydrophobicity and solubility); route and frequency of administration, time of administration (e.g. before or after a meal), and the like. Further, it will be understood that the specific dose of the pharmaceutical composition comprising the inhibitor as disclosed herein to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising the inhibitor can be determined by methods known to a skilled artisan such as pharmacologists and physicians.

According to the invention, an inhibitor as disclosed herein can be administered prophylactically or therapeutically to a subject prior to, simultaneously or sequentially with other therapeutic regimens or agents (e.g. multiple drug regimens), in a therapeutically effective amount. In some embodiments, the inhibitor is administered concurrently with other therapeutic agents can be administered in the same or different compositions. Additional therapeutic agents or regimens include, but are not limited to, steroids, corticosteroids, blood transfusions and bone marrow transplants.

The active ingredients (e.g. inhibitors of p90S6K; inhibitors of p60S6K; RSk p90 inhibitors SL, or B1, or Sk; p70s6K inhibitor PF; Cam inhibitor, TF or FLU; Ca2+ Chelator BABTA; chk2 inhibitors, CCT or III, and the inhibitors PerSuc, or 221E or ACV; or e.g. the inhibitors of FIG. 33, or the compounds of Formula I and Formula II.) of the pharmaceutical composition according to the invention can be administered to an individual by any route known to persons skilled in the art. The routes of administration include intradermal, transdermal (e.g. in slow release formulations), intramuscular, intraperitoneal, intravenous, subcutaneous, oral, buccal, nasal, rectal, epidural, topical, intrathecal, rectal, intracranial, intratracheal and intrathecal and intranasal routes. Any other therapeutically efficacious route of administration can be used, for example absorption through epithelial or endothelial tissues or systemic administration. In addition, an inhibitor according to the invention can be administered together with other components of biologically active agents such as pharmaceutically acceptable surfactants, excipients, carriers, diluents and vehicles.

For parenteral (e.g. intravenous, subcutaneous, intramuscular) administration, an inhibitor can be formulated as a solution, suspension, emulsion or lyophilized powder in association with a pharmaceutically acceptable parenteral vehicle (e.g. water, saline, dextrose solution) and additives that maintain isotonicity (e g. mannitol) or chemical stability (e.g. preservatives and buffers). The formulation is sterilized by commonly used techniques.

In some embodiments, the route of administration is administration by subcutaneous route. Intramuscular administration is another alternative route of administration. In some embodiments, a pharmaceutical composition comprising an inhibitor can be administered as a formulation adapted for systemic delivery. In some embodiments, the compositions can be administered as a formulation adapted for delivery to specific organs, for example but not limited to the liver. In some embodiments, a pharmaceutical composition comprising an inhibitor as disclosed herein can be administered as a formulation adapted not to pass through the blood-brain barrier.

Alternatively, in some embodiments, a pharmaceutical composition can be incorporated in a gel, sponge, or other permeable matrix (e.g., formed as pellets or a disk) and placed in proximity to the liver endothelium for sustained, local release. The composition comprising an inhibitor can be administered in a single dose or in multiple doses, which are administered at different times.

The exact route of administration as well as the optimal dosages can be determined by standard clinical techniques for each specific case, mainly based on the nature of the disease or disorder and on the stage of this disease. Preferably, the medicament according to the present invention is applied locally or systemically, in particular, orally, intravenously, parenterally, epicutaneously, subcutaneously, intrapulmonarily by inhalation or bronchoalveolar lavage, intramuscularily, intracranially, locally into intervertebral discs or other connective tissues.

As disclosed herein, a pharmaceutical composition comprising an effective amount of at least one inhibitor can be administered to a subject for the therapeutic treatment or prevention (e.g. prophylactic treatment) of ribosomal diseases and disorders or ribosomopathies.

In some embodiments, a composition of the invention comprising an inhibitor as disclosed herein is formulated for ribosomal diseases and/or ribosomophaties, e.g. DBA, myelodysplasia, for example, but not limited to 5q-myelodysplasia, Shwachman-Diamond syndrome and Treacher Collins Syndrome. In one embodiment, an inhibitor as disclosed herein is a derivative, analogue, prodrug, or pharmaceutically acceptable salts thereof.

In some embodiments, a pharmaceutical composition comprising at least one of the inhibitors disclosed herein further comprises a second therapeutic agent. In one embodiment, the second therapeutic agent is a corticosteroid. In some embodiments, the second therapeutic agent is a calcium channel blocker, as disclosed herein.

In prophylactic applications, pharmaceutical compositions (or medicaments) comprising an inhibitor can be administered to a subject susceptible to, or otherwise at risk of, a ribosomal disease or disorder and/or ribosomopathy in an amount sufficient to eliminate or reduce the risk or delay the onset of the disease. In one embodiment, a pharmaceutical composition of the invention disclosed herein comprises a inhibitor of rps6; a RSk p90 inhibitor e.g. SL, or B1; or a p70s6K inhibitor, e.g. PF; or the Cam inhibitor, TF or FLU; or the Ca2+ Chelator BABTA; or the chk2 inhibitor, CCT or III; or one of the inhibitors PerSuc, 221E, or ACV, DB-4-088-2 (088-2); DB-4-088-3 (088-3); DB-4-086 (086); DB-4-087-2 (087-2); DB-4-087-3 (087-3); DB-4-089 (089), or a compound of Formula I or Formula II; or rps6 inhibitor; or enantiomers, prodrugs, derivatives or pharmaceutically acceptable salts thereof.

In therapeutic applications, according to the invention provided herein, when an effective amount or effective dose of a pharmaceutical composition comprising an inhibitor as disclosed herein can be administered to the subject with a ribosomal disease or disorder and/or ribosomopathy so that at least one of the symptoms of such a ribosomal disease can be delayed or inhibited. In some embodiments, administration of an effective amount or effective dose of a pharmaceutical composition comprising an inhibitor to a subject with a ribosomal disease or disorder and/or ribosomopathy can inhibit or delay progression of facial abnormalities, and/or other symptoms associated with the ribosomal disease or ribosomopathy. In further embodiments, treating subjects with an effective dose of a pharmaceutical composition comprising an inhibitor can prevent or delay a symptom of the ribosomal disease or ribosomopathy in the subject.

In some embodiments, the present invention also provides compositions comprising an inhibitor as discussed herein for practicing the therapeutic and prophylactic methods described herein. In some embodiments, combinations of an inhibitor and another therapeutic agent can be tailored to be combined in a pharmaceutical composition, where each therapeutic can target a different symptom, a different disease or a different disorder. In further embodiments, the inhibitor and another therapeutic can be mixed together in a pharmaceutical composition as disclosed herein. In other embodiments, an inhibitor and another therapeutic can be present in a different formulation when combined in a pharmaceutical composition. For example, in one embodiment, the inhibitor can be present in a liquid formulation, while another therapeutic can be lyophilized into powder. The formulations of different active ingredients in a pharmaceutical composition as disclosed herein (e.g. inhibitors of rps6; Inhibitors of p90S6K or p70S6K; RSk p90 inhibitors SL, B1; p70s6K inhibitor PF; Cam inhibitor, TF and FLU; Ca2+ Chelator BABTA; chk2 inhibitors CCT and III, and the inhibitors PerSuc, 221E and ACV; or the inhibitor compounds of FIG. 33, or the compounds of Formula I or II.) can be optimized accordingly by various factors such as physical and chemical properties of a drug, bioavailability, route of administration, and whether it is a sustained or a burst release for the drug. Therapeutic and prophylactic compositions of the present invention can further comprise a physiologically tolerable carrier together with an inhibitor as disclosed herein (inhibitors of rps6; inhibitors of p90S6K or p70S6K; RSk p90 inhibitors SL, B1; p70s6K inhibitor PF; Cam inhibitor, TF and FLU; Ca2+ Chelator BABTA; chk2 inhibitors CCT and III, and the inhibitors PerSuc, 221E and ACV, or the compounds of Formula I or Formula II), or derivatives, enantiomers, prodrugs or pharmaceutically acceptable salts thereof. In additional embodiments, an inhibitor and another therapeutic can employ different physiologically tolerable carriers when combined in a pharmaceutical composition of the invention as disclosed herein.

In some embodiments, a pharmaceutical composition as disclosed herein comprises an inhibitor together with other therapeutics and a pharmaceutically acceptable excipient. Suitable carriers for an inhibitor of the invention, and their formulations, are described in Remington's Pharmaceutical Sciences, 16th ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. Further carriers include sustained release preparations such as semipermeable matrices of solid hydrophobic polymers, which matrices are in the form of shaped articles, e.g. liposomes, films or microparticles. It will be apparent to those of skill in the art that certain carriers can be more preferable depending upon for instance the route of administration and concentration of the inhibitor being administered.

In some embodiments, bioavailability of the inhibitor according to the invention can also be improved by using conjugation procedures which increase the half-life of the inhibitor in a subject, for example linking the inhibitor to polyethylene glycol, as described in WO 92/13095, which is incorporated herein in its entirety by reference.

In some embodiments, bioavailability of the inhibitor according to the invention can be also enhanced by encapsulating a the inhibitor in biocompatible delivery vehicles which increase the half-life of an inhibitor in a human body. Exemplary biocompatible delivery vehicles include polymeric vehicles such as PEG-based vehicles, or liposome-based vehicles.

In some embodiments, the inhibitor can be dissolved or dispersed as an active ingredient in the physiologically tolerable carrier to increase the half-life of the inhibitor in a subject.

The preparation of a pharmacological composition that contains active ingredients (e.g inhibitors of rps6; inhibitors of p90S6K or p70S6K; RSk p90 inhibitors SL, or B1; p70s6K inhibitor PF; Cam inhibitor, TF and FLU; Ca2+ Chelator BABTA; chk2 inhibitors CCT and III, and the inhibitors PerSuc, 221E and ACV; or e.g. the inhibitors of FIG. 33; or the compounds of Formulas I or II) dissolved or dispersed therein is well understood in the art and need not be limited based on formulation. Typically such compositions are prepared as injectable either as liquid solutions or suspensions, however, solid forms suitable for solution or suspension in liquid prior to use can also be prepared. The preparation can also be emulsified or presented as a liposome composition. In some embodiments, the inhibitor can be mixed with excipients which are pharmaceutically acceptable and compatible with the active ingredient and in amounts suitable for use in the therapeutic methods described herein. In addition, if desired, the composition comprising the inhibitor can contain minor amounts of auxiliary substances such as wetting or emulsifying agents, pH buffering agents and the like which enhance the effectiveness of the active ingredient.

Physiologically tolerable carriers (i.e. physiologically acceptable carriers) are well known in the art. Selection of pharmaceutically acceptable carriers can be accomplished by means of administration by a skilled artisan. For example, if the composition is orally administered, it can be formulated in coated tablets, liquids, caplets and so forth. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. For topical application, the carrier may be in the form of, for example, and not by way of limitation, an ointment, cream, gel, paste, foam, aerosol, suppository, pad or gelled stick. In some embodiments, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). An inhibitor as disclosed herein can be administered in the form of a depot injection or implant preparation which can be formulated in such a manner as to permit a sustained or pulsatile release of the active ingredient.

As used herein, the 'inhibitors as disclosed herein' include e.g. inhibitors of rps6; inhibitors of p90S6K or p70S6K; RSk p90 inhibitors SL, or B1; p70s6K inhibitor PF; Cam inhibitor, TF and fluphenazine (FLU); the Ca2+ Chelator BABTA; chk2 inhibitors CCT and III, and the inhibitors PerSuc, 221E and ACV; and DB-4-083, DB-4-084, DB-4-088-2, DB-4-088-3, DB-4-086, DB-4-087-2, DB-4-087-3, DB-4-089. The compounds of Formula I and Formula II, and derivatives and analogs thereof (See e.g. FIG. 5, FIG. 31, FIG. 32, and FIG. 33, for structures).

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

A skilled artisan will be able to determine the appropriate way of administering pharmaceutical compositions comprising at least one LSF inhibitor as disclosed herein in view of the general knowledge and skill in the art.

Treatment Regimes

Another aspect of the present invention relates to methods for therapeutic and prophylactic treatment of diseases or disorders, where inhibition of p53 activation is desirable for the treatment or prevention of a ribosomal disorder or a ribosomopathy. The methods comprise administering to a subject in need thereof a pharmaceutical composition comprising a therapeutically effective amount of at least one inhibitor selected from for example, any, or a combination, of compounds such as small molecule or protein inhibitors of rps6, p90S6K or p70S6K; the p90S6K inhibitors SL and B1; the p70s6K inhibitor PF; the Cam inhibitor, TF and FLU; the Ca2+ chelator BABTA; the chk2 inhibitors CCT and III, and the inhibitors PerSuc, 221E and ACV; and those of FIG. 33, and of Formula I and Formula II), and analogues and variants as disclosed herein.

In one embodiment, Diamond-Blackfan anemia (DBA) is treated or prevented by the methods and compositions of the present invention with an inhibitor as disclosed herein.

Effective doses of the pharmaceutical composition comprising an inhibitor as disclosed herein. for the treatment of ribosome protein diseases or disorders or associated with a ribosomopathy depend upon many different factors, including means of administration, physiological state of the subject, whether the subject is human or an animal, other medications administered, and whether treatment is prophylactic or therapeutic. Depending on the clinical condition of a subject, dosage and frequency of pharmaceutical compositions of the present invention can be adjusted accordingly over time by one of the skill in the art, e.g. physicians.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with DBA can be treated with an inhibitor as disclosed herein at an effective dose in a therapeutic regimen accordingly to decrease the p21 levels and or p53 levels back to a normal level, and then be administered a maintenance dose, e.g., prophylactically. In some embodiments, an inhibitor as disclosed herein can be administered to subjects prior to, concurrently with, or sequentially to treatment with a corticosteroid, and/or when the subject us undergoing an adjuvant therapy, such as a blood transfusion and/or bone marrow transplant. In some embodiments for example, a DBA subject which is selected for other therapeutic procedures or surgeries, such as blood transfusions and/or bone marrow transplant, can be subjected to a treatment with an inhibitor as disclosed herein.

For example, a pharmaceutical composition of the invention can be administered prior to, during or after therapeutic procedures. Route of administration can vary with therapeutic procedures or surgeries and can be determined by a skilled artisan. In yet another embodiment, compositions and methods of the invention can be used as an adjuvant therapy.

In some embodiments, the subject is a human, and in alternative embodiments the subject is a non-human mammal. Treatment dosages need to be titrated to optimize safety and efficacy. The amount of an inhibitor depends on the stage of the disease, as well as the species.

In some embodiments, an inhibitor can be administered to a subject in a pharmaceutical composition comprising an amount of an inhibitor of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, an inhibitor can be used in an amount of about 0.1 to 1000 μg/kg of body weight or about 1 to 100 μg/kg of body weight or about 10 to 50 μg/kg of body weight. In some embodiments, an inhibitor can be administered at a concentration of about 0.001 mg/ml or 0.1 mg/ml or a higher concentration of 0.1 mg/ml. In alternative embodiments, a pharmaceutical composition comprises at least one inhibitor at a concentration of about 0.01 μM to 300 μM, or about 0.1 μM to 150 μM, or about 1 μM to 50 μM, or about 1 μM to 25 μM.

In some embodiments, an inhibitor as disclosed herein can be administered to a subject according to the methods in an effective dose to increase the levels of CD71+ cells in an erythroid cell population obtained from the subject by at least about 1%, at least about 2%, at least about 3%, at least about 5%, at least about 10%, at least about 15%, least about 20%, at least about 30%, at least about 40%, at least about 50%, or more than 50%, as compared to in the absence of the inhibitor.

In another embodiment, an inhibitor as disclosed herein can be administered to a subject according to the methods as disclosed herein in an effective dose to decrease the levels of p21 expression in CD34+ cells present in an erythroid cell population obtained from the subject by at least about 1%, at least about 2%, at least about 3%, at least about 5%, at least about 10%, at least about 15%, least about 20%, at least about 30%, at least about 40%, at least about 50%, at least about 60%, at least about 70%, at least about 80%, at least about 90%, at least about 95%, at least about 98%, at least about 99%, or more than 99%, as compared to in the absence of the inhibitor.

Generally, effective dosages and dosing schedules can be adjusted based on, for example, the outcome of the treatment such as whether the subject has reduced symptoms of anemia, and/or whether at least one of the symptoms associated with the ribosomal protein disorder, such as DBA is reduced. In accordance with the teachings provided herein, the effectiveness of the treatment can be monitored by obtaining a biological sample from a subject, e.g. a blood serum sample, and determining the level of biomarkers for DBA, such as percentage of CD71+ cells in a erythroid cell population and/or level of p21 in CD34+ cells, using methods well known in the art and the diagnostic methods as disclosed later herein.

In some embodiments, the daily dose administered to a subject in a form of a bolus composition comprising an inhibitor can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

The pharmaceutical compositions comprising at least one inhibitor as disclosed herein can be administered by parenteral, topical, intravenous, oral, subcutaneous, intraperitoneal, intranasal or intramuscular means for prophylactic and/or therapeutic treatment. For example, for treatment of cancer, e.g., HCC, a pharmaceutical composition comprising at least one LSF inhibitor can be injected systemically such as by intravenous injection, or by injection or application to the relevant site, such as by direct injection into a tumor, or direct application to the site when the site is exposed in surgery. Other routes of administration of an inhibitor as disclosed herein are intramuscular (i.m.), intravenous (i.v.), subcutaneous (s.c.), or orally, although other routes can be equally effective. Intramuscular injection is most typically performed in the arm or leg muscles. In some methods, an inhibitor as disclosed herein can be administered as a sustained release composition or device, such as a Medipad™ device.

In some embodiments, an inhibitor as disclosed herein can optionally be administered in combination with other agents that are at least partly effective in treatment of ribosomal protein diseases and disorders, such as blood transfusions, bone marrow transplants and the like. In other embodiments, an inhibitor of the invention can be administered prior to, concurrently, or after administration of another therapeutics that targets another disease or disorder, or a different symptom.

In various embodiments, an inhibitor can be a pro-drug, where it is activated by a second agent. Accordingly, in such embodiments, administration of such the second agent which activates the pro-drug of the inhibitor into its active form can be administered the same time, concurrent with, or prior to, or after the administration of the pharmaceutical composition comprising an inhibitor as disclosed herein.

In some embodiments, an inhibitor as disclosed herein is often administered as pharmaceutical compositions comprising an active therapeutic agent, e.g. inhibitors of rps6; inhibitors of p90S6K or p70S6K; RSk p90 inhibitors SL and B1; p70s6K inhibitor PF; Cam inhibitor, TF and FLU; Ca2+ Chelator BABTA; chk2 inhibitors CCT and III, and the inhibitors PerSuc, 221E and ACV; and those of FIG. 33, and of Formulas I and II), and a variety of other pharmaceutically acceptable components. See Remington's Pharmaceutical Science (15th ed., Mack Publishing Company, Easton, Pa., 1980). The formulation of the compositions depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, non-therapeutic, non-immunogenic stabilizers and the like. However, some reagents suitable for administration to animals may not necessarily be used in compositions for human use.

For parenteral administration, an inhibitor as disclosed herein can be administered as injectable dosages of a solution or suspension of the substance in a physiologically acceptable diluent with a pharmaceutical carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Topical application can result in transdermal or intradermal delivery. Topical administration can be facilitated by co-administration of the agent with cholera toxin or detoxified derivatives or subunits thereof or other similar bacterial toxins (Sec Glenn et al., Nature 391, 851 (1998)). Co-administration can be achieved by using the components as a mixture or as linked molecules obtained by chemical crosslinking or expression as a fusion protein.

Other mode of administration includes systemic delivery. In some embodiments, at least one inhibitor as disclosed herein can be injected systemically such as by intravenous injection, or by injection or application to the relevant site, such as direct application to the site when the site is exposed in surgery. In some embodiments, a pharmaceutical composition of the invention can be formulated in a tablet and used orally for systemic administration. In various embodiments, pharmaceutical compositions of the invention can further comprises non-active ingredients (i.e. ingredients that have no therapeutic values for treatment of diseases, disorders or symptoms), such as physiologically acceptable carriers.

In various embodiments, modification of an inhibitor by addition of a polymer is specifically contemplated, for example, using a covalent attachment to a polymer. In other embodiments, an inhibitor can be mixed with or encapsulated in a biocompatible polymer.

In another aspect, biodegradable or absorbable polymers can provide extended, often localized, release of an inhibitor as disclosed herein. The potential benefits of an increased half-life or extended release for a therapeutic agent are clear. A potential benefit of localized release is the ability to achieve much higher localized dosages or concentrations, for greater lengths of time, relative to broader systemic administration, with the potential to avoid possible undesirable side effects that may occur with systemic administration.

Bioabsorbable polymeric matrix suitable for delivery of an inhibitor as disclosed herein, or variants or fragments or derivatives thereof can be selected from a variety of synthetic bioabsorbable polymers, which are described extensively in the literature. Such synthetic bioabsorbable, biocompatible polymers, which may release proteins over several weeks or months can include, for example, polyhydroxy acids (e.g. polylactides, polyglycolides and their copolymers), polyanhydrides, polyorthoesters, segmented block copolymers of polyethylene glycol and polybutylene terephtalate (POLYACTIVE™), tyrosine derivative polymers or poly (ester-amides). Suitable bioabsorbable polymers to be used in manufacturing of drug delivery materials and implants are discussed e.g. in U.S. Pat. Nos. 4,968,317, 5,618,563 (which are incorporated herein in their entirety by reference), among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

The methods of the present invention also are useful for monitoring a course of treatment being administered to a subject. The methods can be used to monitor both therapeutic treatment on symptomatic subject and prophylactic treatment on asymptomatic subject.

A treatment administered to a subject is considered to be effective if the level of expression of p21 in CD34+ cells present in a biological sample obtained from the subject is decreased by at least about 20%, at least about 30%, at least about 40%, at least about 50%, at least about 60%, at least about 70%, at least about 80%, at least about 90%, at least about 95%, at least about 98%, about 99% or about 100% as compared to a reference level, or in the absence of the inhibitor. In such embodiments, the reference level is the measurement of p21 in CD34+ cells present in a biological sample obtained from the subject at a previous time point, e.g., who has not been administered the inhibitors. Based on the outcome of treatment, the dosage and frequency of administration using the methods and compositions as disclosed herein can be adjusted accordingly by one of skill in the art.

One can use any immunoassay to determine the level of p21 expression in CD34+ cells in a biological sample, such as ELISA or immunohistochemical methods which are commonly known in the art and are encompassed for use in the present invention.

Kits

Another aspect of the present invention relates to a kit comprising one or more inhibitors as disclosed herein (e.g. inhibitors of rps6; inhibitors of p90S6K or p70S6K; RSk p90 inhibitors SL, or B1; p70s6K inhibitor PF; Cam inhibitor, TF and FLU; Ca2+Chelator BABTA; chk2 inhibitors CCT and III, and the inhibitors PerSuc, 221E and ACV; and the compounds of FIG. 33, and of Formulas I and II), and instructions for carrying out a method as disclosed herein.

In some embodiments, a kit can optionally additionally comprise reagents or agents for measuring the level of p21 expression in a biological sample from the subject, such as, for example, a blood sample, for example to identify the efficacy of treatment with the inhibitor as disclosed herein. Such agents are well known in the art, and include without limitation, labeled antibodies that specifically bind to p21 protein and/or mRNA and the like. In some embodiments, the labeled antibodies are fluorescently labeled, or labeled with magnetic beads and the like. In some embodiments, a kit as disclosed herein can further comprise at least one or more reagents for profiling and annotating a biological sample from the subject in high throughput assay.

In some embodiments, the kit can further comprise instructions for administering a composition comprising an inhibitor to a subject in need thereof, e.g., with a ribosomal protein disease or disorder, e.g., DBA and instructions for doses and the like.

In addition to the above mentioned component(s), the kit can also include informational material. The informational material can be descriptive, instructional, marketing or other material that relates to the methods described herein and/or the use of the components for the assays, methods and systems described herein.

In some embodiments, the methods and kits comprising an inhibitor as disclosed herein can be performed by a service provider, for example, where an investigator or physician can send the biological sample to a diagnostic laboratory service provider to measure the level of p21 expression in CD34+ cells, and/or the level of CD71+ cells in a erythroid cell population present in the biological subject from the subject. In such an embodiment, after performing the such measurements, the service provider can provide the investigator or physician a report of the efficacy of the inhibitor and/or report if the subject is a suitable or amenable to be treated with an inhibitor according to the methods and composition as disclosed herein.

In alternative embodiments, a service provider can provide the investigator with the raw data of the levels of p21 p53 expression in CD34+ cells, and/or the levels of CD71+ cells in a erythroid cell population present in the biological subject from the subject and leave the analysis to be performed by the investigator or physician. In some embodiments, the report is communicated or sent to the investigator via electronic means, e.g., uploaded on a secure web-site, or sent via e-mail or other electronic communication means. In some embodiments, the investigator can send the samples to the service provider via any means, e.g., via mail, express mail, etc., or alternatively, the service provider can provide a service to collect the samples from the investigator and transport them to the diagnostic laboratories of the service provider. In some embodiments, the investigator can deposit the samples to be analyzed at the location of the service provider diagnostic laboratories. In alternative embodiments, the service provider provides a stop-by service, where the service provider send personnel to the laboratories of the investigator and also provides the kits, apparatus, and reagents for performing the assays to measure the levels of p21 expression in CD34+ cells, and/or the level of CD71+ cells in a erythroid cell population present in the biological subject from the subject as disclosed herein in the investigators laboratories, and analyses the result and provides a report to the investigator for each subject, and leaves the physician to make appropriate recommendations of treatment, and dose to administer the subject with a composition comprising an inhibitor according to the methods as disclosed herein.

The following numbered paragraphs represent embodiments of the invention:

Paragraph 1 A method of treating a subject with a ribosomal disorder or ribosomopathy, comprising administering an effective amount of an inhibitor of ribosomal s6 kinase, RSK (p90S6k), to the subject to decrease p90S6K activity and decrease active p53 in at least one of CD34+ cells, erythroid cells or erythroid differentiated cells in the subject.

Paragraph 2, the method of paragraph 1, wherein the inhibitor of p90S6k inhibits a variant selected from the group consisting of RSK1, RSK2 and RSK3.

Paragraph 3, the method of paragraph 1, wherein the inhibitor of p90S6k selectively inhibits RSK2.

Paragraph 4, the method of paragraph 1, wherein the inhibitor of p90S6k is a nucleic acid, a small molecule compound, or a protein.

Paragraph 5, the method of paragraph 1, wherein the inhibitor of p90S6k is SL0101 (SL), or a derivative or analogue of SL0101 (SL), wherein SL0101 (SL) has the following structure:

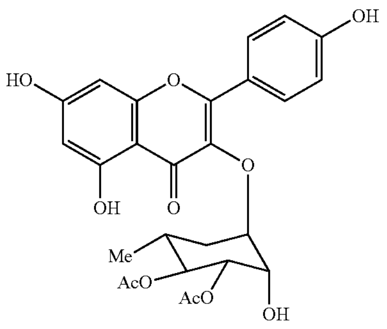 [SMILES: CC(=O)OC1C(C)CC(Oc2c(-c3ccc(O)cc3)oc3cc(O)cc(O)c3c2=O)C(O)C1OC(C)=O]

Paragraph 6, the method of paragraph 1, wherein the inhibitor of p90S6k is BI-D1870 (BI) or a derivative or analogue of BI-D1870 (BI), wherein BI-D1870 (BI) has the following structure:

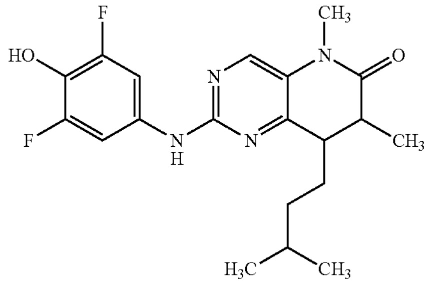

Paragraph 7, a method of treating a subject with a ribosomal disorder or ribosomopathy, comprising administering an effective amount of an inhibitor of –RSK (p70S6K) to the subject to decrease p70S6K activity and decrease active p53 in at least one of CD34+ cells, erythroid cells or erythroid differentiated cells in the subject.

Paragraph 8, the method of paragraph 7, wherein the inhibitor of p70S6k is a nucleic acid, small molecule compound, or a protein.

Paragraph 9, the method of paragraph 7, wherein the inhibitor of p70S6k is PF-4708671 (PF), or a derivative or analogue of PF-4708671 (PF), wherein PF-4708671 (PF) has the following structure:

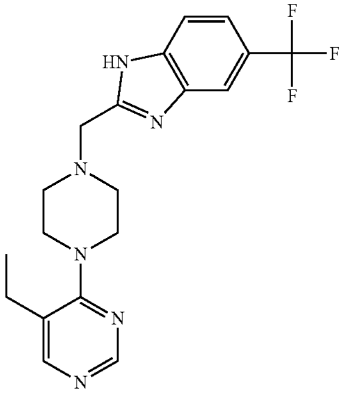 [SMILES: CCc1cncnc1N1CCN(Cc2nc3cc(C(F)(F)F)ccc3[nH]2)CC1]

Paragraph 10, a method of treating a subject with a ribosomal disorder or ribosomopathy, comprising administering an effective amount of an inhibitor of Chk2 to the subject to decrease active p53 in at least one of CD34+ cells, erythroid cells or erythroid differentiated cells in the subject, wherein the inhibitor of Chk2 comprises a compound selected from the group consisting of CCT and III, or derivatives thereof, wherein CCT and III have the following structures:

CCT

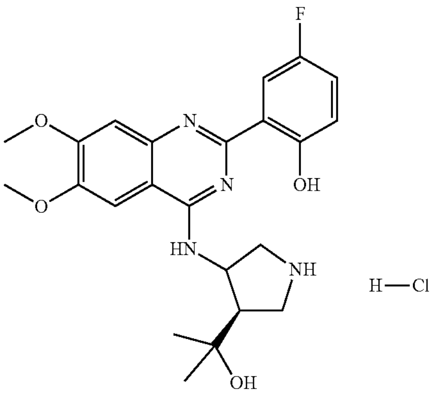

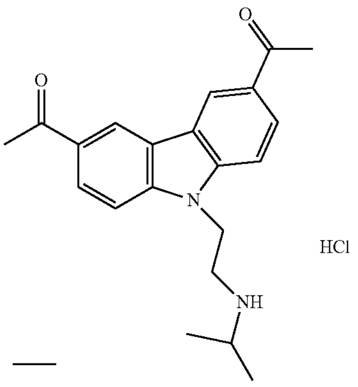

-continued

III

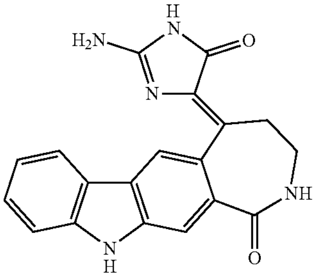

Paragraph 11, a method of treating a subject with a ribosomal disorder or ribosomopathy, comprising administering an effective amount of an inhibitor of calmodulin to the subject to decrease active p53 in at least one of CD34+ cells, erythroid cells or erythroid differentiated cells in the subject, wherein the inhibitor of calmodulin is a phenothiazine compound, or a derivative or analogue of the phenothiazine compound, wherein the phenothiazine compound is selected from the group consisting of ACV-1-235 (ACV); JJM-II-221E (221E); and DB1026 (PerSucc) having the following structures:

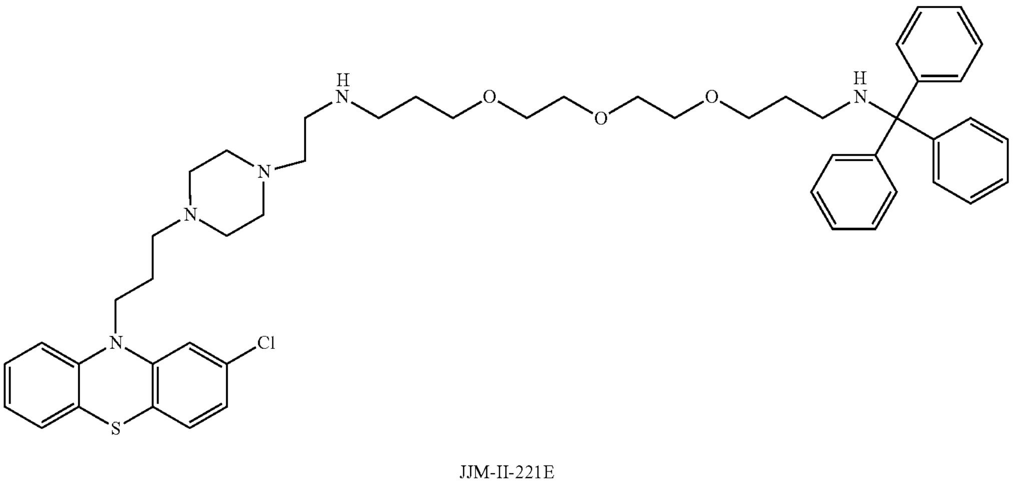

JJM-II-221E

-continued

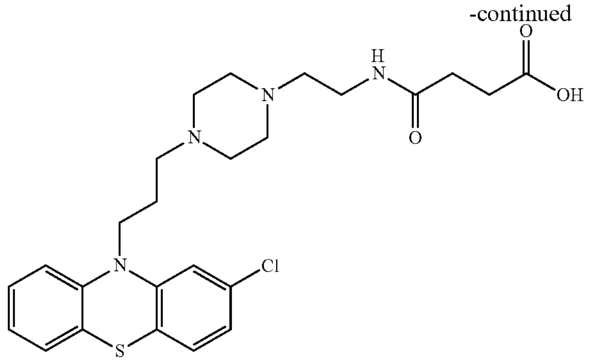

Paragraph 12, a method of treating a subject with a ribosomal disorder or ribosomopathy, comprising administering an effective amount a phenothiazine compound, or a derivative or analogue of the phenothiazine compound, and wherein the phenothiazine compound is selected from the group consisting of DB-4-083 (083); DB-4-084 (084); DB-4-088-2 (088-2); DB-4-088-3 (088-3); DB-4-086 (086); DB-4-087-2 (087-2); DB-4-087-3 (087-3); DB-4-089 (089) having the following structures:

DB-4-083

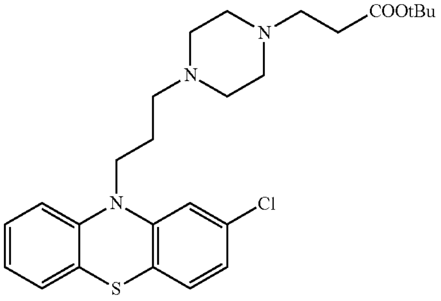

DB-4-084

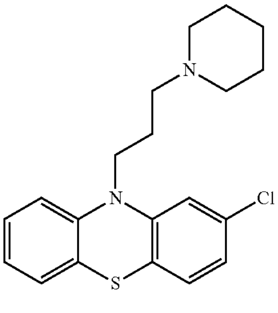

DB-4-086

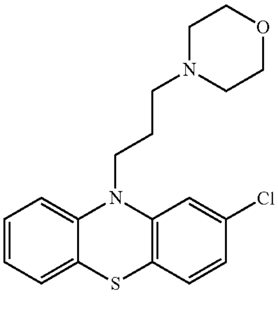

-continued

DB-4-087-2

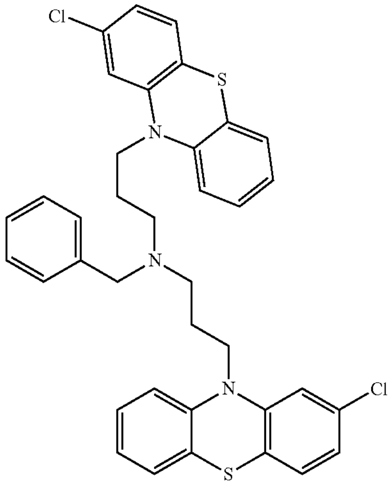

DB-4-088-2

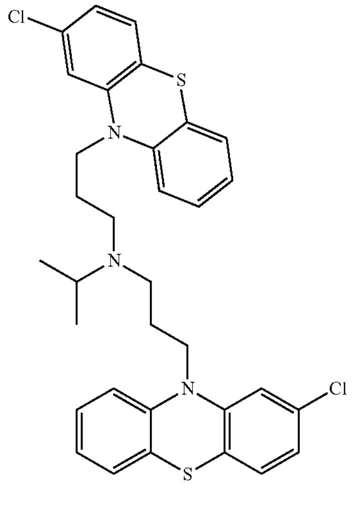

-continued

DB-4-089

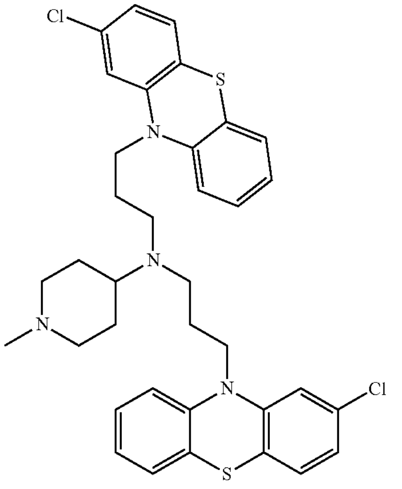

DB-4-088-3

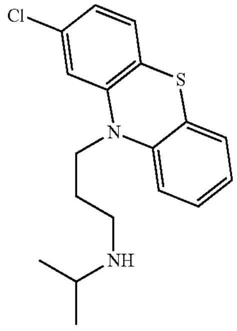

DB-4-087-3

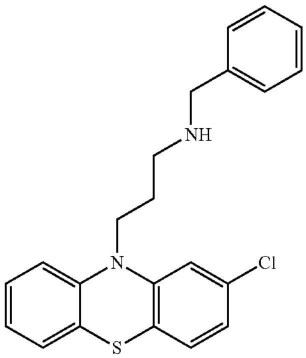

Paragraph 13, a method of treating a subject with a ribosomal disorder or ribosomopathy, comprising administering an effective amount of a composition comprising a phenothiazine compound, or a derivative or analogue of the phenothiazine compound, wherein the phenothiazine compound is a compound of Formula (I):

FORMULA (I)

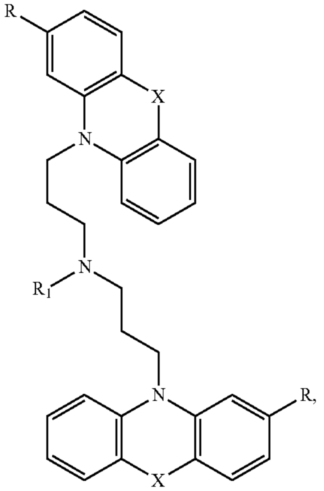

wherein:

X is O or S;

$R^1$ is H, alkyl, alkenyl, alkynyl, cyclyl, heterocyclyls, acyl, aryl, heteroaryl, alkylheteroaryl or alkylaryl;

each R is independently H, halo, alkyl, alkyl, alkenyl, alkynyl, haloalkyl, CN, OH, $NH_2$, alkylamino, dialkylamino, $CO_2H$, acyl, SH, thioalkoxy, $SO_2H$, or $SO_3H$; and isomers and pharmaceutically acceptable salts thereof.

Paragraph 14, a method of treating a subject with a ribosomal disorder or ribosomopathy, comprising administering an effective amount of a composition comprising a a phenothiazine compound, or a derivative or analogue of the phenothiazine compound, wherein the phenothiazine compound is a compound of Formula (II):

FORMULA (II)

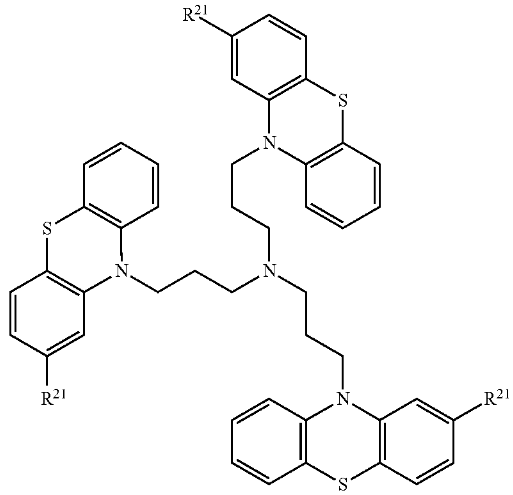

wherein:

each $R^{21}$ is independently selected from the group consisting of H, halo, alkyl, haloalkyl, CN, OH, $NH_2$, alkylamino, dialkylamino, $CO_2H$, acyl, SH, thioalkoxy, $SO_2H$, and $SO_3H$;

isomers and pharmaceutically acceptable salts thereof.

Paragraph 15, method of treating a subject with a ribosomal disorder or ribosomopathy, comprising administering an effective amount a composition comprising a phenothiazine compound, or a derivative or analogue of the phenothiazine compound, wherein the phenothiazine compound is a compound of structure:

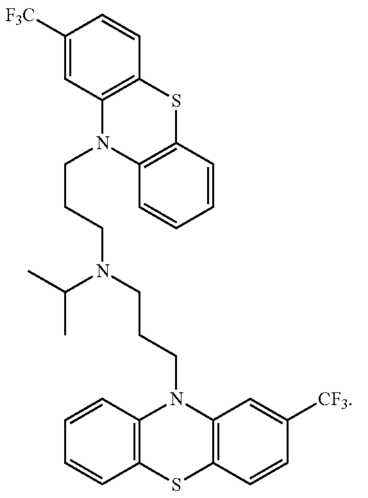 [SMILES: CC(C)N(CCCN1c2ccccc2Sc2ccc(C(F)(F)F)cc21)CCCN1c2ccccc2Sc2ccc(C(F)(F)F)cc21]

Paragraph 16, a method of treating a subject with a ribosomal disorder or ribosomopathy, comprising administering an effective amount of the is a calcium channel blocker BAPTA-AM or derivative or analogue thereof to the subject to decrease active p53 in at least one of CD34+ cells wherein BAPTA-AM has the following structure:

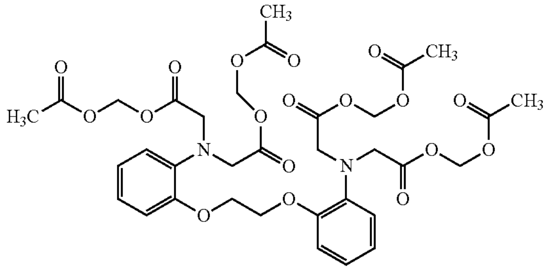 [SMILES: CC(=O)OCOC(=O)CN(CC(=O)OCOC(C)=O)c1ccccc1OCCOc1ccccc1N(CC(=O)OCOC(C)=O)CC(=O)OCOC(C)=O]

Paragraph 17, the method of any of paragraphs 1-16, wherein the subject with a ribosomal disorder has Diamond Blackfan Anemia (DBA) or inherited erythroblastopenia.

Paragraph 18, the method of paragraph 17, wherein the subject has DBA1, DBA2, DBA3, DBA4, DBA5, DBA6, DBA7, or DBA8.

Paragraph 19, the method of any of paragraphs 1-16, wherein the subject has a mutation in ribosomal protein 19 (RPS19).

Paragraph 20, the method of any of paragraphs 1-16, wherein the subject has a mutation in ribosomal protein selected from RPS7, RPS10, RPS19, RPS24, PRS26, RPS17, PRS27L RPS29, RPL35A, PRL5 and PPL11.

Paragraph 21, the method of any of paragraphs 1-16, wherein the subject has a mutation in a ribosomal protein selected from the group consisting of: rPL2A, rPL2B, rPL3, rpL4A, rPL4B, rPL7A, rPL7B, rPL10, rPL11, rPL16A, rPL17A, rPL17B, rPL18A, rPL18B, Rpl19A, rPL19, rPL25, rPL29, rpL31A, rpL31B, rPL36A, rPL40A, rPS1A, rPS6A, rPS6B, rPS14A, rPS15, rPS19, rPS23B, rPS25A, rPS26B, rPS29, rPS29B and rPS31.

Paragraph 22, the method of any of paragraphs 1-16, wherein the subject is administered another therapeutic agent to treat the ribosomal protein defect, selected from the group consisting of: corticosteroids, blood transfusions.

Paragraph 23, the method of any of paragraphs 1-16, wherein the effective amount increases the number of CD71+ erythroid cells in the subject.

Paragraph 24, the method of any of paragraphs 1-16, wherein the effective amount increases hemoglobin levels in the subject.

Paragraph 25, the method of any of paragraphs 1-16, wherein the subject has a symptom of macrocytic anemia or craniofacial abnormalities.

Paragraph 26, the method of any of paragraphs 1-16, wherein the ribosomopathy is myelodysplasia.

Paragraph 27, the method of any of paragraphs 1-16, wherein the myelodysplasia is 5q-myelodysplasia.

Paragraph 28, the method of any of paragraphs 1-16, wherein the subject has a mutation in Rps14 or decrease in Rps14 expression.

Paragraph 29, the method of any of paragraphs 1-16, wherein subject has a symptom of dysplastic bone marrow.

Paragraph 30, the method of any of paragraphs 1-16, wherein the ribosomopathy is Shwachman-Diamond syndrome.

Paragraph 31, the method of any of paragraphs 1-16, wherein the subject has a mutation in Sbds.

Paragraph 32, the method of any of paragraphs 1-16, wherein subject has a symptom selected from: pancreatic insufficiency, bone marrow dysfunction, skeletal deformities.

Paragraph 33, the method of any of paragraphs 1-16, wherein the ribosomopathy is Treacher Collins Syndrome.

Paragraph 34, the method of any of paragraphs 1-16, wherein the subject has a mutation in TCOF1 (nucleolar).

Paragraph 35, the method of any of paragraphs 1-16, wherein the subject has a symptom of craniofacial deformities.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents. All references, patents and publications cited herein are incorporated by reference in their entirety.

EXAMPLES

Although any known methods, devices, and materials may be used in the practice or testing of the invention, the methods, devices, and materials in this regard are described herein.

The examples presented herein relate to methods and compositions comprising at least one inhibitor as disclosed herein for treatment of a ribosomal disorder or ribosomapathy, for example, but not limited to DBA. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Materials and Methods

Embryo Manipulation and Chemical Treatment

Fish were maintained under approved laboratory conditions. Studies were performed on AB wildtype strains and hi2903, an insertional mutant in the first intron of ribosomal protein S29 (rps29). Embryos were subjected to chemicals diluted in E3. For screening, chemicals from ICCB Biomol Known Bioactive, Sigma, and Lopac libraries were tested at 1:300 dilutions from library stock. Compounds were tested in two independent experiments of 20 embryos each, so approximately 10 mutant embryos were scored per chemical. Compounds were diluted in DMSO or water and tested in doses from 5-50 μg/mL

In Situ Hybridization and Benzidine Staining

Whole-mount in situ hybridization (ISH) was performed as described (Thisse and Thisse, 2008). Antisense probes were synthesized from digested plasmid. O-Dianisidine was performed as described previously (Paffett-Lugassy and Zon, 2005).

Cell Culture and Infection

A549 and $CD34^+$ cells were infected with previously characterized lentiviral shRNA targeting RPS19 (Dutt et al., 2011). Unless otherwise noted, drugs were added one day post infection, and cells were collected for analysis 3-6 days post infection.

Flow Cytometry and Immunofluorescence

For flow cytometry based measurement of protein levels, cells were fixed in 2% paraformaldehyde for 15 minutes at 37° C., and methanol was added for overnight incubation at 4° C. Cells were incubated for one hour in 1:100 diluted p21 primary antibody (Cell Signaling 12D1) followed by one hour in conjugated secondary antibody and 1:50 diluted p53-conjugated antibody (Cell Signaling 1C12). Immunofluorescence staining was performed as previously described (Dutt et al., 2011).

Example 1

Ribosomal protein mutations are common in patients with Diamond Blackfan anemia (DBA), who have red cell aplasia and craniofacial abnormalities. The inventors have previously characterized a zebrafish mutant in rps29, a ribosomal protein in the small subunit. $Rps29^{-/-}$ embryos have morphological defects in the head, as well as decreased hematopoietic stem cells, hemoglobin, and staining of endothelial markers. Consistent with other models of DBA, knockdown of p53 near completely rescues the rps29 mutant phenotype. To identify chemicals that could rescue the rps29 mutant phenotype, the inventors performed an in vivo chemical screen. Inhibitors were found to rescue morphological, endothelial, and hemoglobin phenotypes.

Zebrafish RPS29 Mutants have p53-dependent Hematopoietic Phenotypes

The zebrafish work has focused on the rps29 mutant (Amsterdam et al., 2004). The inventors have previously reported that $Rps29^{-/-}$ mutant embryos initially have hematopoietic and endothelial defects (Burns et al., 2009). Rps29 embryos have a defect in arterial specification, leading to decreased hematopoietic stem cells and decreased flk1 expression in the intersegmental vessels at 24 hours post fertilization (hpf). Primitive erythropoiesis is specifically affected, as $rps29^{-/-}$ embryos have less hemoglobin whereas primitive myelopoiesis is unaffected. The rps29 mutant embryos have increased apoptosis, as seen by changes in head morphology and TUNEL staining. Microarray analysis demonstrated an activation of p53 and its targets in the mutant embryo. When a p53 mutation was crossed into the background of the rps29 mutant, all of the hematopoietic and apoptotic phenotypes were rescued. Herein, the inventors demonstrate a critical role of p53 activation in rps29 mutant phenotypes. This characterization of the rps29 mutant and identification of a p53-dependent mechanism was recently published in the Journal of Experimental Hematology (Taylor et al., 2012, which is incorporated herein in its entirety by reference).

Chemical Screen Finds Specific Chk2 Inhibitors Rescue $rps29^{-/-}$ Defects

Figure 1:
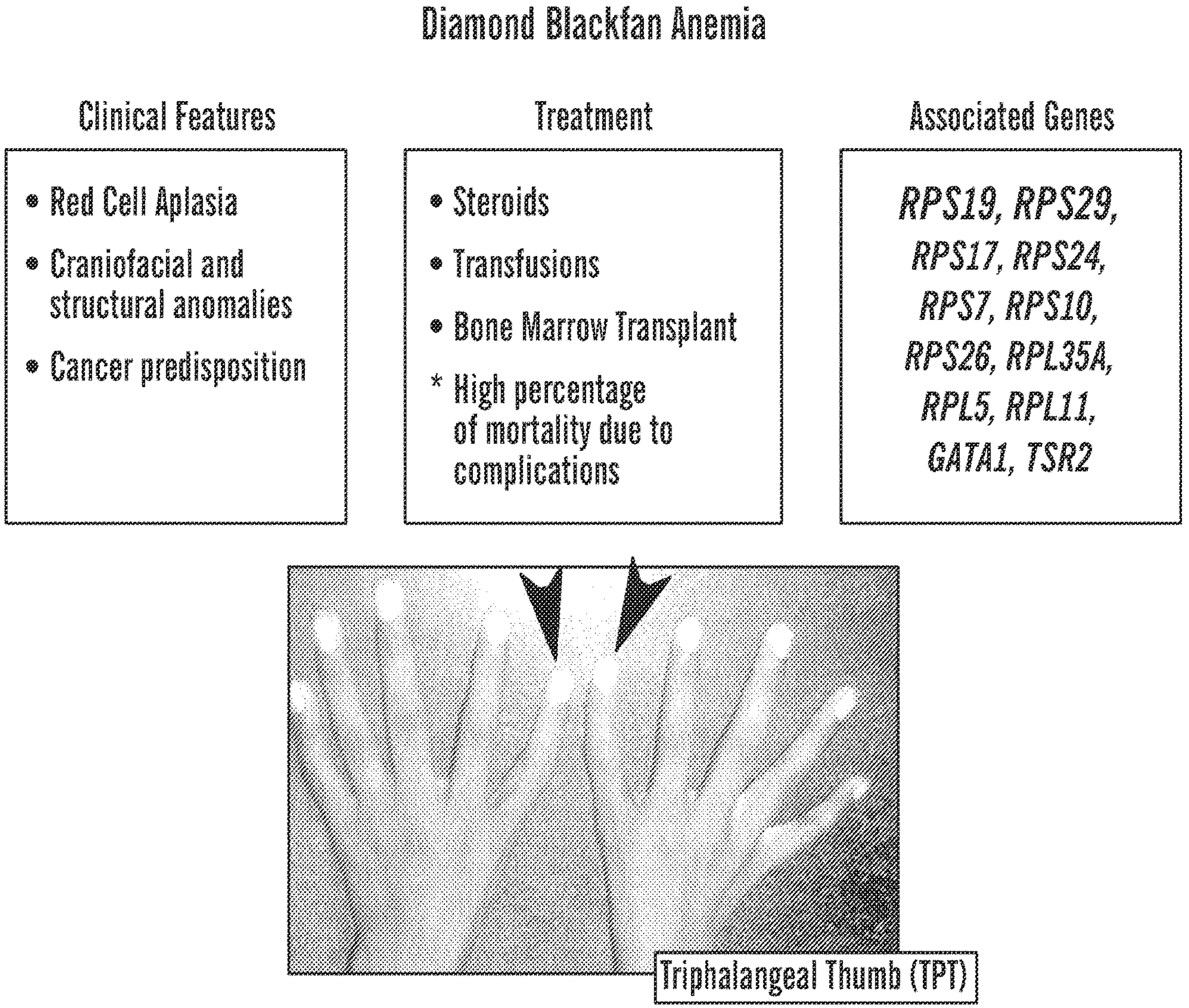
FIG. 1 shows the clinical features, treatments and genetics associated with Diamond Blackfan anemia (DBA). More than half the patients have a mutation in a ribosomal protein gene (all mutations are heterozygous). There is no effective, targeted treatment available for these patients.
Figure 3:
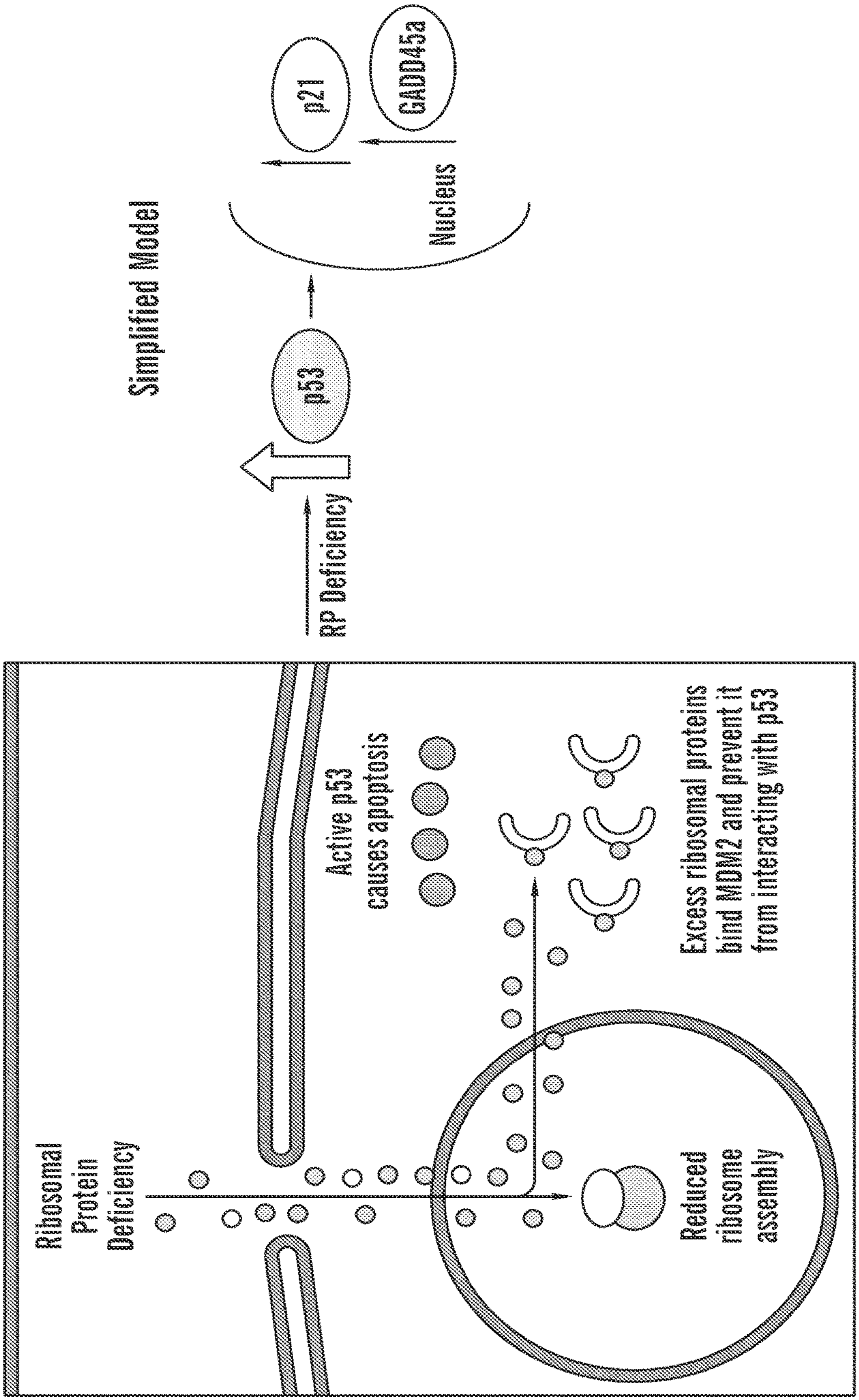
FIG. 3 is a schematic of the molecular consequences of ribosomal protein deficiency. Disruption of ribosomal biogenesis leads to p53 activation through accumulation of free ribosomal proteins binding and sequestering the negative regulator of p53, MDM2. This allows for an accumulation of active p53 in the nucleus which can then activate downstream targets of p53 such as p21 and GADD45.
Figure 4B:
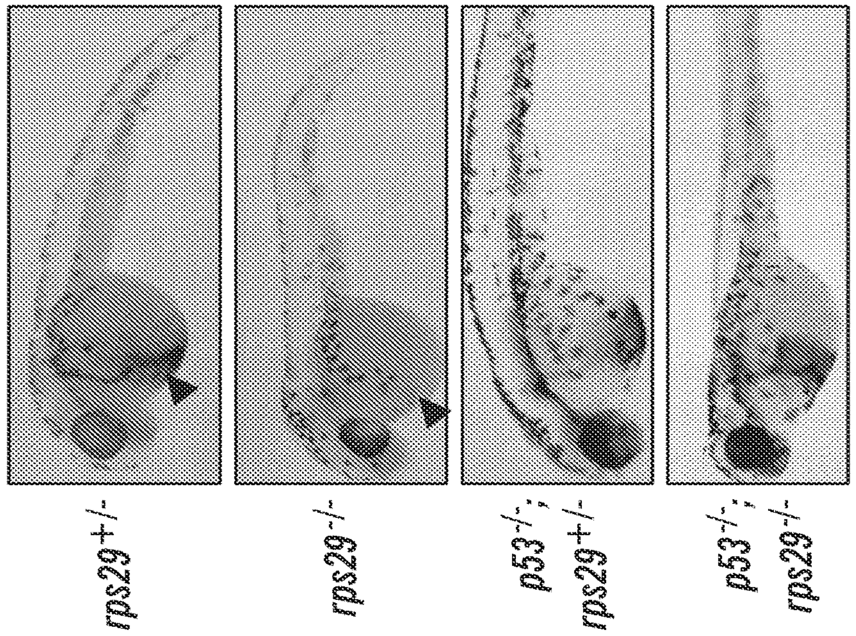
FIGS. 4A to 4B are Zebra fish potos.
Figure 4A:
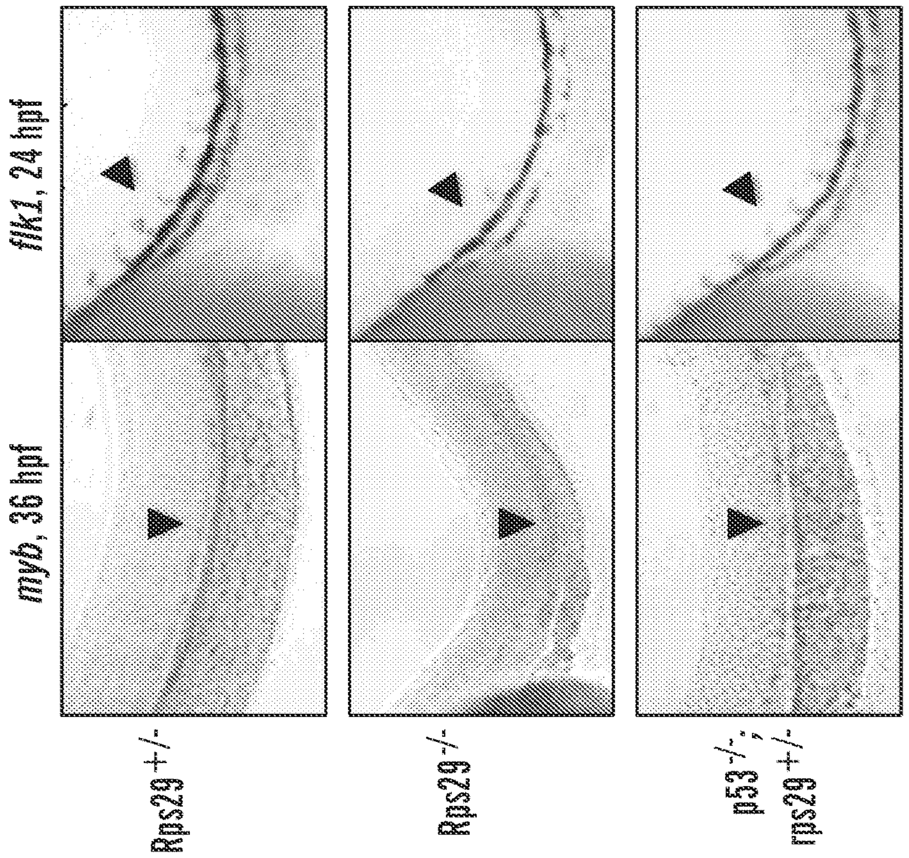
Figure 5A:
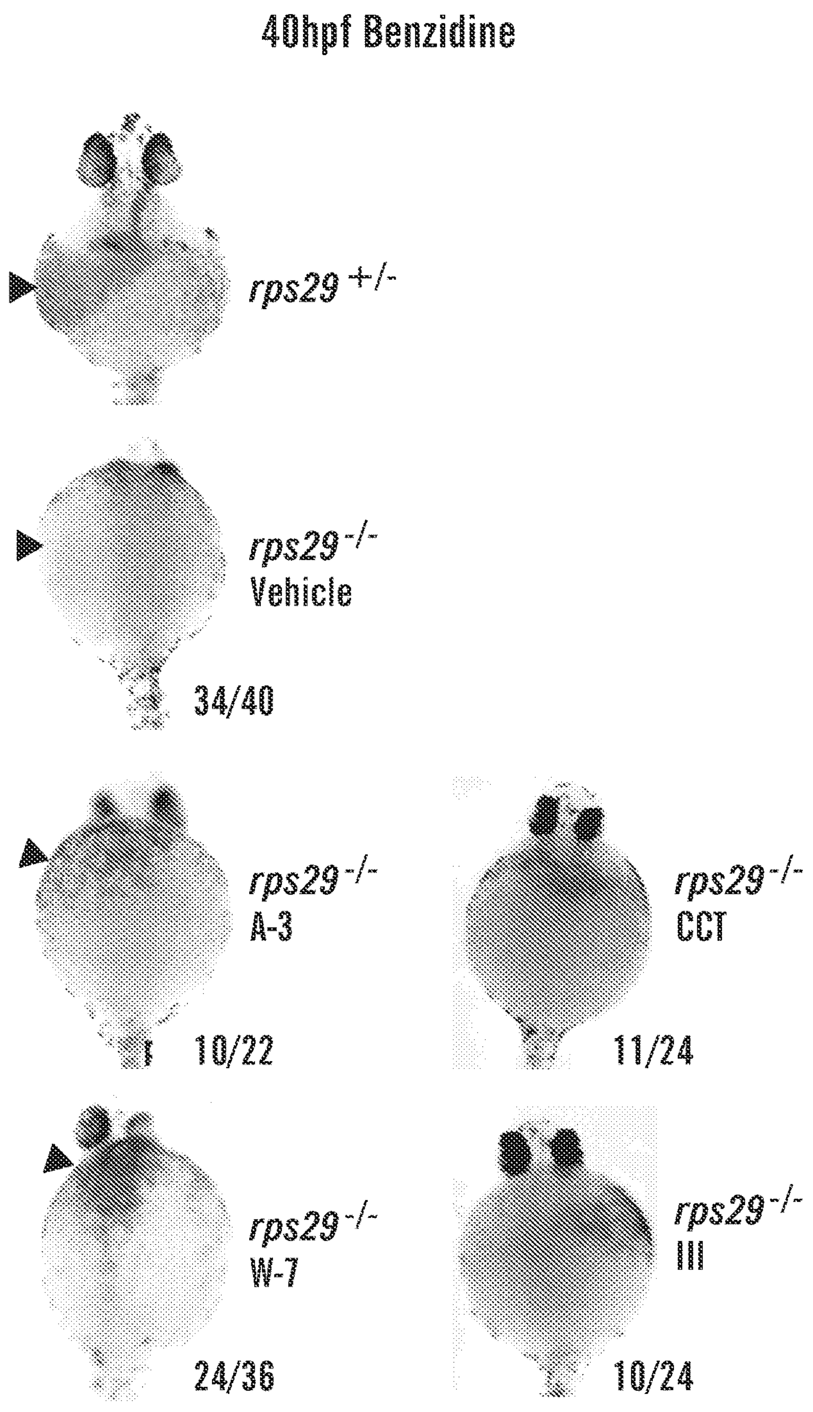
Figure 6:
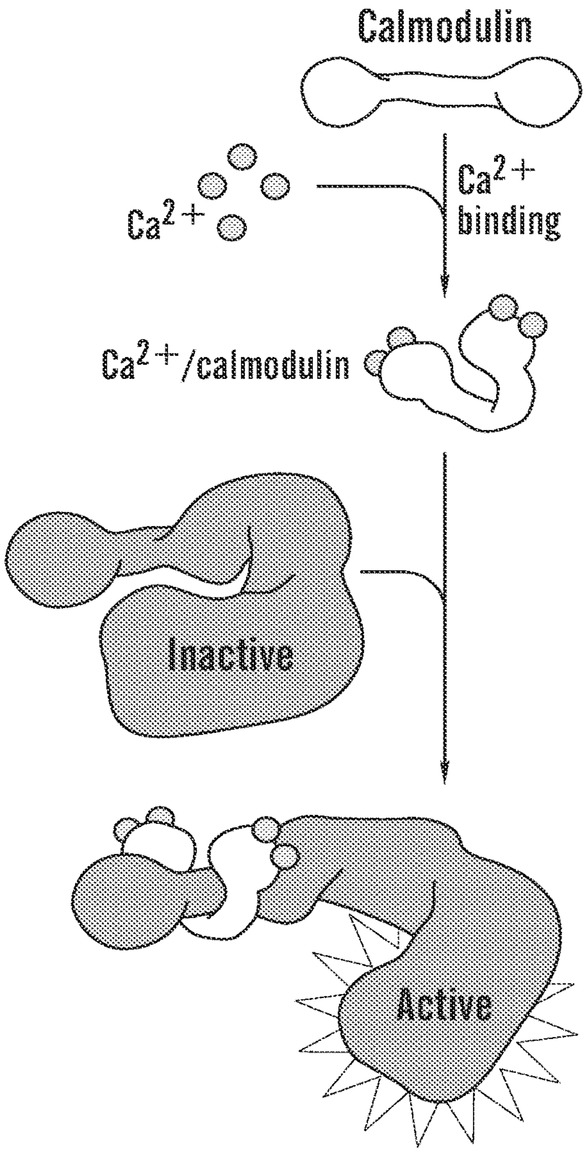
FIG. 6 shows a brief schematic of the function of Calmodulin. Calmodulin is 1) evolutionarily conserved, 2) abundant in the cell, 3) a $Ca^{2+}$ sensor, 4) Interacts with proteins, 5) Activates Kinases/phosphatases, 6) CaM inhibitors are FDA approved antipsychotics, 7) Trifluoperazine (TFP).
Figure 7A:
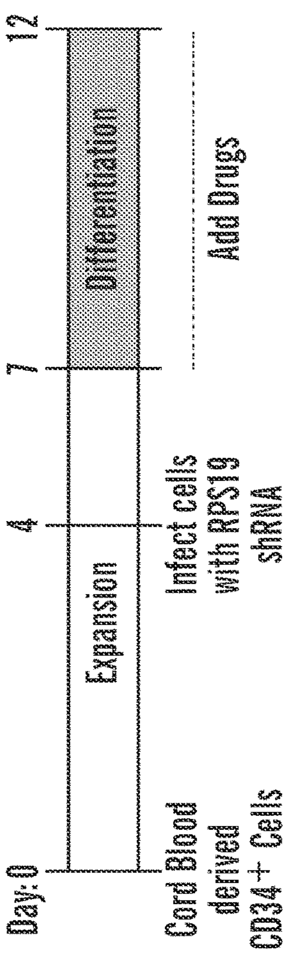
FIGS. 7A to 7C are schematics and graphs that show the results of our inhibitors in a human in vitro model of DBA.
Figure 7B:
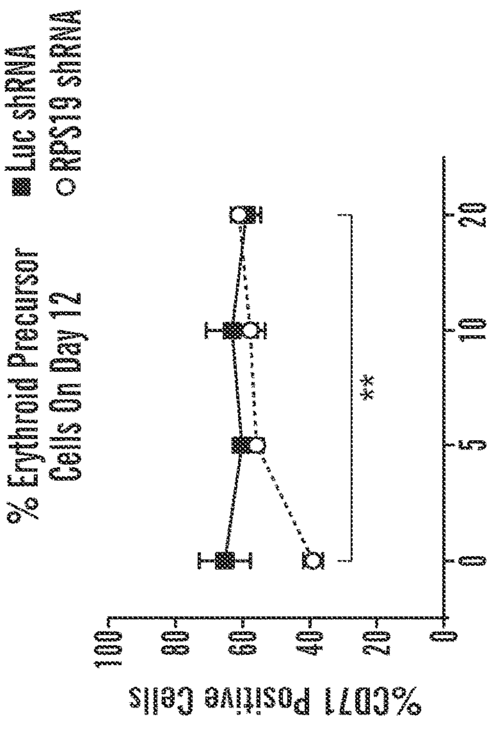
Figure 7C:
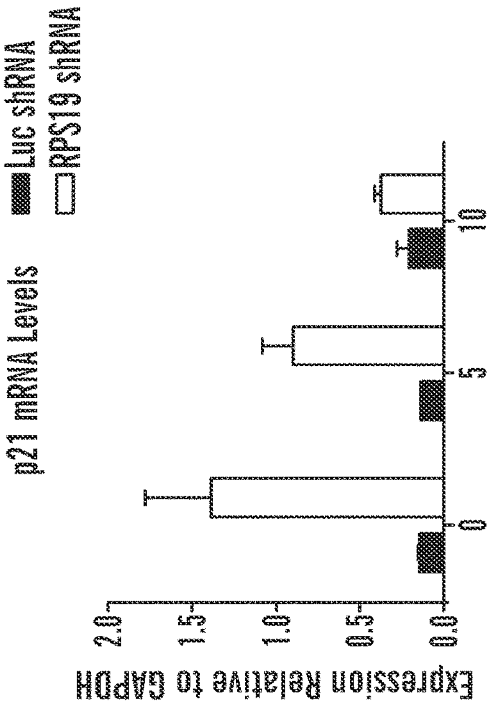
Figures 8A, 8B, 8C, 8D:
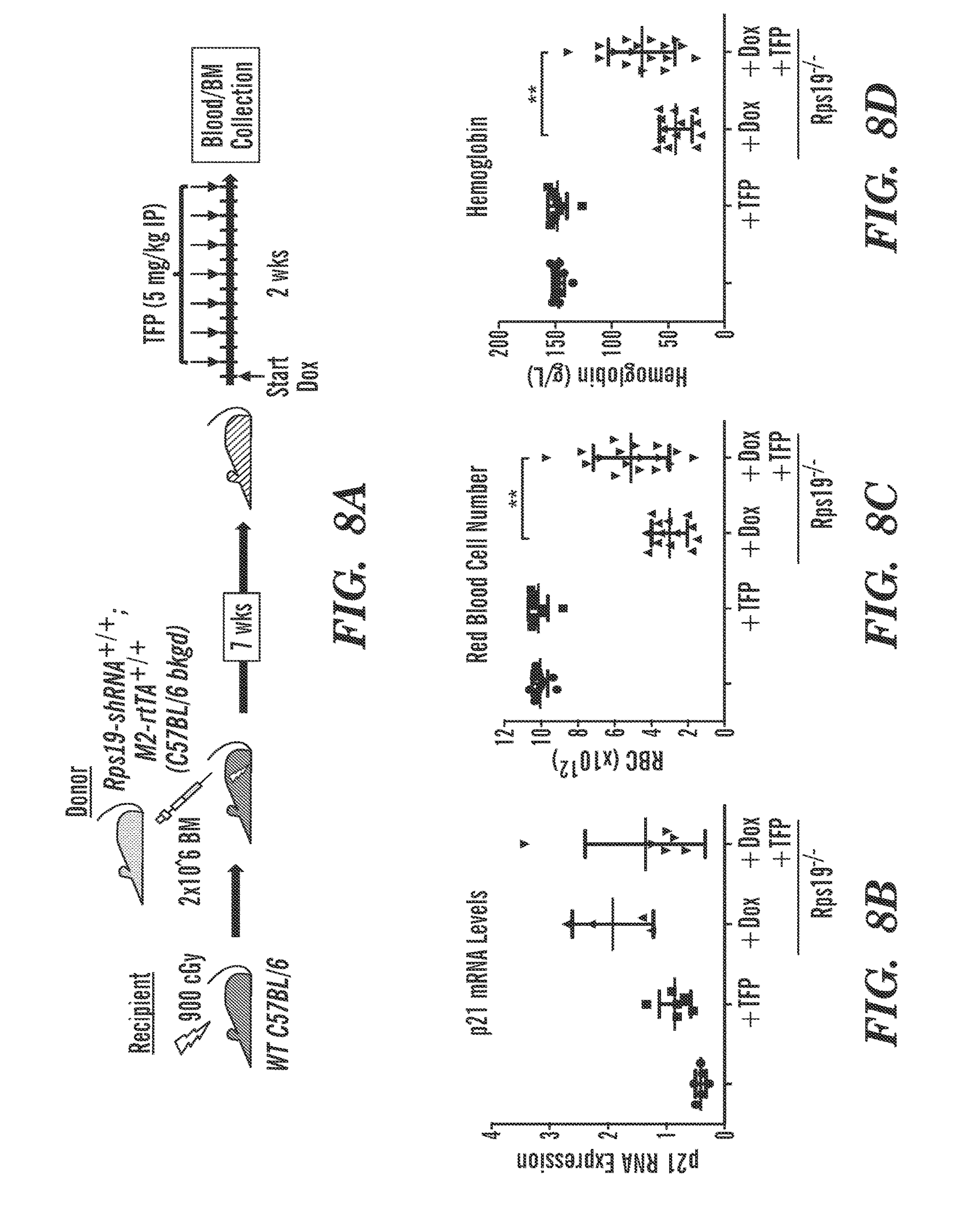
FIGS. 8A to 8D are schematics and graphs that show TFP partially rescues anemia in DBA inducible mouse model, using a dox-inducible RPS19 knockdown mouse model. (Jaako, P., et al. (2011). Blood 118, 6087-6096.) FIG. 8A, schematic of procedure. WT mice were irradiated and transplanted with marrow from a donor mouse that contains a dox-inducible hairpin against RPS19. After engraftment, mice were fed dox to induce Rps19 deficiency and treated with TFP every other day for 2 weeks. After 2 weeks, blood and bone marrow are collected for analysis.
Figure 9A:
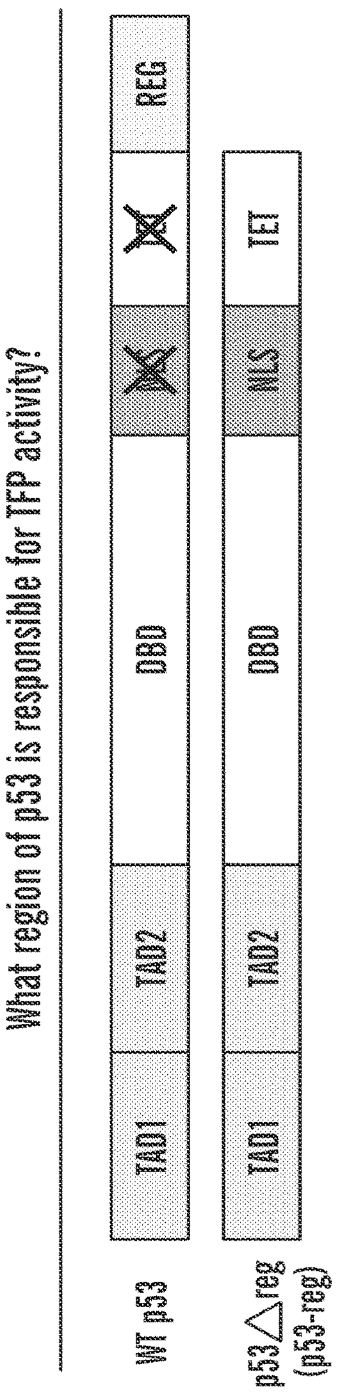
FIGS. 9A to 9C shows schematics and graphs.
Figure 9B:
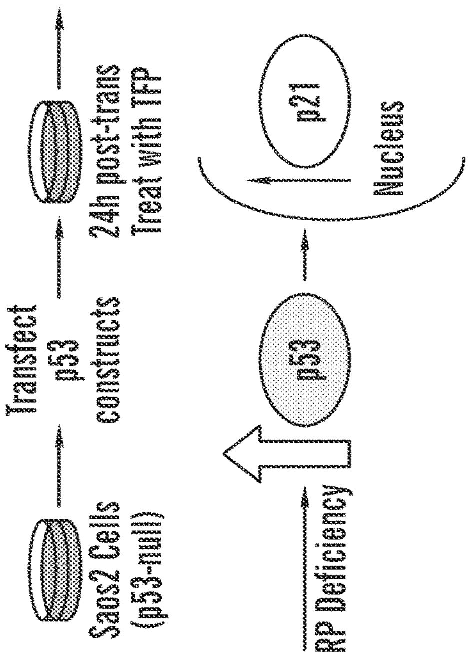
Figure 9C:
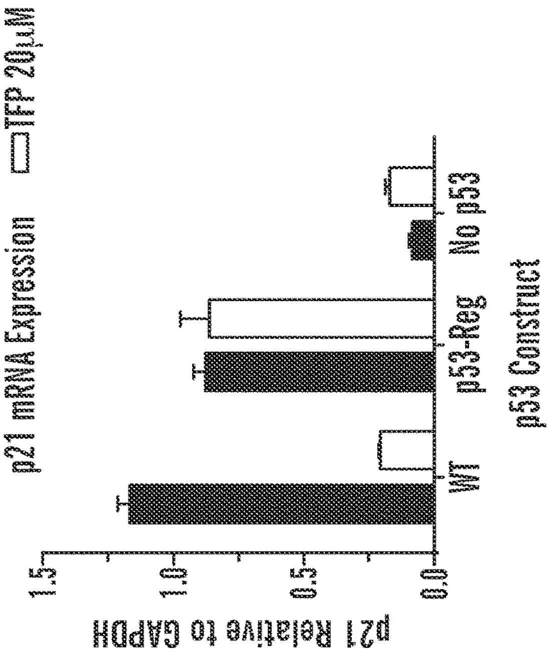
Figure 10A:
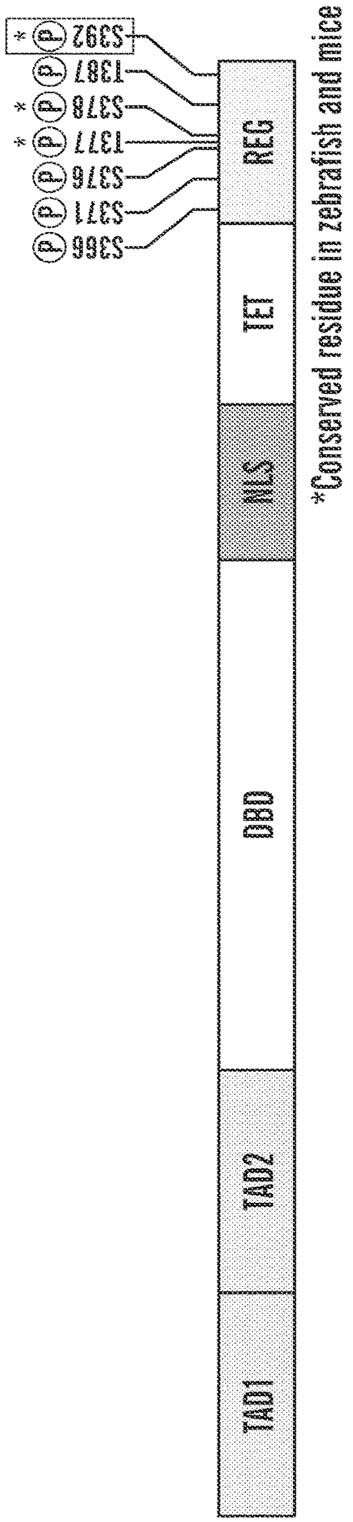
FIGS. 10A to 10C show schematics, graphs and gels that indicate CaM and Chk2 inhibitors reduce S392 phosphorylation.
Figure 10B:
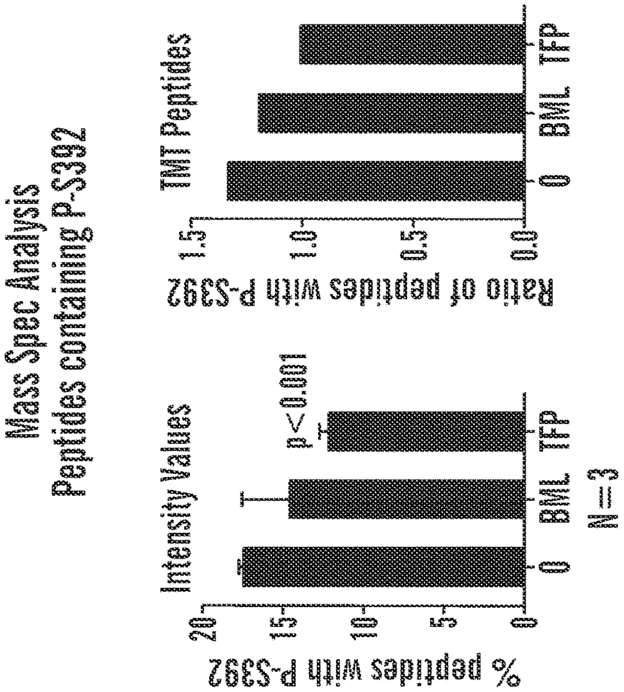
Figure 10C:
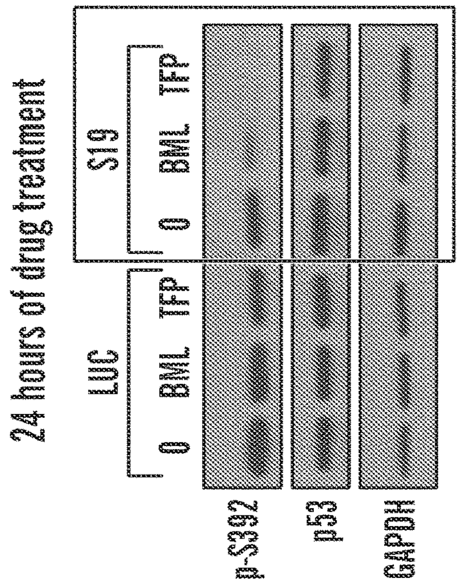
Figure 11A:
FIGS. 11A to 11C are schematics and graphs which indicate that p53 S392 phosphomimetic prevents TFP from reducing p53 activity. To confirm the importance of the ability of CaM inhibitors to block the phosphorylation of p53, we created phosphomimetic p53 by replacing S392 with an aspartic acid, which mimics constitutive phosphorylation. We also generated a control phosphomimetic p53 where S15 was replaced with aspartic acid. This mutant should have no effect on the ability of TFP to reduce p53 activity.
Figure 11B:
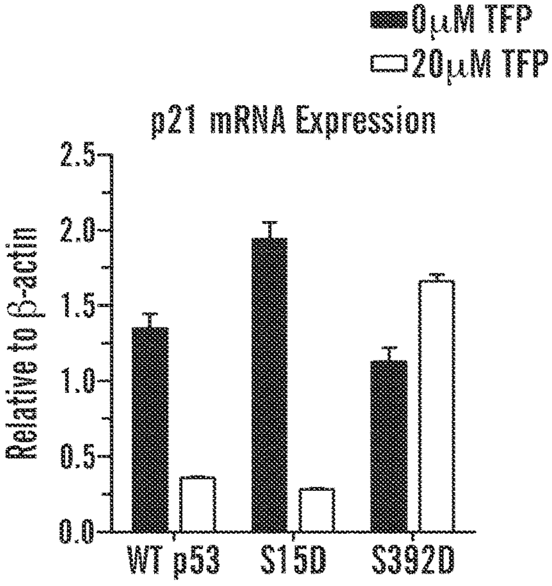
Figure 11C:
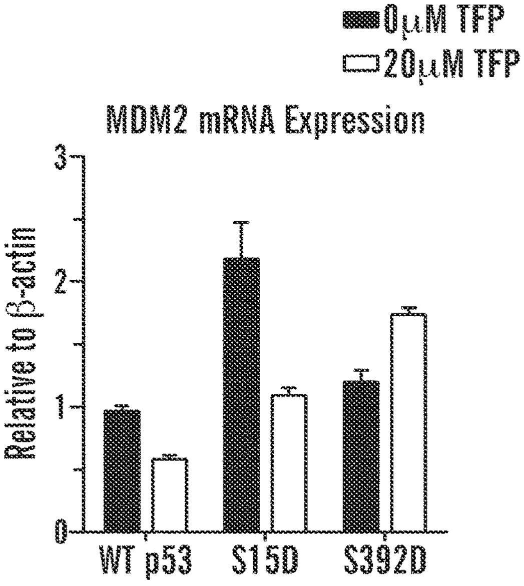
Figure 12:
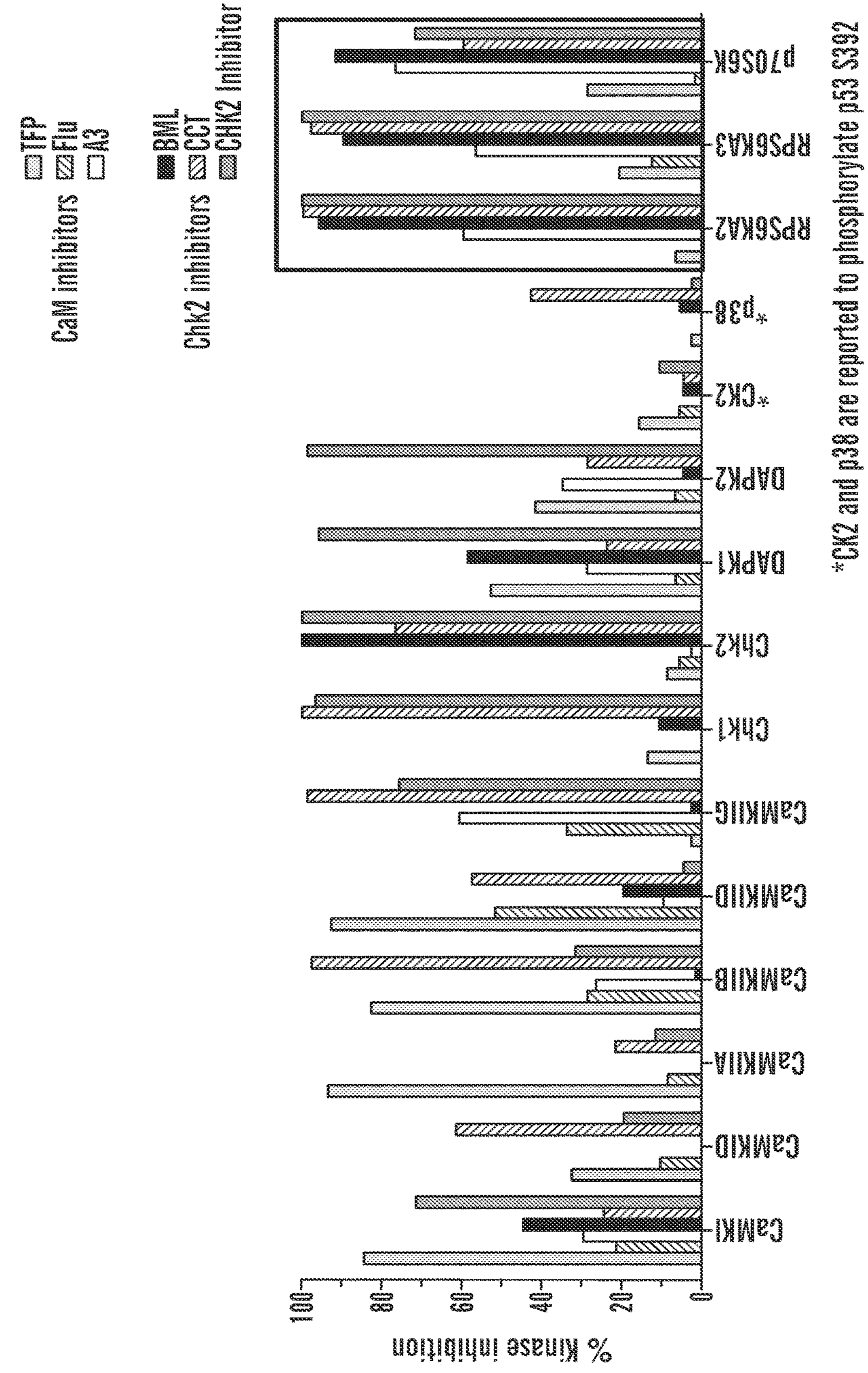
FIG. 12 shows a graph of percent inhibition of the in vitro kinase activity of CaM and Chk2 inhibitors. We asked if CaM and Chk2 inhibitors are blocking specific kinases. The known kinases that phosphorylate S392 are CK2 and p38.

A screen was performed to identify chemicals that could rescue the endothelial and morphological defects of the $rps29^{-/-}$ mutant embryo (FIG. 5). In particular, we assessed that ability of CaM dependent kinases to rescue $rps29^{-/-}$ mutant embryos. Surprisingly, out of a large number of CaM dependent kinases, only Chk2 inhibitors rescued well and then through in vitro kinase screens (See FIG. 12 and FIG. 13) we then determined the Chk2 inhibitors CCT and III are effective through inhibition of RSK and p70s6k. $Rps29^{+/-}$ fish were incrossed, and embryos were collected for treatment at bud stage (10 hpf). Embryos were treated from bud to 23 hpf with compounds of known bioactivity. After being scored for rescue of head morphology, embryos were fixed at 24 hpf for in situ hybridization and monitoring of Hb expression rescue.

The Chk2 inhibitor CCT rescues Hb.

CCT

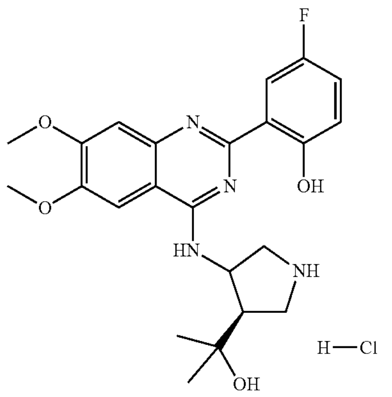

Chk2 inhibitor III rescues Hb:

III

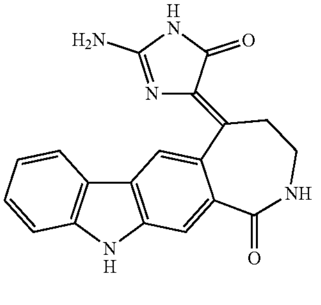

Other naphthalenesulfonamides are known to inhibit calmodulin, including A-7 and W-5, and were previously demonstrated to also rescue the vasculature defect.

Example 2

Specific Phenothiazine Derivatives Increase Hemoglobin in rps29−/− Embryos.

A Benzidine Assay was performed. For the drug treatment, rps29+/− were incrossed and embryos were collected and treated at 50% epiboly, approximately 5 hours post fertilization (hpf). Benzidine staining was performed at 40 hpf as described previously (Paffett-Lugassy and Zon, 2005). FIG. 25 shows the dramatic rescue of Hb expression, hemoglobin rescue in rps29−/− zebrafish of the compounds ACV and PerSucc. The reason for differences in Hb levels in the 0 control is that these were different experiments and there is variability in Hb among different clutches of fish.

Example 3

Novel Phenothiazine Derivatives Improve Erythroid Defects in Multiple Models of DBA We previously demonstrated that zebrafish embryos with mutations in the rps29 gene (which encodes the ribosomal protein S29) model DBA (Taylor, A. M. et al.). A subset of patients with mutations in RPS29 exists, we previously established that RPS29 is a DBA-causative gene (Mirabello, L. et al.). Consistent with other animal models of ribosomal protein dysfunction, p53 knockdown in the rps29−/− zebrafish rescues the erythroid defect. To find novel compounds that can rescue the phenotypes of DBA, we performed an in vivo chemical screen in our zebrafish DBA model and found that calmodulin (CaM) inhibitors block p53 activity and rescue the erythroid defect. Applying CaM inhibitors to human CD34+ cells deficient in RPS19 relieved the block to erythroid differentiation. Additionally, injecting the FDA-approved CaM inhibitor, trifluoperazine (TFP), into a DBA inducible mouse model (Jaako, P et al.) significantly increased red blood cell number and Hb levels and reduced p53 activity in the bone marrow. TFP belongs to a family of FDA approved antipsychotics called phenothiazines. These drugs easily cross the blood brain barrier (BBB) and their long-term use is associated with dyskinesia and extrapyramidal effects (Kennedy, P. F. et al.) making them inappropriate for use in children. To overcome this limitation, we used a library of novel phenothiazine derivatives that will potentially not cross the BBB FIG. 33. First, we tested the compounds in rps29−/− zebrafish embryos to determine if any could improve the erythroid defect FIG. 34. We looked at Hb rescue in the zebrafish. A 24 well plate was seeded with 20 embryos per well, and at 50% epiboly the embryos were treated with drug. The embryos were then stained for hemoglobin (Hb) and fixed in 4% PFA. The Eight compounds were tested and three (boxed in figure: 088-2; 088-3; and 089)) were able to increase Hb at lower concentrations than the positive control phenothiazine (fluphenazine [Flu]) (FIG. 35).

It is well established that CNS-active small molecules may have immediate neurological effects (e.g. impaired locomotor activity (Giacomini, N. J. et al.; and Boehmler, W. et al.)) in zebrafish. Zebrafish are an excellent in vivo model to study BBB permeability since the function of their BBB was shown to be similar to humans (Jeong, J. Y. et al.). To test these compounds for BBB permeability we used a high throughput behavioral testing assay for screening compounds that will affect zebrafish swimming and thus suggest BBB permeation. This assay involves placing one 6 day post-fertilization (dpf) zebrafish into a well of a 96 well plate, adding drug to each well and recording the movement for 1-2 hours using automated analysis imaging software (Rihel, J. et al.). Initially testing this assay with commercial phenothiazines we were able to statistically determine if a drug increases or decreases movement compared to DMSO treatment in the zebrafish larva (data not shown). This allows us to use behavior as a proxy for pervading the BBB in a high throughput manner. We tested four novel derivatives along with a commercial phenothiazine (Flu), and a chk2 inhibitor, as a control, that should not affect behavior. Out of the selected derivatives, three altered behavior (083, 088-3; and 089) and 089 was even toxic at the highest dose. While one drug, 088-2, did not affect the swimming behavior suggesting that it does not get into the brain of the zebrafish (FIGS. 36 to 39).

We next tested three derivatives in our primary human in vitro differentiation model of DBA. To do this we expanded CD34+ peripheral blood mononuclear cells in culture for 2 days and induced ribosomal protein deficiency with a lentivirus containing RPS19 shRNA (FIG. 40). After 3 days the cells are placed into erythroid differentiation media with or without the novel derivatives and cultured for 5 days. Erythroid differentiation is then assessed by flow cytometry analysis for the transferrin receptor, CD71+. Results demonstrated that both 088-2 and 089 increased the percentage of erythroid precursor cells compared to DMSO treated (FIG. 41). In addition, the novel derivatives increased the absolute erythroid number compared to DMSO treated (FIG. 41). These results demonstrate that the novel derivative 088-2 improves the erythroid defect in both rps29−/− zebrafish embryos and in a human in vitro model of DBA. Unlike the parent phenothiazine compounds, 088-2 does not cause behavior changes in zebrafish, suggesting that the compound is not getting in the brain. A table summarizing the activity of the compounds is found in FIG. 43.

REFERENCES

All references cited herein, in the specification and Examples are incorporated in their entirety by reference.

Boehmler, W. et al. D4 Dopamine receptor genes of zebrafish and effects of the antipsychotic clozapine on larval swimming behaviour. *Genes, Brain Behav.* 2007; 6:155-166.

Burns C E, Galloway J L, Smith A C, et al. A genetic screen in zebrafish defines a hierarchical network of pathways required for hematopoietic stem cell emergence. *Blood* 2009; 113:5776-82.

Chin D, Means A R. Calmodulin: a prototypical calcium sensor. *Trends Cell Biol* 2000; 10:322-8.

Danilova N, Sakamoto K M, Lin S. Ribosomal protein S19 deficiency in zebrafish leads to developmental abnormalities and defective erythropoiesis through activation of p53 protein family. *Blood* 2008; 112:5228-37.

Danilova N, Sakamoto K M, Lin S. Ribosomal protein L11 mutation in zebrafish leads to hematopoietic and metabolic defects. *Br J Haematol* 2011; 152:217-28.

Draptchinskaia N, Gustavsson P, Andersson B, et al. The gene encoding ribosomal protein S19 is mutated in Diamond-Blackfan anemia. *Nat Genet* 1999; 21:169-75.

Dutt S, Narla A, Lin K, et al. Haploinsufficiency for ribosomal protein genes causes selective activation of p53 in human erythroid progenitor cells. *Blood* 2011; 117:2567-76.

Ebert B L, Pretz J, Bosco J, et al. Identification of RPS14 as a 5q-syndrome gene by RNA interference screen. *Nature* 2008; 451:335-9.

Ebert B L, Lee M M, Pretz J L, et al. An RNA interference model of RPS19 deficiency in Diamond-Blackfan anemia recapitulates defective hematopoiesis and rescue by dexamethasone: identification of dexamethasone-responsive genes by microarray. *Blood* 2005; 105:4620-6.

Flygare J, Kiefer T, Miyake K, et al. Deficiency of ribosomal protein S19 in CD34+ cells generated by siRNA blocks erythroid development and mimics defects seen in Diamond-Blackfan anemia. *Blood* 2005; 105:4627-34.

Fumagalli S, Di Cara A, Neb-Gulati A, et al. Absence of nucleolar disruption after impairment of 40S ribosome biogenesis reveals an rpL 11-translation-dependent mechanism of p53 induction. *Nat Cell Biol* 2009; 11:501-8.

Giacomini, N. J., Rose, B., Kobayashi, K. & Guo, S. Antipsychotics produce locomotor impairment in larval zebrafish. *Neurotoxicol. Teratol.* 2006; 28; 245-250.

Inagaki M, Kawamoto S, Itoh H, et al. Naphthalenesulfonamides as calmodulin antagonists and protein kinase inhibitors. *Mol Pharmacol* 1986; 29:577-81.

Isenberg J S, Ridnour L A, Perruccio E M, Espey M G, Wink D A, Roberts D D. Thrombospondin-1 inhibits endothelial cell responses to nitric oxide in a cGMP-dependent manner. *Proc Natl Acad Sci USA* 2005; 102:13141-6.

Jaako P, Flygare J, Olsson K, et al. Mice with ribosomal protein S19 deficiency develop bone marrow failure and symptoms like patients with Diamond-Blackfan anemia. *Blood* 2011; 118:6087-96.

Jeong, J.-Y. et al. Functional and developmental analysis of the blood-brain barrier in zebrafish. *Brain Res. Bull.* 2008; 75:619-628.

Lu S J, Feng Q, Park J S, et al. Biologic properties and enucleation of red blood cells from human embryonic stem cells. *Blood* 2008; 112:4475-84.

Kennedy, P. F., Hershon, H. I. & Mcguire, R. J. Extrapyramidal disorders after prolonged phenothiazine therapy. *Br. J. Psychiatry* 1971; 118: 509-518.

McGowan K A, Li J Z, Park C Y, et al. Ribosomal mutations cause p53-mediated dark skin and pleiotropic effects. *Nat Genet* 2008; 40:963-70.

Mirabello, L. et al. Whole-exome sequencing and functional studies identify RPS29 as a novel gene mutated in multicase Diamond-Blackfan anemia families. *Blood* 2014; 124: 24-32 (2014).

Miyake K, Flygare J, Kiefer T, et al. Development of cellular models for ribosomal protein S19 (RPS19)-deficient diamond-blackfan anemia using inducible expression of siRNA against RPS19. Mol Ther 2005; 11:627-37.

North T E, Goessling W, Walkley C R, et al. Prostaglandin E2 regulates vertebrate hematopoietic stem cell homeostasis. *Nature* 2007; 447:1007-11.

North T E, Goessling W, Peeters M, et al. Hematopoietic stem cell development is dependent on blood flow. *Cell* 2009; 137:736-48.

Paffett-Lugassy N N, Zon L I. Analysis of hematopoietic development in the zebrafish. *Methods Mol Med* 2005; 105:171-98.

Rihel, J. et al. Zebrafish behavioral profiling links drugs to biological targets and rest/wake regulation. *Science* (80-.). 2001; 327:348-351.

Rodriguez-Vilarrupla A, Jaumot M, Abella N, et al. Binding of calmodulin to the carboxy-terminal region of p21 induces nuclear accumulation via inhibition of protein kinase C-mediated phosphorylation of Ser153. *Mol Cell Biol* 2005; 25:7364-74.

Sweitzer T D, Hanover J A. Calmodulin activates nuclear protein import: a link between signal transduction and nuclear transport. *Proc Natl Acad Sci USA* 1996; 93:14574-9.

Takagi M, Absalon M J, McLure K G, Kastan M B. Regulation of p53 translation and induction after DNA damage by ribosomal protein L26 and nucleolin. *Cell* 2005; 123:49-63.

Taules M, Rodriguez-Vilarrupla A, Rius E, et al. Calmodulin binds to p21 (Cip1) and is involved in the regulation of its nuclear localization. *J Biol Chem* 1999; 274:24445-8.

Taylor A M, Humphries J M, White R M, Murphey R D, Burns C E, Zon L I. Hematopoietic defects in rps29 mutant zebrafish depend upon p53 activation. *Exp Hematol* 2012; 40:228-37 e5.

Thisse C, Thisse B. High-resolution in situ hybridization to whole-mount zebrafish embryos. *Nat Protoc* 2008; 3:59-69.

Vlachos A, Ball S, Dahl N, et al. Diagnosing and treating Diamond Blackfan anemia: results of an international clinical consensus conference. *Br J Haematol* 2008; 142: 859-76.

Vlachos A, Muir E. How I treat Diamond Blackfan anemia. *Blood* 2010; 116:3715-23.

What is claimed:

1. A method of treating a subject with Diamond Blackfan Anemia (DBA), comprising administering an effective amount of a composition comprising an inhibitor of ribosomal s6 kinase, RSK (p90S6k), to the subject to decrease p90S6k activity and decrease active p53 in at least one of CD34+ cells, erythroid cells or erythroid differentiated cells in the subject, wherein (i) the inhibitor of p90S6k is SL0101 (SL) and has the following structure:

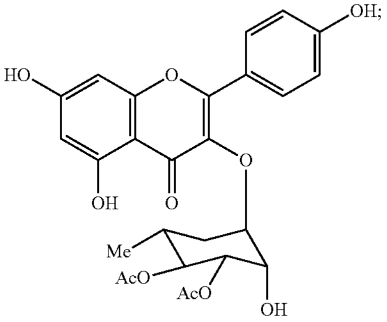 [SMILES: CC(=O)OC1C(C)CC(Oc2c(-c3ccc(O)cc3)oc3cc(O)cc(O)c3c2=O)C(O)C1OC(C)=O]

or (ii) the inhibitor of p90S6k is BI-D1870 (BI) and has the following structure

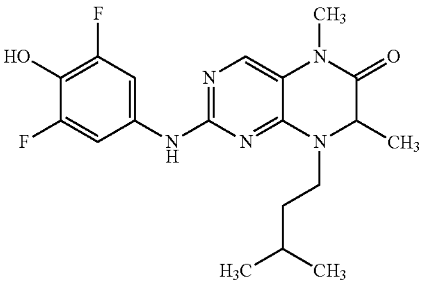

BI-D1870

2. The method of claim 1, wherein: the inhibitor of p90S6k is SL0101.

3. The method of claim 1, wherein the subject has DBA1, DBA2, DBA3, DBA4, DBA5, DBA6, DBA7, or DBA8.

4. The method of claim 1, wherein the subject as a mutation in ribosomal protein 19 (RPS19).

5. The method of claim 1, wherein the subject is administered another therapeutic agent to treat the ribosomal protein defect, selected from corticosteroids and blood transfusions.

6. The method of claim 1, wherein the inhibitor of p90S6k is BI-D1870 (BI).

* * * * *